United States Patent
Hehn et al.

(10) Patent No.: US 12,178,809 B2
(45) Date of Patent: Dec. 31, 2024

(54) PYRIDINYL SULFONAMIDE DERIVATIVES, PHARMACEUTICAL COMPOSITIONS AND USES THEREOF

(71) Applicant: Boehringer Ingelheim International GmbH, Ingelheim am Rhein (DE)

(72) Inventors: Joerg P. Hehn, Biberach an der Riss (DE); Andreas Blum, Bensheim (DE); Oliver Hucke, Warthausen (DE); Stefan Peters, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 333 days.

(21) Appl. No.: 17/285,918

(22) PCT Filed: Oct. 24, 2019

(86) PCT No.: PCT/EP2019/078992
§ 371 (c)(1),
(2) Date: Apr. 16, 2021

(87) PCT Pub. No.: WO2020/089026
PCT Pub. Date: May 7, 2020

(65) Prior Publication Data
US 2021/0361637 A1    Nov. 25, 2021

(30) Foreign Application Priority Data

Oct. 29, 2018    (EP) .................................... 18203196

(51) Int. Cl.
*A61K 31/4545* (2006.01)
*A61K 31/4427* (2006.01)
*A61K 31/4439* (2006.01)
*A61K 31/5377* (2006.01)
*C07D 401/12* (2006.01)
*C07D 401/14* (2006.01)
*C07D 405/14* (2006.01)

(52) U.S. Cl.
CPC ...... *A61K 31/4545* (2013.01); *A61K 31/4427* (2013.01); *A61K 31/4439* (2013.01); *A61K 31/5377* (2013.01); *C07D 401/12* (2013.01); *C07D 401/14* (2013.01); *C07D 405/14* (2013.01)

(58) Field of Classification Search
CPC .................................................. A61K 31/4545
See application file for complete search history.

(56) References Cited

U.S. PATENT DOCUMENTS

| | | | |
|---|---|---|---|
| 7,579,449 B2 | 8/2009 | Eckhardt et al. | |
| 7,666,848 B2 | 2/2010 | Sanofi | |
| 7,713,938 B2 | 5/2010 | Himmelsbach et al. | |
| 7,745,414 B2 | 6/2010 | Eckhardt et al. | |
| 7,767,651 B2 | 8/2010 | Kobayashi | |
| 7,919,520 B2 | 4/2011 | Bandarage et al. | |
| 7,977,466 B2 | 7/2011 | Imamura | |
| 7,989,622 B2 | 8/2011 | Bajalieh et al. | |
| 8,017,792 B2 | 9/2011 | Taisho | |
| 8,802,842 B2 | 8/2014 | Weber et al. | |
| 9,163,051 B2 | 10/2015 | Murakata | |
| 9,873,714 B2 | 1/2018 | Weber et al. | |
| 10,442,795 B2 | 10/2019 | Eckhardt et al. | |
| 10,577,363 B2 | 3/2020 | Mitchell et al. | |
| 11,001,563 B2 | 5/2021 | Luo et al. | |
| 11,505,532 B2 | 11/2022 | Luo et al. | |
| 11,649,233 B2 | 5/2023 | Wu | |
| 2008/0096892 A1 | 4/2008 | Cheng et al. | |
| 2010/0197908 A1 | 8/2010 | Lehmann-Lintz et al. | |
| 2017/0327483 A1 | 11/2017 | Blum et al. | |
| 2018/0104198 A1* | 4/2018 | Rippmann | A61P 3/04 |
| 2021/0353608 A1* | 11/2021 | Hehn | A61P 1/16 |
| 2021/0361637 A1 | 11/2021 | Hehn et al. | |

FOREIGN PATENT DOCUMENTS

| | | |
|---|---|---|
| CA | 2830157 A1 | 9/2012 |
| CN | 109251166 A | 1/2019 |
| EP | 1213296 A1 | 6/2002 |

(Continued)

OTHER PUBLICATIONS

International Search report for PCT/EP2019/078992 dated Dec. 29, 2019.

(Continued)

*Primary Examiner* — Jeffrey S Lundgren
*Assistant Examiner* — Eric Tran
(74) *Attorney, Agent, or Firm* — Shelley A. Jones

(57) ABSTRACT

The invention relates to new pyridinyl sulfonamide derivatives of the formula

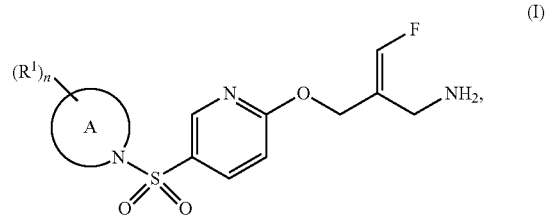

wherein $R^1$, A and n are as defined herein, to their use as medicaments, to methods for their therapeutic use and to pharmaceutical compositions containing them.

26 Claims, No Drawings

(56) References Cited

FOREIGN PATENT DOCUMENTS

| | | | |
|---|---|---|---|
| EP | 1344780 | A1 | 9/2003 |
| EP | 1354888 | A1 | 10/2003 |
| EP | 1489089 | A1 | 12/2004 |
| EP | 2695881 | A1 | 2/2014 |
| EP | 3617186 | A1 | 3/2020 |
| EP | 3626699 | A1 | 3/2020 |
| EP | 3715341 | A1 | 9/2020 |
| JP | 2008512346 | A | 4/2008 |
| WO | 1998027086 | A1 | 6/1998 |
| WO | 0127128 | A1 | 4/2001 |
| WO | 20010023594 | A2 | 4/2001 |
| WO | 2003099836 | A1 | 12/2003 |
| WO | 2005012326 | A1 | 2/2005 |
| WO | 2006028269 | | 3/2006 |
| WO | 2007120528 | A2 | 10/2007 |
| WO | 2007140191 | A2 | 12/2007 |
| WO | 2008002824 | A1 | 1/2008 |
| WO | 2008042688 | A2 | 4/2008 |
| WO | 2008069327 | A1 | 6/2008 |
| WO | 2008071646 | A1 | 6/2008 |
| WO | 2008116179 | A1 | 9/2008 |
| WO | 2009014970 | A1 | 1/2009 |
| WO | 2009026319 | A1 | 2/2009 |
| WO | 2009035969 | A1 | 3/2009 |
| WO | 2010009197 | A1 | 1/2010 |
| WO | 2010119990 | A1 | 10/2010 |
| WO | 12120195 | A1 | 9/2012 |
| WO | 12124696 | A1 | 9/2012 |
| WO | 2013163675 | A1 | 11/2013 |
| WO | 2017022861 | A1 | 2/2017 |
| WO | 2017148519 | A1 | 9/2017 |
| WO | 2017194453 | | 11/2017 |
| WO | 2018028517 | A1 | 2/2018 |
| WO | WO-2018027892 | A1 * | 2/2018 .......... A61K 31/395 |
| WO | 2018146471 | A1 | 8/2018 |
| WO | 2018148856 | A1 | 8/2018 |
| WO | 2018149226 | A1 | 8/2018 |
| WO | 2019201752 | | 10/2019 |

OTHER PUBLICATIONS

Written Opinion for PCT/EP2019/078992 dated Dec. 29, 2019.
International Search Report for PCT/EP2016/054541 dated May 27, 2016.
International Search Report for PCT/EP2016/054540 dated May 25, 2016.
Nobili, World Journal of Gastroenterolgy, Pediatric non alcoholic fatty Liver disease: preventive and therapeutic value of lifestyle intervention, 2009.
Shen, UC Berkley E thesis and Dissertations, In Search of pysiological role for amine oxidase, cooper containing -3 (AOC3) in adipocytes, 2010.
International Search Report and Written Opinion for PCT/EP20170600890, dated Jun. 6, 2017.
Yamaki, Synthesis and structure activity relationships of carbamimidoylcarbamate derivatives as novel vascular adhesion protein-1 inhibitors, Bioorganic and medicinal Chemistry, 2017, p. 6024-6038.
Seufert, SGLT inhibitors-an insulin independent therapeutic approach, Diabetes, 2015.
Bell, The potent synergistic effects of the combination of liraglutide, Amercian J. of Case reports, vol. 15, 2014.
Abdul-Ghani, Where does Combination Therapy with an SGLT2 Inhibitor, Diabetes Care, vol. 38, 2015.
International Search Report for PCT/Ep2019/059341 dated Mar. 7, 2019.
Written Opinion of the International Search Authorty, PCT/EP/2019/059341 dated Mar. 7, 2019.
Gressner, Validity of Monoamine Oxidase In Serum for Diagnosis of Liver Cirrhosis, J. Clin Chem. Biochem, 1982.
Kleiner, Design and Validation of a Histological scoring System, Hepatolology, 2005.
McEwen, Abnormalities of Serum monoamine oxidase in chronic Liver Disease, J. Lab A. Clin. Med., 1967.
Chassande, The human gene for Diamine Oxidase, The Journal of Biological Chemistry, 1994.
Imamura, Human Retina-Specific Amine Oxidase cDNA cloning, Tissue Expression, Genomica, vol. 40, 1996.
Schwelberger, The origin of mammalian plasma amine oxidases, J. Neural Transm, vol. 114, 2007.
Dunkel, Semi-carbazide-Sensitive Amine Oxidase/Vascular Adhesion Protein 1, Current Medicinal Chem, vol. 15, 2008.
Katsuki, Homeostasis Model Assesssment is a reliable indicator of insulin resistance during follow up of patients with type 2 diabetes, Diabestes Care, vol. 24, 2001.
Matthews, Homeostasis model assessment: insulin resistance, Diabetologica, vol. 28, 1985.
Galvin, A simple method for Quantitiation of Insulin Sensitivity, Diabetic Meds, 1992.
Meigs, The Natural History of progressionform Normal glucose toleranceto type 2 diabetes, Diabestes, vol. 82, 2003.
Diabetes Care, The Prevention or Delay of Type 2 Diabetes, American Diabetes Assoc., vol. 25, 2002.
Stomvall, The OGTT test as test for beta cell function?, European J. of clinical Investigation, vol. 31, 2001.
Laaksonen, Metabolic Syndrome and Development of Diabetes Mellitus, American Journal od Epidemiology, 2002.
Stomvall, Use of the Oral Glucose Tolerance Test to Assess Insulin Release and Insulin Sensitivity, Diabetes Care, vol. 23, 2000.
Grempler, Empagliflozin, a novel selective sodium co-transorter-2 inhibitor, Diabetes, Obesity and Metabolism, vol. 14, 2012.
Zinman, Empagliflozin, Cardiovascular Outcomes and Mortality in Type 2 Diabetes, New England Journal of Med., 2015.
Folch, A simple method for the isolation and purification of total lipides from animal tissues, J. biol Chem, 1957.
Jojima, Empaglaiflazin, alone or in combo with linagliptin a DPP-4 inhibitor prevents steatohepatitis in a novel mouse model of non-alcoholic steatohepatitis and diabetes, Diabetology & Metabolic Syndrome, 2016.
Brnardic et al., "Discovery of pyrrolidine sulfonamides as selective and orally bioavailable antagonists of transient receptor potential vanilloid-4 (TRPV4)", Journal of Medicinal Chemistry, 2018, 61.21, pp. 9738-9755.
Ford et al., "Prevalence of the Metabolic Syndrome among US adults: Findings from the Third National Health and Nutrition Examination Survey", JAMA, 2002, vol. 287, pp. 356-359.
Forst et al., "Clinical Therapeutics, Treatment of Insulin Resistance", British Library, 2020, 1989-PO, p. A459.
Cleeman et al., "Executive Summary of the Third Report of the National Cholesterol Education Program (NCEP) Expert Panel on Detection, Evaluation, and Treatment of High Blood Cholesterol in Adults (Adult Treatment Panel III)", JAMA, 2001, vol. 285, pp. 2486-2497.
Foot et al., "PXS-4681A, a Potent and Selective Mechanism-Based Inhibitor of SSAO/VAP-1 with Anti-Inflammatory Effects In Vivo", The Journal of Pharmacology and Experiment Therapeutics, Nov. 30, 2013, vol. 347, pp. 365-374.
Abstract in English for CN109251166, Jan. 22, 2019.
Abstract in English for WO2019024924, Feb. 7, 2019.
Giron, "Thermal analysis and calorimetric methods in the characterisation of polymorphs and solvates", Thermochimica acta, Elsevier Science, B.V., vol. 248, 1995, p. 1-59.
Remington's "Atomic and Molecular Structure and States of the Matter", Pharmaceutical Sciences, 16th Edition, Mack Pub. Co., 1990, p. 180-181.

* cited by examiner

PYRIDINYL SULFONAMIDE DERIVATIVES, PHARMACEUTICAL COMPOSITIONS AND USES THEREOF

FIELD OF THE INVENTION

This invention relates to new compounds, in particular pyridinyl sulfonamide derivatives, to processes for preparing such compounds, to their use as inhibitors of AOC3, to methods for their therapeutic use, in particular in diseases and conditions mediated by the inhibition of AOC3, and to pharmaceutical compositions comprising them.

BACKGROUND OF THE INVENTION

The enzymatic activity of AOC3 (amine oxidase, copper containing 3; vascular adhesion protein 1) has been described already in 1967 as a monoamine oxidase activity in the plasma of chronic liver disease patients (Gressner, A. M. et al., 1982, J. Clin. Chem. Clin. Biochem. 20: 509-514; McEwen, C. M., Jr. et al., 1967, J. Lab Clin. Med. 70: 36-47). AOC3 has two closely homologous genes in the human genome: AOC1 which corresponds to a diamine oxidase (Chassande, O. et al., 1994, J. Biol. Chem. 269: 14484-14489) and AOC2, a SSAO with a specific expression in the retina (Imamura, Y. et al., 1997, Genomics 40: 277-283). AOC4 is a sequence that does not lead to a functional gene product in humans due to an internal stop-codon (Schwelberger, H. G., 2007, J. Neural Transm. 114: 757-762).

The enzyme contains an oxidized 2,4,5-trihydroxy-phenylalaninequinone (TPQ) and a copper ion in the active side. This characteristic catalytic center classifies the semi-carbazide-sensitive amine oxidase (SSAO, copper-containing amine:oxygen oxido-reductase (deaminating)): The type II membrane protein belongs to the family of copper containing amine oxidases together with several other diamine and the lysyl oxidases. However, the later enzymes can be distinguished from AOC3 in their preference for diamines and the low sensitivity towards semicarbazide inhibition (Dunkel, P. et al., 2008, Curr. Med. Chem. 15: 1827-1839). On the other hand, monoamine oxidases contain the flavin adenine dinucleotide (FAD) cofactor in their reactive center like monoamine oxidase A (MAO-A) and monoamine oxidase B (MAO-B) and follow therefore a different reaction scheme.

AOC3 catalyzes a two-step reaction mechanism for the oxidative deamination of primary aliphatic and aromatic amines. In a first reaction, the primary amine forms a Schiff-base with a TPQ carbonyl group. After abstraction of a proton from the carbon in α-position to the amino group, hydrolysis takes place and an aldehyde and the aminoquinol form of TPQ are formed in the active site. In the presence of oxygen, the aminoquinol form of TPQ is oxidized and hydrolyzed to re-generate TPQ under the formation of ammonia and peroxide with the help of the copper ion (Mure, M. et al., 2002, Biochemistry 41: 9269-9278). Several substrates of AOC3 have been described, like the physiological amines methylamine, dopamine, or aminoacetone, whose products of oxidation have been associated to cardiovascular pathologies (Yu, P. H. et al., 1993, Diabetes 42: 594-603). Synthetic amines have been optimized for their turnover by AOC3 like benzylamine derivates (Yraola, F. et al., 2006, J. Med. Chem. 49: 6197-6208), C-Naphthalen-1-methylamine (Marti, L. et al., 2004, J. Med. Chem. 47: 4865-4874) or luciferin derivates (Valley, M. P. et al., 2006, Anal. Biochem. 359: 238-246). The later substrate can be used for the sensitive detection of AOC3 activity in plasma, tissue or for biochemical characterization of the enzyme.

Under pathophysiological conditions of high AOC3 activity the aldehyde products are highly reactive, leading to advanced glycosylation end products (Mathys, K. C. et al., 2002, Biochem. Biophys. Res. Commun. 297: 863-869) which are regarded as markers and drivers of diabetes associated inflammatory mechanisms.

Furthermore, the byproduct hydrogen peroxide is sensed by the tissue as a messenger of inflammation. This reaction product is able to activate the endothelium and is fostering the activation of leukocytes.

The binding and modification of Siglec-10 as a membrane bound substrate provides a mechanistic understanding of how the enzymatic reaction could trigger the leukocyte transmigration through activated endothelia. The binding of Siglec-10 to AOC3 was shown in several adhesion assays and led to increased hydrogen peroxide production (Kivi, E. et al., 2009, Blood 114: 5385-5392). Binding of activated leukocytes to the dimeric, extracellular AOC3 via the Siglec-10 generates a transient association to the activated endothelium. Therefore, the rolling velocity of leukocytes is reduced, which increases the transmigration of leukocytes into the interstitium of inflamed tissues. Further, a conserved RGD-motif on the surface of AOC3 argues for its adhesive role:

The deletion of this sequence reduced leukocyte recruitment (Salmi, M. et al., 2000, Circ. Res. 86: 1245-1251), probably via a lack of integrin β1 binding activity (Aspinall, A. I. et al., 2010, Hepatology 51: 2030-2039).

This finding correlates to the phenotype of AOC3 knock out mice, which exert a reduced leukocyte and lymphocyte transmigration capacity (Stolen, C. M. et al., 2005, Immunity. 22: 105-115) into lymphoid organs and adipose tissue (Bour, S. et al., 2009, Am. J. Pathol. 174: 1075-1083).

AOC3 activity can be found in most tissues and is mainly expressed in endothelial cells, smooth muscle cells and adipocytes (Boomsma, F. et al., 2000, Comp Biochem. Physiol C. Toxicol. Pharmacol. 126: 69-78; O'Sullivan, J. et al., 2004, Neurotoxicology 25: 303-315). In humans, in contrast to mice, AOC3 activity is constitutive in the liver sinusoideal endothelial cells (McNab, G. et al., 1996, Gastroenterology 110: 522-528) and mRNA expression is further upregulated under inflammatory conditions in this tissue (Lalor, P. F. et al., 2002, Immunol. Cell Biol. 80: 52-64); Bonder, C. S. et al., 2005, Immunity. 23: 153-163). AOC3 not only exists as a membrane protein, but can also be found as soluble plasma activity probably due to a metalloprotease mediated shedding process (Abella, A. et al., 2004, Diabetologia 47: 429-438); Boomsma, F. et al., 2005, Diabetologia 48: 1002-1007; Stolen, C. M. et al., 2004, Circ. Res. 95: 50-57)). Elevated levels of soluble AOC3 have been observed in diabetes (Li, H. Y. et al., 2009, Clin. Chim. Acta 404: 149-153), obesity (Meszaros, Z. et al., 1999, Metabolism 48: 113-117; Weiss, H. G. et al., 2003, Metabolism 52: 688-692), congestive heart failure (Boomsma, F. et al., 1997, Cardiovasc. Res. 33: 387-391), hemorrhagic stroke (Hernandez-Guillamon, M. et al, 2012, Cerebrovasc. Dis. 33, 55-63), end-stage renal disease (Kurkijarvi, R. et al., 2001, Eur. J. Immunol. 31: 2876-2884) and inflammatory liver disease (Kurkijarvi, R. et al., 1998, J. Immunol. 161: 1549-1557). For the latter, levels of AOC3 plasma activity have been correlated to liver fibrosis and serve as a predictor in patients with NAFLD (Weston, C. J. et al., 2011, J. Neural Transm. 118: 1055-1064). After transplantation of cirrhotic livers, high AOC3 plasma levels returned to normal values, which argues for the liver as the major source of plasma AOC3 activity under this pathological condition (Boomsma, F. et al., 2003, Biochim. Biophys. Acta 1647: 48-54).

The role of AOC3 in the activation of inflammation via peroxide generation and the recruitment of leukocytes to activated endothelium makes it an attractive target for the treatment of inflammatory components in several diseases. Therefore a variety of small molecular compounds and antibodies have been tested in different disease animal models. Amongst those, the inhibition of AOC3 showed beneficial effects in the models of melanoma and lymphoma cancer (Marttila-Ichihara, F. et al., 2010, J. Immunol. 184: 3164-3173), acute and chronic joint (Tabi, T. et al., 2013, J. Neural Transm. 120: 963-967) or lung (Foot, J. S. et al., 2013, J. Pharmacol. Exp. Ther. 347: 365-374, Schilter, H. C. et al., 2015, Resp. Res. 16:42) inflammation, diabetic macular edema (Inoue, T. et al., 2013, Bioorg. Med. Chem. 21:1219-1233), kidney fibrosis (Wong, M. et al., 2014, Am. J. Physiol Renal Physiol 307: F908-F916), liver allograft rejection (Martelius, T. et al., 2004, Am. J. Pathol. 165: 1993-2001) and non-alcoholic liver disease.

The development of a potent and well tolerated AOC3 inhibitor would therefore be beneficial for the treatment of the respective human diseases.

The amine oxidase copper containing 2 (AOC2) enzyme is a family member of homodimeric amine oxidases sensitive to the inhibition of semicarbazide. The human enzyme shares 65% of its amino acids with the closest homolog AOC3 (Zhang et al., 2003, Gene 318: 45-53). Recombinant overexpression of the longer version sv1 provides evidence of cell surface expression and enzymatic activity, whereas the shorter version sv2 remains cytoplasmatic in a HEK293 in vitro expression system. AOC2 and AOC3 exhibit different substrate profiles due to structural differences in the active sites: AOC2 exerts a high prevalence for 2-phenylethylamine and tryptamine and a low activity on the turnover of methylamine or benzylamine compared to AOC3 enzymatic activity. Nevertheless, both enzymes can form heterodimers that reconstitute enzymatic active centers with retained substrate selectivity. Expression analysis of AOC2 mRNA shows a broad expression of the two splice variants sv1 and sv2 of the AOC2 gene in lung, brain, heart, liver, kidney, pancreas and peripheral blood lymphocytes (Kaitaniemi et al., 2009, Cellular and Molecular Life 66: 2743-2757). According to AOC2 enzymatic tissue activity, the only human tissue with high AOC2-like activity is the retina and expression is associated to the retinal capillaries as shown by immune-histological studies. In the mouse, the highest mRNA expression of AOC2 is also found in the mouse retina, however the signals of mRNA and protein expression are found predominantly in the retinal ganglion cell layer. In the rat, the genomic sequence of AOC2 gene contains a stop codon in the exon 1 region, which defines the peptide length to 17% of the mouse and human AOC2 protein giving rise to a non-functional protein (Zhang et al., 2003, Gene 318: 45-53).

According to enzymatic function and localization of expression, AOC2 physiological function can be reminiscent of the AOC3 homolog which is described as relevant for e.g. neurovascular, retinal inflammation and recruitment of immune cells (Matsuda et al., 2017, Invest Ophthalmol Vis Sci. 58(7): 3254-3261, Noda et al., 2008, FASEB J. 4: 1094-103). Data on pharmacological inhibition or genetic depletion of AOC2 is not available so far and it is therefore difficult to estimate the contribution of AOC2 to retinal-vascular inflammation.

Nonetheless, as compared to AOC3 inhibition alone, a combined inhibition of AOC2 and AOC3 might increase anti-inflammatory potency in man, in particular for the treatment of ocular diseases.

AOC3 inhibitors are known in the art, for example, the compounds disclosed in WO 2013/163675, WO 2018/027892, WO 2018/148856 and WO 2018/149226. The pyridinyl sulfonamide derivatives of the present invention may provide several advantages, such as enhanced potency, improved selectivity, reduced plasma protein binding, improved CYP (cytochrome P450) enzyme profile and high metabolic stability, high chemical stability, improved tissue distribution, e.g. reduced brain exposure, improved side effect profile and/or tolerability and in consequence low toxicity, reduced risk to cause adverse events or undesirable side effects, and enhanced solubility.

The pyridinyl sulfonamides of the present invention exhibit increased inhibition of human AOC2.

The pyridinyl sulfonamide derivatives of the present invention exhibit increased selectivity towards AOC1. AOC1 expression and enzymatic activity is mainly found in the gut, placenta and kidney. The enzyme catalyzes the oxidation of primary amines derived from nutrition and protects the individuum from cardiometabolic effects of histamine, putrescine, tryptamine and cadaverine. Inhibition of AOC1 can lead to impaired tolerance to ingested histamine, resulting in increased plasma and tissue histamine-levels which can cause adverse events or undesirable side effects like decreased aterial pressure and compensation by increased heart-rate, tachycardia, headache, flush, urticaria, pruritus, bronchospasm and cardiac arrest (Maintz L. and Novak N. 2007. Am. J. Clin. Nutr. 85: 1185-96). The consequence of AOC1 inhibition in combination with histamine intake has been demonstrated in experiments with pigs: After the application of the AOC1-inhibitor aminoguanidine (100 mg/kg) and gavage of histamine (2 mg/kg) animals experienced increased histamine blood levels accompanied with a drop of blood pressure, increased heart rate, flushing, vomiting and death (3 out of 15 animals) (Sattler J. 1988. Agents and Actions, 23: 361-365) under the experimental conditions. Histamine intolerance in humans was associated to mutations in the promoter region of AOC1, leading to reduced mRNA expression and plasma AOC1 activity (Maintz et al. 2011. Allergy 66: 893-902).

AIM OF THE PRESENT INVENTION

The aim of the present invention is to provide new compounds, in particular new pyridinyl sulfonamide derivatives, which are active with regard to AOC2 and AOC3.

A further aim of the present invention is to provide new compounds, in particular new pyridinyl sulfonamide derivatives, which have an inhibitory effect on AOC2 and AOC3 in vitro and/or in vivo and possess suitable pharmacological and pharmacokinetic properties to use them as medicaments.

A further aim of the present invention is to provide effective dual AOC2 and AOC3 inhibitors, in particular for the treatment of various diseases, for example of cancer, NASH (non-alcoholic steatohepatitis), pulmonary fibrosis, retinopathy, nephropathy and stroke, in particular hemorrhagic stroke.

Another aim of the present invention is to provide effective dual AOC2 and AOC3 inhibitors for the treatment of metabolic disorders such as cancer, NASH (non-alcoholic steatohepatitis), pulmonary fibrosis, retinopathy, nephropathy and stroke, in particular hemorrhagic stroke.

A further aim of the present invention is to provide methods for treating a disease or condition mediated by the inhibition of AOC2 and AOC3 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular pyridinyl sulfonamide derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to AOC2 and AOC3.

According to another aspect of the present invention it has been found that the new compounds of general formula (I) as described hereinafter exhibit an inhibiting activity with regard to AOC3.

In a first aspect the present invention provides a compound of general formula wherein
ring A is selected from the group A-G1 consisting of:

$R^1$ is selected from the group $R^1$-G1 consisting of H, F, Cl, Br, CN, —OH, $C_{1-4}$-alkyl, —O—($C_{1-4}$-alkyl), —$(CH_2)_m$—COOH, —$(CH_2)_m$—C(=O)—O—($C_{1-4}$-alkyl), —C(=O)-heterocyclyl, —$(CH_2)_m$—C(=O)—NH$_2$, —$(CH_2)_m$—C(=O)—NH—($C_{1-4}$-alkyl), —$(CH_2)_m$—C(=O)—N($C_{1-4}$-alkyl)$_2$, —C(=O)—NH—$C_{3-6}$-cycloalkyl, —C(=O)—NH-heterocyclyl, —$(CH_2)_m$—NH—C(=O)—($C_{1-3}$-alkyl), —N($C_{1-3}$-alkyl)-C(=O)—($C_{1-4}$-alkyl), —N($C_{1-3}$-alkyl)-C(=O)—NH$_2$, —NH—C(=O)—NH—($C_{1-4}$-alkyl), heterocyclyl and phenyl, wherein each alkyl group or sub-group is optionally substituted with 1 or more F atoms or with one OH or —O—($C_{1-3}$-alkyl) group; and wherein each heterocyclyl is selected from the group consisting of azetidinyl, imidazolidinyl, piperidinyl, tetrahydropyranyl and morpholinyl and is optionally substituted with one or two groups independently selected from the group consisting of oxo, $C_{1-3}$-alkyl, —C(=O)—CH$_3$ and —C(=O)-cyclopropyl; and wherein multiple $R^1$ may be identical or different, if n is 2; and n is an integer selected from 1 and 2; and m is an integer selected from 0, 1 and 2; and wherein in any definition mentioned hereinbefore, if not specified otherwise, any alkyl group or sub-group may be straight-chained or branched and is optionally substituted with 1 or more F atoms, a tautomer or stereoisomers thereof,
or a salt thereof,
or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of AOC3 in a patient in need thereof characterized in that a compound of general formula (I) or a pharmaceutically acceptable salt thereof is administered to the patient.

According to another aspect of the invention, there is provided a method for treating cancer, NASH (non-alcoholic steatohepatitis), pulmonary fibrosis, retinopathy, nephropathy or stroke in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described above or hereinafter.

According to another aspect of the invention, there is provided a compound of the general formula (I) or a pharmaceutically acceptable salt thereof for use in a therapeutic method as described above or hereinafter.

In a further aspect this invention relates to a method for treating a disease or condition mediated by the inhibition of AOC3 in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of AOC3.

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly A, $R^1$ and $R^2$, are defined as above and hereinafter. If residues, substituents or groups occur several times in a compound, as for example $R^2$, they may have the same or different meanings. Some preferred meanings of individual groups and substituents of the compounds according to the invention will be given hereinafter. Any and each of these definitions may be combined with each other.

A:

A-G1:

Ring A is preferably selected from the group A-G1 as defined above.

A-G2:

In another embodiment, ring A is selected from the group A-G2 consisting of

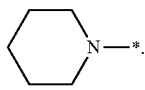

A-G3:

In another embodiment, ring A is selected from the group A-G3 consisting of

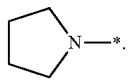

A-G4:

In another embodiment, ring A is selected from the group A-G4 consisting of

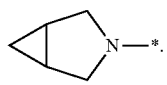

A-G5:

In another embodiment, ring A is selected from the group A-G5 consisting of

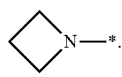

$R^1$-G1:

The group $R^1$ is preferably selected from the group $R^1$-G1 as defined above.

$R^1$-G1a:

In one embodiment the group $R^1$ is selected from the group $R^1$-G1a consisting of: H, F, Cl, —OH, $C_{1-4}$-alkyl, —O—($C_{1-2}$-alkyl), —$(CH_2)_m$—COOH, —$(CH_2)_m$—C(=O)—O—($C_{1-2}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($CH_3$)($C_{1-3}$-alkyl), —C(=O)—NH-cyclopropyl, —C(=O)—NH-heterocyclyl, —$(CH_2)_m$—NH—C(=O)—($C_{1-3}$-alkyl), —N($C_{1-2}$-alkyl)-C(=O)—($C_{1-2}$-alkyl), —N($C_{1-2}$-alkyl)-C(=O)—$NH_2$, —NH—C(=O)—NH—($C_{1-2}$-alkyl), heterocyclyl and phenyl,
  wherein each alkyl group or sub-group is optionally substituted with 1 to 3 F atoms or with one OH or —O—($C_{1-2}$-alkyl) group; and
  wherein each heterocyclyl is selected from the group consisting of azetidinyl, imidazolidinyl, piperidinyl, tetrahydropyranyl and morpholinyl and is optionally substituted with one or two groups independently selected from the group consisting of oxo, $C_{1-2}$-alkyl, —C(=O)—$CH_3$ and —C(=O)-cyclopropyl; and
  wherein m is 0 or 1; and
  wherein multiple $R^1$ may be identical or different, if n is 2.

$R^1$-G1b:

In another embodiment the group $R^1$ is selected from the group $R^1$-G1b consisting of: H, F, —OH, —$CH_3$, —$CF_3$, —O—$CH_3$, —COOH, —$(CH_2)_m$—C(=O)—O—$CH_3$, —$(CH_2)_m$—C(=O)—$NH_2$, —C(=O)—NH—($C_{1-3}$-alkyl), —$(CH_2)$—C(=O)—N($CH_3$)$_2$, —$(CH_2)$—C(=O)—N($CH_3$)($CH_2CH_3$), —C(=O)—NH-cyclopropyl, 1-(cyclopropylcarbonyl)-piperidin-4-yl and 3-methyl-2-oxo-imidazolidin-1-yl,
  wherein each ethyl group or sub-group is optionally substituted in position 2 with one F atom, one OH or one —O—$CH_3$ group; and
  wherein each propyl group or sub-group is optionally substituted in position 2 or 3 with 1 to 3 F atoms; and
  wherein m is 0 or 1; and
  wherein multiple $R^1$ may be identical or different, if n is 2.

If n is 2, the second $R^1$ group of $R^1$-G1, $R^1$-G1a or $R^1$-G1b is preferably selected from the group consisting of F, $CH_3$, $CF_3$ and phenyl.

$R^1$-G2:

In another embodiment the group $R^1$ is selected from the group $R^1$-G2 consisting of: H, F, —OH, $C_{1-4}$-alkyl, —O—($C_{1-4}$-alkyl), —$(CH_2)_m$—COOH, —$(CH_2)_m$—C(=O)—O—($C_{1-4}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-4}$-alkyl)$_2$, —C(=O)—NH—$C_{3-6}$-cycloalkyl, —C(=O)—NH-heterocyclyl, —$(CH_2)_m$—NH—C(=O)—($C_{1-3}$-alkyl), —N($C_{1-3}$-alkyl)-C(=O)—($C_{1-4}$-alkyl), —N($C_{1-3}$-alkyl)-C(=O)—$NH_2$, —NH—C(=O)—NH—($C_{1-4}$-alkyl), heterocyclyl and phenyl,
  wherein each alkyl group or sub-group is optionally substituted with 1 or more F atoms or with one OH or —O—($C_{1-3}$-alkyl) group; and
  wherein each heterocyclyl is selected from the group consisting of azetidinyl, imidazolidinyl, piperidinyl, tetrahydropyranyl and morpholinyl and is optionally substituted with one or two groups independently selected from the group consisting of oxo, $C_{1-3}$-alkyl, —C(=O)—$CH_3$ and —C(=O)-cyclopropyl; and wherein multiple $R^1$ may be identical or different, if n is 2.

$R^1$-G2a:

In another embodiment the group $R^1$ is selected from the group $R^1$-G2a consisting of: H, —OH, $C_{1-2}$-alkyl, —O—($C_{1-2}$-alkyl), —$(CH_2)_m$—COOH, —$(CH_2)_m$—C(=O)—O—($C_{1-2}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-2}$-alkyl)$_2$, —C(=O)—NH—$C_{3-6}$-cyclopropyl, —C(=O)—NH-heterocyclyl, —$(CH_2)_m$—NH—C(=O)—($C_{1-3}$-alkyl), —N($CH_3$)—C(=O)—($C_{1-2}$-alkyl), —N($CH_3$)—C(=O)—$NH_2$, —NH—C(=O)—NH—($C_{1-3}$-alkyl), heterocyclyl and phenyl, wherein each alkyl group or sub-group is optionally substituted with 1 to 3 F atoms or with one OH or —O—$CH_3$ group; and wherein each heterocyclyl is selected from the group consisting of azetidinyl, imidazolidinyl, tetrahydropyranyl and morpholinyl and is optionally substituted with one or two groups independently selected from the group consisting of oxo, $C_{1-3}$-alkyl and —C(=O)—$CH_3$; and wherein multiple $R^1$ may be identical or different, if n is 2.

$R^1$-G2b:

In another embodiment the group $R^1$ is selected from the group $R^1$-G2b consisting of: H, —OH, $C_{1-2}$-alkyl, —O—$CH_3$, —$(CH_2)_m$—COOH, —$(CH_2)_m$—C(=O)—O—$CH_3$, —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($CH_3$)$_2$, —C(=O)—NH—$C_{3-6}$-cyclopropyl, —C(=O)—NH-tetrahydropyranyl, —$(CH_2)_m$—NH—C(=O)—($C_{1-2}$-alkyl), —N($CH_3$)—C(=O)—$CH_3$, —N($CH_3$)—C(=O)—$NH_2$, —NH—C(=O)—NH—$CH_3$, imidazolidinyl and phenyl, wherein each alkyl group or sub-group is optionally substituted with 1 to 3 F atoms or with one OH group; and wherein the imidazolidinyl group optionally substituted with one or two groups independently selected from the group consisting of oxo and $CH_3$, and wherein each heterocyclyl is selected from the group consisting of azetidinyl and morpholinyl and is optionally substituted with one $CH_3$; and wherein m is 0 or 1; and wherein multiple $R^1$ may be identical or different, if n is 2.

Groups $R^1$-G2, $R^1$-G2a and $R^1$-G2b are preferably combined with group A-G2. If n is 2, the second $R^1$ group of $R^1$-G2, $R^1$-G2a or $R^1$-G2b is preferably selected from the group consisting of $CH_3$, $CF_3$ and phenyl.

$R^1$-G3:

In another embodiment the group $R^1$ is selected from the group $R^1$-G3 consisting of: H, F, Cl, —OH, —O—($C_{1-4}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-4}$-alkyl)$_2$, —$(CH_2)_m$—NH—C(=O)—($C_{1-3}$-alkyl) and —N($C_{1-3}$-alkyl)-C(=O)—($C_{1-4}$-alkyl), wherein each alkyl group or sub-group is optionally substituted with 1 or more F atoms or with one OH or —O—($C_{1-3}$-alkyl) group; and wherein each heterocyclyl is selected from the group consisting of azetidinyl, imidazolidinyl, piperidinyl, tetrahydropyranyl and morpholinyl and is optionally substituted with one oxo or $C_{1-3}$-alkyl group; and wherein multiple $R^1$ may be identical or different, if n is 2.

$R^1$-G3a:

In another embodiment the group $R^1$ is selected from the group $R^1$-G3a consisting of: H, F, —OH, —O—($C_{1-2}$-alkyl), —C(=O)-morpholinyl, —C(=O)—$NH_2$, —C(=O)—NH—($C_{1-4}$-alkyl), —C(=O)—N($C_{1-3}$-alkyl)$_2$, —NH—C(=O)—($C_{1-2}$-alkyl) and —N($CH_3$)—C(=O)—($C_{1-2}$-alkyl), wherein each alkyl group or sub-group is optionally substituted with 1 to 3 F atoms or with one OH or —O—($C_{1-3}$-alkyl) group; and wherein multiple $R^1$ may be identical or different, if n is 2.

$R^1$-G3b:

In another embodiment the group $R^1$ is selected from the group $R^1$-G3b consisting of: H, F, —OH, —O—$CH_3$, —C(=O)-morpholinyl, —C(=O)—$NH_2$, —C(=O)—NH—($C_{1-4}$-alkyl), —C(=O)—N($CH_3$)$_2$ and —NH—C(=O)—($CH_3$), wherein each alkyl group or sub-group is optionally substituted with one OH group; and wherein multiple $R^1$ may be identical or different, if n is 2.

Groups $R^1$-G3, $R^1$-G3a and $R^1$-G3b are preferably combined with group A-G3. If n is 2, the second $R^1$ group of $R^1$-G3, $R^1$-G3a or $R^1$-G3b is preferably F.

$R^1$-G4:

In another embodiment the group $R^1$ is selected from the group $R^1$-G4 consisting of: H, —$(CH_2)_m$—COOH, —$(CH_2)_m$—C(=O)—O—($C_{1-4}$-alkyl), —C(=O)-heterocyclyl, —$(CH_2)_m$—C(=O)—$NH_2$, —$(CH_2)_m$—C(=O)—NH—($C_{1-4}$-alkyl) and —$(CH_2)_m$—C(=O)—N($C_{1-4}$-alkyl)$_2$, wherein each alkyl group or sub-group is optionally substituted with 1 or more F atoms or with one OH or —O—($C_{1-3}$-alkyl) group; and wherein each heterocyclyl is selected from the group consisting of azetidinyl, imidazolidinyl, piperidinyl, tetrahydropyranyl and morpholinyl and is optionally substituted with one oxo or $C_{1-3}$-alkyl group; and wherein multiple $R^1$ may be identical or different, if n is 2.

$R^1$-G4a:

In another embodiment the group $R^1$ is selected from the group $R^1$-G4a consisting of: H, —COOH, —C(=O)—O—($C_{1-2}$-alkyl), —C(=O)-morpholinyl, —C(=O)—$NH_2$, —C(=O)—NH—($C_{1-4}$-alkyl) and —C(=O)—N($C_{1-4}$-alkyl)$_2$, wherein each alkyl group or sub-group is optionally substituted with 1 to 3 F atoms or with one OH or —O—($C_{1-3}$-alkyl) group; and wherein multiple $R^1$ may be identical or different, if n is 2.

$R^1$-G4b:

In another embodiment the group $R^1$ is selected from the group $R^1$-G4b consisting of: H, —COOH, —C(=O)—O—$CH_3$, —C(=O)-morpholinyl, —C(=O)—$NH_2$, —C(=O)—NH—($C_{1-4}$-alkyl) and —C(=O)—N($CH_3$)($C_{1-4}$-alkyl), wherein each alkyl group or sub-group is optionally substituted with one —O—$CH_3$ group.

Groups $R^1$-G4, $R^1$-G4a and $R^1$-G4b are preferably combined with group A-G4. If A is selected from A-G4, n is preferably 1.

$R^1$-G5:

In one embodiment the group $R^1$ is selected from the group $R^1$-G5 consisting of: H, F, Cl, Br, CN, —OH, $C_{1-4}$- alkyl, —O—(C$_{1-4}$-alkyl), —C(=O)—NH$_2$, —C(=O)—NH—(C$_{1-4}$-alkyl), —C(=O)—N(C$_{1-4}$-alkyl)$_2$ and heterocyclyl,
  wherein each alkyl group or sub-group is optionally substituted with 1 or more F atoms or with one OH or —O—(C$_{1-3}$-alkyl) group; and
  wherein each heterocyclyl is selected from the group consisting of azetidinyl and piperidinyl, and is optionally substituted with one C$_{1-3}$-alkyl, —C(=O)—CH$_3$ or —C(=O)-cyclopropyl group; and
  wherein multiple R$^1$ may be identical or different, if n is 2.

R$^1$-G5a:
In another embodiment the group R$^1$ is selected from the group R$^1$-G5a consisting of: H, F, —OH, C$_{1-4}$-alkyl, —O—(C$_{1-2}$-alkyl), —C(=O)—NH$_2$, —C(=O)—NH—(C$_{1-2}$-alkyl), —C(=O)—N(C$_{1-2}$-alkyl)$_2$ and piperidinyl,
  wherein each alkyl group or sub-group is optionally substituted with 1 to 3 F atoms or with one OH group; and
  wherein the piperidinyl group is optionally substituted with one —C(=O)—CH$_3$ or —C(=O)-cyclopropyl group; and
  wherein multiple R$^1$ may be identical or different, if n is 2.

R$^1$-G5b:
In another embodiment the group R$^1$ is selected from the group R$^1$-G5b consisting of: H, F, —OH, C$_{1-4}$-alkyl, —O—CH$_3$, —C(=O)—NH$_2$, —C(=O)—NH—(CH$_3$), —C(=O)—N(CH$_3$)$_2$ and piperidinyl,
  wherein each alkyl group or sub-group is optionally substituted with one OH group; and
  wherein the piperidinyl group is optionally substituted with one —C(=O)-cyclopropyl group; and
  wherein multiple R$^1$ may be identical or different, if n is 2.

Groups R$^1$-G5, R$^1$-G5a and R$^1$-G5b are preferably combined with group A-G5. If n is 2, the second R$^1$ group of R$^1$-G5, R$^1$-G5a or R$^1$-G5b is preferably selected from the group consisting of F and CH$_3$.

n
In one embodiment, n is an integer selected from 1 and 2.
Preferably, n is 1.
In another embodiment, n is 2.

m
In one embodiment, m is an integer selected from 0, 1 and 2.
Preferably, m is 0 or 1.
In another embodiment, m is 0.
In still another embodiment, m is 1.

The following preferred embodiments of compounds of formula I are described using generic formulae I.1 to I.4, wherein any tautomers, solvates, hydrates and salts thereof, in particular the pharmaceutically acceptable salts thereof, are encompassed.

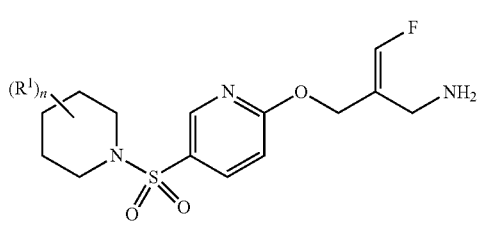

I.1

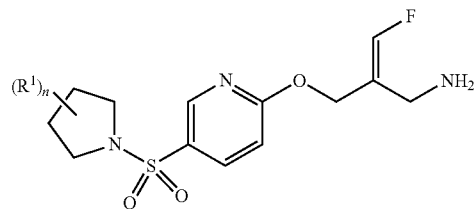

I.2

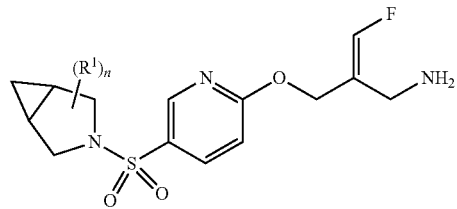

I.3

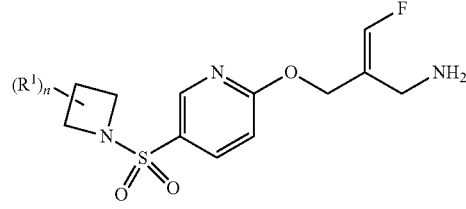

I.4

In of the above formulae (I.1) to (I.4), n and the group R$^1$ are as defined above.

Examples of preferred subgeneric embodiments (E) according to the present invention are set forth in the following table, wherein each substituent group of each embodiment is defined according to the definitions set forth above:

| Embodiment | Formula | A | R$^1$ | n |
|---|---|---|---|---|
| E1 | I | A-G1 | R$^1$-G1 | 1 or 2 |
| E2 | I | A-G1 | R$^1$-G1 | 1 |
| E3 | I | A-G1 | R$^1$-G1a | 1 or 2 |
| E4 | I | A-G1 | R$^1$-G1a | 1 |
| E5 | I | A-G1 | R$^1$-G1b | 1 or 2 |
| E6 | I | A-G1 | R$^1$-G1b | 1 |
| E7 | I | A-G2 | R$^1$-G2 | 1 or 2 |
| E8 | I | A-G2 | R$^1$-G2 | 1 |
| E9 | I | A-G2 | R$^1$-G2a | 1 or 2 |
| E10 | I | A-G2 | R$^1$-G2a | 1 |
| E11 | I | A-G2 | R$^1$-G2b | 1 or 2 |
| E12 | I | A-G2 | R$^1$-G2b | 1 |
| E13 | I | A-G3 | R$^1$-G3 | 1 or 2 |
| E14 | I | A-G3 | R$^1$-G3 | 1 |
| E15 | I | A-G3 | R$^1$-G3a | 1 or 2 |
| E16 | I | A-G3 | R$^1$-G3a | 1 |
| E17 | I | A-G3 | R$^1$-G3b | 1 or 2 |
| E18 | I | A-G3 | R$^1$-G3b | 1 |
| E19 | I | A-G4 | R$^1$-G4 | 1 or 2 |
| E20 | I | A-G4 | R$^1$-G4 | 1 |
| E21 | I | A-G4 | R$^1$-G4a | 1 or 2 |
| E22 | I | A-G4 | R$^1$-G4a | 1 |
| E23 | I | A-G4 | R$^1$-G4b | 1 |
| E24 | I | A-G5 | R$^1$-G5 | 1 or 2 |
| E25 | I | A-G5 | R$^1$-G5 | 1 |
| E26 | I | A-G5 | R$^1$-G5a | 1 or 2 |
| E27 | I | A-G5 | R$^1$-G5a | 1 |
| E28 | I | A-G5 | R$^1$-G5b | 1 or 2 |
| E29 | I | A-G5 | R$^1$-G5b | 1 |

Preferred compounds of the invention include:

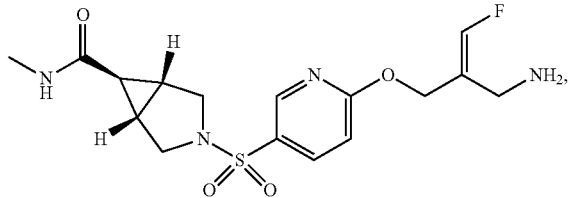

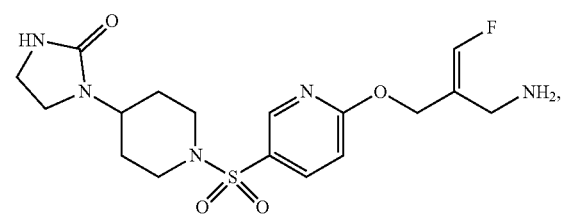

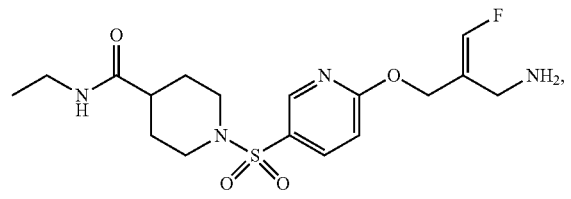

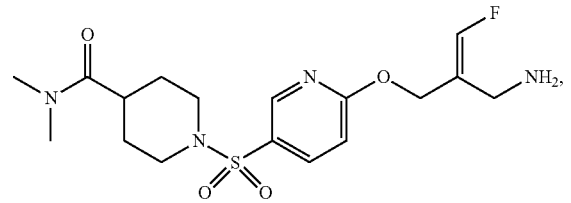

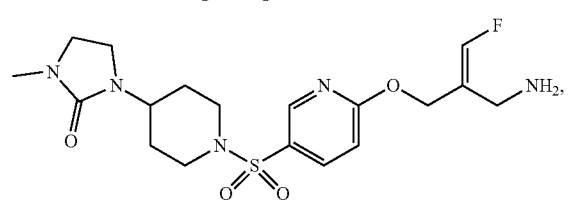

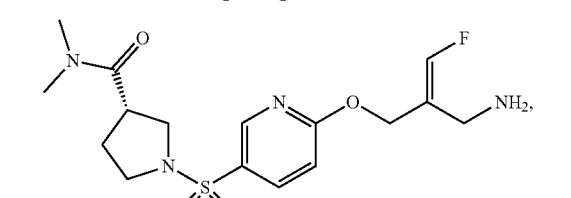

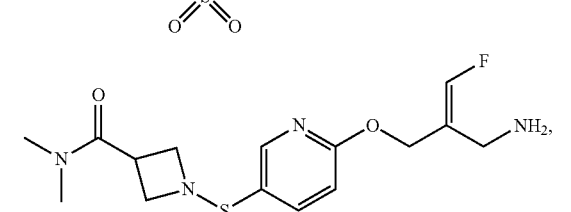

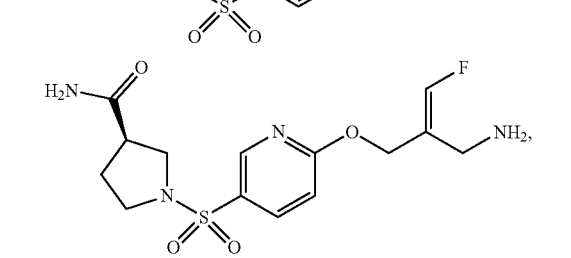

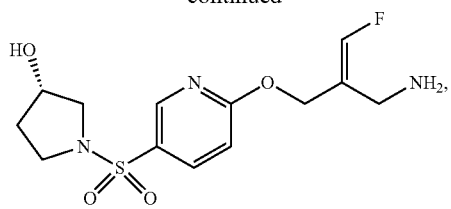

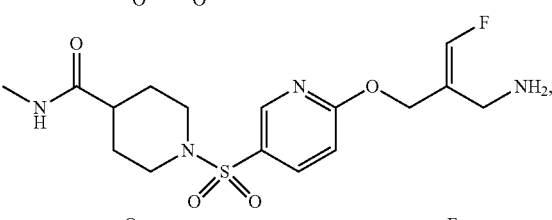

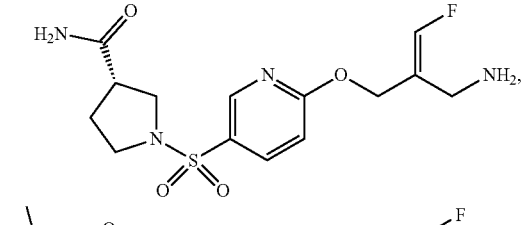

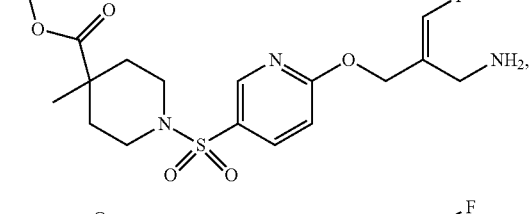

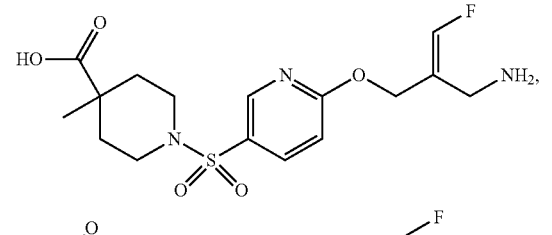

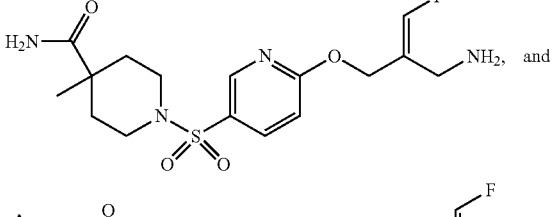

and the salts thereof, preferably the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

Notwithstanding the above, the compounds of the invention are always E-configured in the vinyl fluoride moiety.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of AOC3 with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

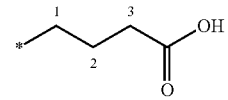

wherein the carboxy group is attached to the third carbon atom of the propyl group. The terms "1-methylpropyl-", "2,2-dimethylpropyl-" or "cyclopropylmethyl-" group represent the following groups:

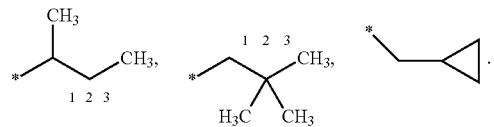

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound. Notwithstanding the above, the compounds of the invention are always E-configured in the vinyl fluoride moiety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_1$-n-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH$($CH_3$)—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

All rests and substituents as defined hereinbefore and hereinafter may be substituted with one or more F atoms.

Pharmacological Activity

The activity of the compounds of the invention may be demonstrated using the following AOC3 assay:

AOC3 Biochemical Assay

The MAO-Glo™ Assay (commercially available from PROMEGA, #V1402) provides a sensitive method for the measurement of monoamine oxidase (MAO) activity (Valley, M. P. et al., 2006, Anal. Biochem. 359: 238-246) from a variety of tissues, biofluids or recombinant expressed or purified enzymes. As substrate a derivate of the beetle luciferin ((4S)-4,5-dihydro-2-(6-hydroxybenzothiazolyl)-4-thiazole-carboxylic acid) is used, which is oxidized at a primary amine moiety. After a spontaneous elimination and a catalyzed esterase reaction, the turnover of the luciferine by the luciferase is recorded as a signal of AOC3 activity.

For the determination of AOC3 activity or compound inhibition potency, the compound inhibitors are dissolved in DMSO and adjusted to the respective assay concentration with reaction buffer (50 mM HEPES, 5 mM KCl, 2 mM $CaCl_2$, 1.4 mM $MgCl_2$, 120 mM NaCl, 0.001% (v/v) Tween 20, 100 µM TCEP, pH 7.4). An aliquot of 3 µL of the compound dilution is added to a 384 well plate (Optiplate, PS, flat bottom, white, PERKIN ELMER, #6007290) with a final DMSO concentration of 6.6%. Recombinant CHO cells, overexpressing the human (1500 cells/well), mouse (1000 cells/well) or rat (500 cells/well) AOC3 enzyme are diluted in reaction buffer and added in a volume of 15 µL to the wells. After incubation for 20 minutes at 37° C., 2 µL of MAO substrate (dissolved in DMSO at 16 mM, adjusted to assay concentration in reaction buffer to a final assay concentration of 20 µM) is added and further incubated for 60 minutes at 37° C. The turnover of the substrate is determined by the addition of 20 µL of the detection-mix which was generated by the addition of reconstitution buffer with esterase (PROMEGA, #V1402) to the luciferine detection reagent (PROMEGA, #V1402). After an incubation period of 20 minutes, the luminescent signal is measured with Envision 2104 Multilabel Reader (PERKIN ELMER).

Alternative assays for the determination of the AOC3 enzymatic activity could be the extraction of $^{14}$C-labelled benzylamine reaction product or the Amplex Red Monoamine Oxidase reaction (Molecular Probes, Netherlands) as described in Gella et al. (Gella, A. et al., 2013, J. Neural Transm. 120: 1015-1018).

The compounds of general formula (I) according to the invention for example have $IC_{50}$ values below 5000 nM, particularly below 1000 nM, preferably below 300 nM, most preferably below 100 nM.

AOC2 Biochemical Assay

The Amplex® Red Assay (commercially available from Thermo Fisher Scientific) provides a sensitive method for the detection of $H_2O_2$ generated during enzymatic reactions like the amine oxidation catalyzed by AOC2. The assay reagent is a colorless substrate (N-acetyl-3,7-dihydroxyphenoxazine) that reacts in a 1:1 stoichiometry with hydrogen peroxide (H2O2) to produce the fluorescent dye resorufin (7-hydroxyphenoxazin-3-one, excitation/emission maxima=570/585 nm). For the determination of AOC2 activity or compound AOC2 inhibition potency, the compound inhibitors are dissolved in DMSO and adjusted to the respective 20× assay concentration with reaction buffer (100 mM sodiumphosphate, 0.05% Pluronic F-127 (#P3000MP Sigma-Aldrich, pH 7.4). An aliquot of 5 µL of the compound dilution is added to a 96 well plate (flat bottom F, black, GREINER bio-one, #655900) in a DMSO concentration of 2%.

An AOC2 enzyme containing cell homogenate is generated by transient transfection of 6×106 HEK293 cells per flask (T75) with 9 µg pCMV-SPORT6-AOC2 (BC142641rc, #pCS6(BC142641)-seq-TCHS1003-GVO-TRI, BioCat) in 750 µL of EMEM culture medium (#BE12-611F, Lonza) and 33,75 µl Attractene (#301005, Qiagen). Cells are cultured for 3 days in EMEM culture medium containing 10% FCS (#04-00-1A, Biological Industries). After washing twice with ice cold PBS, cells are lysed by mechanic homogenation and cleared supernatants are shock frozen in liquid nitrogen and stored at −80° C.

For the determination of AOC2 enzymatic activity cell lysates are thawed on ice and 1:1 diluted with reaction buffer. An Aliquot of 45 µL is added to the compound dilution and incubated for 30 min at 37° C. The enzymatic reaction is started with the addition of 50 µL of Amplex® Red reaction mix (final assay concentration: 100 mM sodiumphosphate, 120 µM Amplex® Red reagent (#A22177 Molecular Probes), 1.5 U/mL Horseradish Peroxidase (#P8375 Sigma-Aldrich), 2 mM phenylethylamine (#P6513-25G Sigma-Aldrich), 0.05% Pluronic F-127 (#P3000MP Sigma-Aldrich), pH 7.4, 37° C.).

The turnover per time of the substrate is determined directly with a fluorescence reader (Ex 540 nm/Em 590 nm) like Envision 2104 Multilabel Reader (PERKIN ELMER) for 60 min.

(cf. Anal Biochem (1997) 253:169-174; Anal Biochem (1997) 253:162-168)

AOC1 Biochemical Assay

The Amplex® Red Assay (available from Thermo Fisher Scientific) provides a sensitive method for the detection of $H_2O_2$ generated during enzymatic reactions like the amine oxidation catalyzed by AOC1. The assay reagent is a colorless substrate (N-acetyl-3,7-dihydroxyphenoxazine) that reacts in a 1:1 stoichiometry with hydrogen peroxide ($H_2O_2$) to produce the fluorescent dye resorufin (7-hydroxyphenoxazin-3-one, excitation/emission maxima=570/585 nm).

For the determination of AOC1 activity or compound AOC1 inhibition potency, the compound inhibitors are dissolved in DMSO and adjusted to the respective assay concentration with reaction buffer (100 mM sodiumphosphate, 0.05% Pluronic F-127 (#P3000MP Sigma-Aldrich), pH 7.4). An aliquot of 3 µL of the compound dilution is added to a 384 well plate (Optiplate, PS, flat bottom F, black, PERKIN ELMER, #6007270) in a DMSO concentration of 6.6%.

An AOC1 enzyme aliquot (#8297-AO-010, R&D Systems) is thawed on ice, diluted in reaction buffer and added in a volume of 7 µL to the wells to give a final assay concentration of 1 ng/well. After incubation of inhibitor and enzyme for 30 minutes at 37° C., the enzymatic reaction is started with the addition of 10 µL of Amplex® Red reaction mix (final assay concentration: 100 mM sodiumphosphate, 120 µM Amplex® Red reagent (#A22177 Molecular Probes), 1.5 U/mL Horseradish Peroxidase (#P8375 Sigma-Aldrich), 200 µM putrescine (#P7505 Sigma-Alrdich), 0.05% Pluronic F-127 (#P3000MP Sigma-Aldrich), pH 7.4, 37° C.).

After an incubation for 30 minutes at 37° C. the turnover of the substrate is determined directly (or after the addition of an excess of an amine-oxidase inhibitor) with a fluorescence reader (Ex 540 nm/Em 590 nm) like Envision 2104 Multilabel Reader (PERKIN ELMER).

In the following table the activity expressed as $IC_{50}$ (nM) of compounds according to the invention is presented wherein the $IC_{50}$ values are determined in the AOC3, AOC2 and AOC1 assays as described hereinbefore. The term "Example" refers to the example numbers according to the following experimental section.

Biological data of the compounds of the present invention as obtained in the AOC3, AOC2 and AOC1 assays.

| Example | AOC3 $IC_{50}$ | AOC2 $IC_{50}$ | AOC1 $IC_{50}$ |
|---|---|---|---|
| 01 | 12 nM | 162 nM | 43370 nM |
| 02 | 33 nM | 1139 nM | >49992 nM |
| 03 | 25 nM | 1022 nM | 23641 nM |
| 04 | 49 nM | 806 nM | >50000 nM |
| 05 | 73 nM | 629 nM | >50000 nM |
| 06 | 61 nM | 593 nM | >50000 nM |
| 07 | 37 nM | 531 nM | >50000 nM |
| 08 | 37 nM | 524 nM | >50000 nM |
| 09 | 39 nM | 489 nM | 6174 nM |
| 10 | 52 nM | 407 nM | >50000 nM |
| 11 | 12 nM | 401 nM | >49954 nM |
| 12 | 38 nM | 385 nM | >49980 nM |
| 13 | 43 nM | 358 nM | >50000 nM |
| 14 | 41 nM | 306 nM | 14255 nM |
| 15 | 38 nM | 263 nM | >50000 nM |
| 16 | 30 nM | 262 nM | >50000 nM |
| 17 | 8 nM | 251 nM | >50000 nM |
| 18 | 37 nM | 244 nM | >50000 nM |
| 19 | 32 nM | 214 nM | >50000 nM |
| 20 | 54 nM | 192 nM | >50000 nM |
| 21 | 20 nM | 190 nM | >49974 nM |
| 22 | 11 nM | 188 nM | >50000 nM |
| 23 | 62 nM | 180 nM | >50000 nM |
| 24 | 28 nM | 165 nM | >50000 nM |
| 25 | 36 nM | 164 nM | 26661 nM |
| 26 | 45 nM | 164 nM | >50000 nM |
| 27 | 51 nM | 160 nM | >50000 nM |
| 28 | 42 nM | 158 nM | >49948 nM |
| 29 | 36 nM | 151 nM | >49966 nM |
| 30 | 46 nM | 126 nM | 11387 nM |
| 31 | 21 nM | 121 nM | >49970 nM |
| 32 | 17 nM | 73 nM | 39500 nM |
| 33 | 15 nM | 49 nM | 33032 nM |
| 34 | 14 nM | 14 nM | 15847 nM |
| 35 | 38 nM | 207 nM | >50000 nM |
| 36 | 67 nM | 551 nM | >50000 nM |
| 37 | 15 nM | 451 nM | 22572 nM |
| 38 | 13 nM | 278 nM | >49976 nM |
| 39 | 19 nM | 262 nM | 16975 nM |
| 40 | 26 nM | 125 nM | >50000 nM |
| 41 | 5 nM | 123 nM | 25390 nM |
| 42 | 20 nM | 87 nM | >49973 nM |
| 43 | 16 nM | 69 nM | 36481 nM |
| 44 | 14 nM | 574 nM | >50000 nM |
| 45 | 10 nM | 307 nM | 11399 nM |
| 46 | 10 nM | 234 nM | >49993 nM |
| 47 | 5 nM | 144 nM | 23169 nM |
| 48 | 24 nM | 67 nM | 1485 nM |
| 49 | 21 nM | 50 nM | >50000 nM |
| 50 | 20 nM | 24 nM | >50000 nM |
| 51 | 13 nM | 325 nM | 48005 nM |
| 52 | 9 nM | 315 nM | 41750 nM |
| 53 | 15 nM | 19 nM | >50000 nM |
| 54 | 308 nM | 4 nM | >50000 nM |
| 55 | 391 nM | 50 nM | >49957 nM |
| 56 | 89 nM | 34 nM | 34674 nM |
| 57 | 2690 nM | 6 nM | >50000 nM |
| 58 | 114 nM | 363 nM | >49945 nM |
| 59 | 18 nM | nd | 27250 nM |
| 60 | 21 nM | 92 nM | >50000 nM |
| 61 | 26 nM | 61 nM | >50000 nM |
| 62 | 18 nM | nd | >50000 nM |
| 63 | 19 nM | nd | >50000 nM |
| 64 | 17 nM | nd | >50000 nM |
| 65 | 11 nM | nd | >50000 nM |
| 66 | 23 nM | nd | 31003 nM | nd = not determined.

According to AOC2 enzymatic tissue activity, the only human tissue with high AOC2-like activity is the retina and expression is associated to the retinal capillaries as shown by immune-histological studies. According to enzymatic function and localization of expression, AOC2 physiological function can be reminiscent of the AOC3 homolog which is described as relevant for e.g. neurovascular, retinal inflammation and recruitment of immune cells (Matsuda et al. Invest Ophthalmol Vis Sci. 2017, 58(7): 3254-3261, Noda et al FASEB J. 2008, 4: 1094-103). Data on pharmacological inhibition or genetic depletion of AOC2 is not available so far and it is therefore difficult to estimate the contribution of AOC2 to retinal-vascular inflammation.

Nonetheless, as compared to AOC3 inhibition alone, a combined inhibition of AOC2 and AOC3 might increase anti-inflammatory potency in man, in particular for the treatment of ocular diseases.

Therefore, it was an aim of the invention to provide compounds with a high activity on AOC3 and AOC2, in order to achieve the desired pharmacological effects.

It has now been found out that, surprisingly, the compounds according to the present invention are more active inhibitors of AOC2 than the corresponding prior art compounds as e.g. described in WO 2013/163675 and WO 2018/027892, i.e., the replacement of the phenyl moiety by a pyridinyl moiety and the introduction of azetidinyl-, pyrrolidinyl- or piperidinyl-sulfonylamides results in compounds with an improved inhibitory activity towards AOC2, without affecting the activity towards AOC3.

As it has a secondary amine substituent in the sulfonamide group, compound 14 of WO 2013/163675 represents the structurally closest comparison compound as compared to the presently claimed cyclic amines in the same position. Compound 14 of WO 2013/163675 contains a dimethylamino-sulfonamide moiety as compared to the cyclic azetidinyl-, pyrrolidinyl- or piperidinyl sulfonamides disclosed in the present invention. Additionally, Compound 14 of WO 2013/163675 contains a phenyl group whereas the compounds disclosed in the present invention contain a pyridinyl group. While Compound 14 of WO 2013/163675 is a weak inhibitor of AOC2 ($IC_{50}$=1164 nM, ca. 145-fold higher than $IC_{50}$ against AOC3), the compound of the present invention exhibit an improved inhibitory activity against AOC2 as exemplified by Examples 42, 35, 40 (each only ca. 5-fold less active against AOC2 as compared to AOC3) and 45 (ca. 30-fold less active against AOC2 as compared to AOC3) in the following table.

Reference compounds A and B that structurally differ from examples 42 and 35 of the present invention solely in phenyl versus pyridinyl group can be obtained in analogy to the syntheses described in WO 2013/163675. In comparison, the pyridinyl derivatives of the present invention show an increased inhibitory potency against AOC2. Reference compound A is 22-fold (ratio $IC_{50}$ AOC2/$IC_{50}$ AOC3) less active against AOC2 as compared to AOC3, while the pyridinyl analog Example 42 is only 4-fold less active against AOC2. Reference compound B is 92-fold less active against AOC2 as compared to AOC3, while the pyridinyl analog Example 42 is only 5-fold less active against AOC2.

AOC1 expression and enzymatic activity is mainly found in the gut, placenta and kidney. The enzyme catalyzes the oxidation of primary amines derived from nutrition and protects the individuum from cardiometabolic effects of histamine, putrescine, tryptamine and cadaverine. Inhibition of AOC1 can lead to impaired tolerance to ingested histamine, resulting in increased plasma and tissue histamine-levels which can cause adverse events or undesirable side effects like decreased aterial pressure and compensation by increased heart-rate, tachycardia, headache, flush, urticaria, pruritus, bronchospasm and cardiac arrest (Maintz L. and Novak N. 2007. Am. J. Clin. Nutr. 85: 1185-96). The consequence of AOC1 inhibition in combination with histamine intake has been demonstrated in experiments with pigs: After the application of the AOC1-inhibitor aminoguanidine (100 mg/kg) and gavage of histamine (2 mg/kg) animals experienced increased histamine blood levels accompanied with a drop of blood pressure, increased heart rate, flushing, vomiting and death (3 out of 15 animals) (Sattler J. 1988. Agents and Actions, 23: 361-365) under the experimental conditions. Histamine intolerance in humans was associated to mutations in the promoter region of AOC1, leading to reduced mRNA expression and plasma AOC1 activity (Maintz et al. 2011. Allergy 66: 893-902).

Therefore, it was an aim of the invention to provide compounds with a low activity on AOC1, in order to avoid such undesired side-effects.

It has now been found out that, surprisingly, the compounds of the present invention exhibit increased selectivity towards AOC1 as compared to prior art compounds, particularly to the compounds disclosed in WO 2018/027892. Examples 6, 5 and 2 of WO 2018/027892 differ from examples 35, 40 and 45, respectively, in the pyrimidinyl versus pyridinyl group and in the lack of the sulfonyl group. While Example 6 of WO 2018/027892 and the pyridinyl sulfonyl analog Example 35 of the present invention are similarly potent against AOC3, Example 35 shows a much higher $IC_{50}$ against AOC1. Example 5 of WO 2018/027892 and the racemic pyridinyl sulfonyl analog Example 40 of the present invention are similarly potent against AOC3, however Example 40 shows a much higher $IC_{50}$ against AOC1. In addition, Example 2 of WO 2018/027892 and the pyridinyl sulfonyl analog Example 45 of the present invention are similarly potent against AOC3, however Example 45 shows a much higher $IC_{50}$ against AOC1.

Comparison of biological data of certain compounds as obtained in the AOC3, AOC2 and AOC1 assays as described above.

| Structure | $IC_{50}$ AOC3 | $IC_{50}$ AOC2 | $IC_{50}$ AOC1 |
|---|---|---|---|
| Compound 14 of WO 2013/163675 | 8 nM | 1164 nM | >50000 nM |

-continued
| Structure | IC$_{50}$ AOC3 | IC$_{50}$ AOC2 | IC$_{50}$ AOC1 |
|---|---|---|---|
| 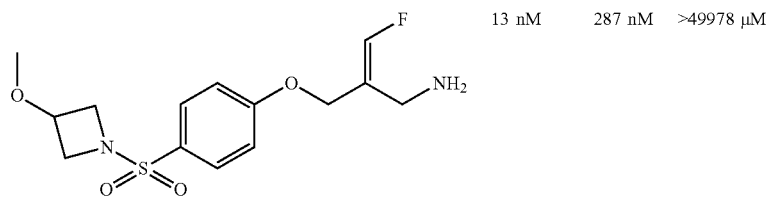<br>Reference compound A | 13 nM | 287 nM | >49978 μM |
| 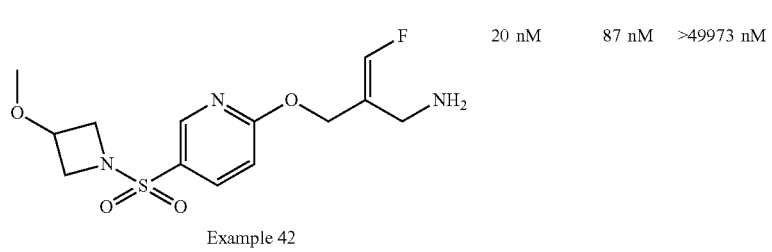<br>Example 42 | 20 nM | 87 nM | >49973 nM |
| 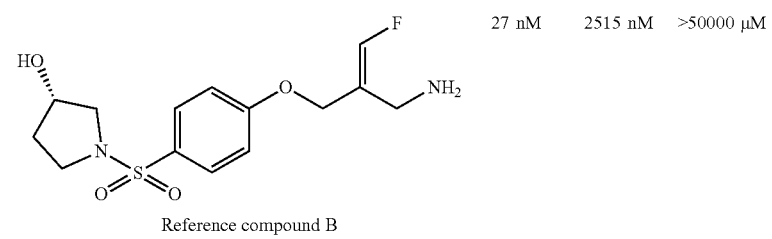<br>Reference compound B | 27 nM | 2515 nM | >50000 μM |
| 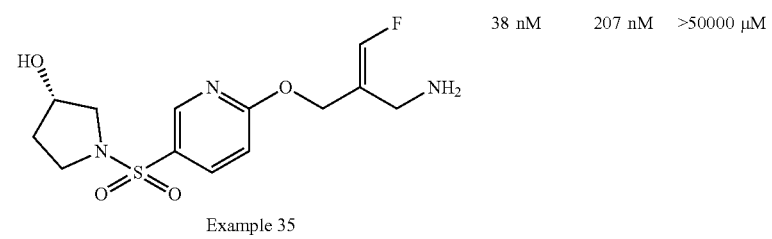<br>Example 35 | 38 nM | 207 nM | >50000 μM |
| 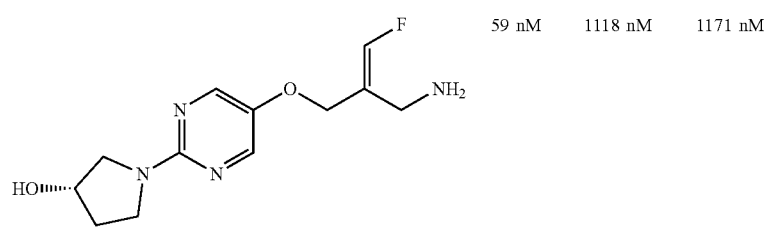<br>Example 6 of WO 2018/027892 | 59 nM | 1118 nM | 1171 nM |
| 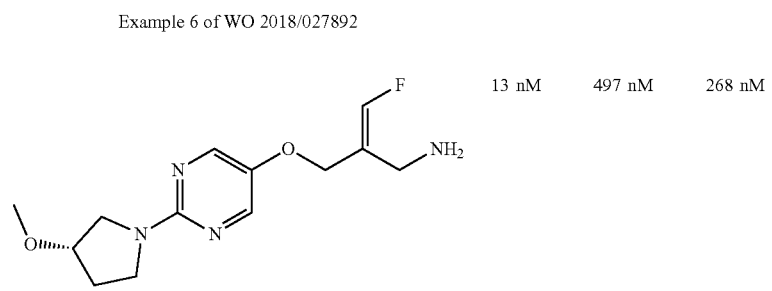<br>Example 5 of WO 2018/027892 | 13 nM | 497 nM | 268 nM |

| Structure | IC$_{50}$ AOC3 | IC$_{50}$ AOC2 | IC$_{50}$ AOC1 |
|---|---|---|---|
| 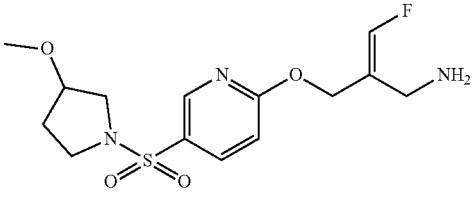<br>Example 40 | 26 nM | 125 nM | >50000 µM |
| 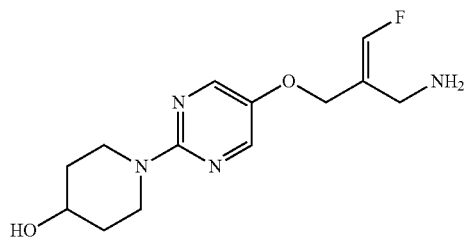<br>Example 2 of WO 2018/027892 | 20 nM | 1085 nM | 269 nM |
| 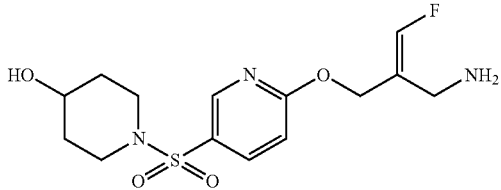<br>Example 45 | 10 nM | 307 nM | 11399 nM |

In view of their ability to inhibit AOC3 and AOC2, the compounds of general formula (I) according to the invention and the corresponding salts thereof are suitable for the treatment, including preventative treatment of all those diseases or conditions which may be affected or which are mediated by the inhibition of AOC3 and AOC2 activity.

Further, compounds of the present invention show moderate to high in vitro efflux and/or a low intrinsic permeability in an MDCK p-GP assay. Therefore, compounds of the present invention are expected to exhibit a lower free concentration in the brain than in the blood (Liu, H. et al., 2018, Drug Discovery Today 23 (7): 1357-1372).

Accordingly, the present invention relates to a compound of general formula (I) as a medicament.

Furthermore, the present invention relates to the use of a compound of general formula (I) for the treatment and/or prevention of diseases or conditions which are mediated by the inhibition of AOC3 in a patient, preferably in a human.

In yet another aspect the present invention relates a method for treating, including preventing a disease or condition mediated by the inhibition of AOC3 in a mammal that includes the step of administering to a patient, preferably a human, in need of such treatment a therapeutically effective amount of a compound of the present invention, or a pharmaceutical composition thereof.

Diseases and conditions mediated by inhibitors of AOC3 embrace cancer, NASH (non-alcoholic steatohepatitis), pulmonary fibrosis, retinopathy, nephropathy and stroke.

According to one aspect the compounds of the present invention are particularly suitable for treating inflammatory diseases, such as vascular inflammatory diseases, arthritis, acute and chronic joint inflammation; eczema, such as atopic eczema, psoriasis ulcerative and rheumatoid psoriasis; pain, particularly musculoskeletal or nociceptive pain; inflammatory bowel disease, particularly non-infectious inflammatory bowel disease; multiple sclerosis; scleroderma, pulmonary diseases such as respiratory distress syndrome, asthma, pulmonary fibrosis, idiopathic pulmonary fibrosis (IPF), chronic obstructive pulmonary disease (COPD) and idiopathic inflammatory disease; nephropathy, diabetic proteinuria, kidney fibrosis; diabetic retinopathy or diabetic oedema such as macular diabetic oedema; cancer, particularly melanoma and lymphoma; hepatocellular carcinoma, unspecified Colitis, rheumatoid Crohn's disease Colitis; biliary tract diseases, primary biliary cholangitis, primary sclerosing cholangitis, non-alcoholic steatohepatitis (NASH), non-alcoholic fatty liver disease (NAFLD), alcoholic liver disease, liver fibrosis, liver cirrhosis; ulcerative reperfusion injury, cerebral ischaemia and transplant rejection.

According to another aspect the compounds of the present invention are particularly suitable for treating inflammatory diseases, such as vascular inflammatory diseases, arthritis and inflammatory bowel disease, particularly non-infectious inflammatory bowel disease; pulmonary fibrosis and idiopathic pulmonary fibrosis; diabetic retinopathy or diabetic oedema such as macular diabetic oedema; unspecified Colitis, rheumatoid Crohn's disease Colitis; biliary tract diseases, primary biliary cholangitis, primary sclerosing cholangitis, non-alcoholic steatohepatitis (NASH), non-alcoholic fatty liver disease (NAFLD), alcoholic liver disease, liver fibrosis, and liver cirrhosis.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon the patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with the metabolic syndrome, diabetes, obesity, cardiovascular diseases, cancer, NASH (non-alcoholic steatohepatitis), pulmonary fibrosis, retinopathy, nephropathy and/or stroke.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, anti-fibrotic agents, agents for the treatment of malignant tumors, antithrombotic agents, anti-angiogenesis agents, agents for the treatment of heart failure and agents for the treatment of complications caused by diabetes or associated with diabetes.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of AOC3, in particular diseases or conditions as described hereinbefore and hereinafter.

In yet another aspect the present invention relates a method for treating, including preventing a disease or condition mediated by the inhibition of AOC3 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Synthesis Schemes

Typical methods of preparing the compounds of the invention are described in the experimental section.

The potent inhibitory effect of the compounds of the invention can be determined by in vitro enzyme assays as described in the experimental section.

The compounds of the present invention may also be made by methods known in the art including those described below and including variations within the skill of the art.

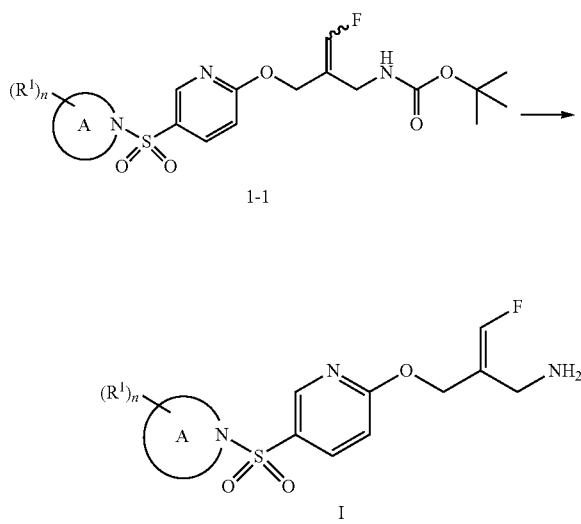

Compounds of the general formula I, wherein A and R¹ are as previously defined, can be prepared via the process outlined in Scheme 1 using a compound of the general formula 1-1. Deprotection of the tert-Butoxycarbonyl (=BOC) group may be effected by treatment with an acid such as hydrochloric acid or trifluoroacetic acid in a suitable solvent such as methanol, dioxane or dichloromethane at a temperature between −20° C. and 100° C. If 1-1 is employed as a mixture of E/Z-isomers, the vinylfluorid E/Z-isomers of compounds of the general formula I may be separated by preparative HPLC or column chromatography on silica gel which affords compounds of the general formula I in isomerically pure form.

Scheme 2

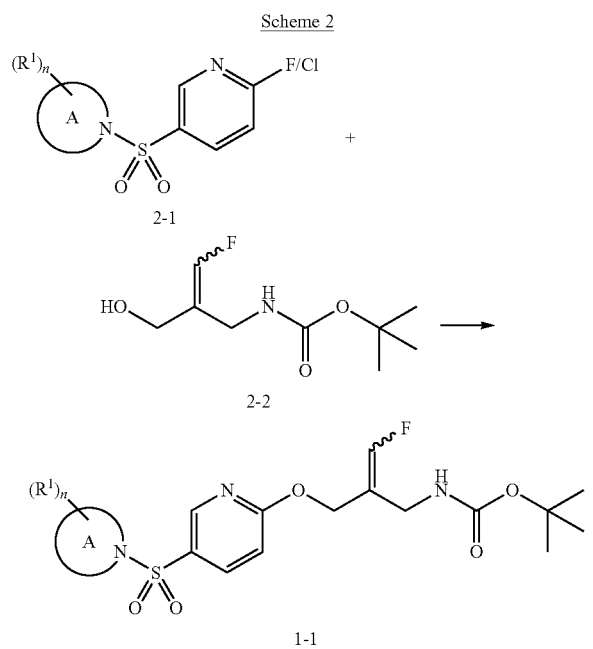

Intermediates of the general formula 1-1, wherein A and R¹ are as previously defined, can be prepared via the process outlined in Scheme 2 using a 6-fluoro or 6-chloro substituted pyridinyl sulfonamide compound of the general formula 2-1, wherein A and R¹ are as previously defined, and the alcohol 2-2 either as pure E-isomer or as an E/Z-mixture, and a base such as sodium tert-butoxide or sodium hydride in an appropriate solvent such as THF, DMSO or toluene at a temperature between −20° C. and 100° C.

Scheme 3

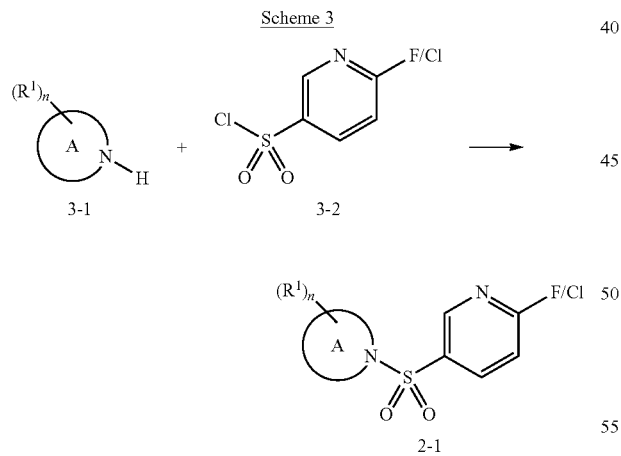

Intermediates of the general formula 2-1, wherein A and R¹ are as previously defined, can be prepared via the process outlined in Scheme 3 using an amine compound of the general formula 3-1, wherein A and R¹ are as previously defined, and 6-fluoro- or 6-chloropyridine-3-sulfonyl chloride, and a base such as triethylamine in an appropriate solvent such as dichloromethane, NMP, THF, DMSO or mixtures thereof at a temperature between −20° C. and 100° C.

Scheme 4

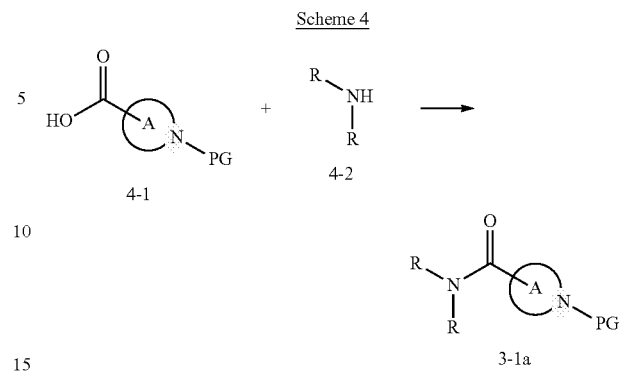

Intermediates of the general formula 3-1a, wherein the amine substituents R are selected as previously defined for amides among substituent R¹, can be prepared via the process outlined in Scheme 4 using a carboxylic acid of the general formula 4-1, a primary or secondary amine of the general formula 4-2, wherein the amine substituents R are selected as previously defined for amides among substituent R¹, an amide coupling reagent such as 1-propanephosphonic acid cyclic anhydride or HATU, and a base such as triethylamine or DIPEA in an appropriate solvent such as THF or DMF at a temperature between −20° C. and 100° C.

Scheme 5

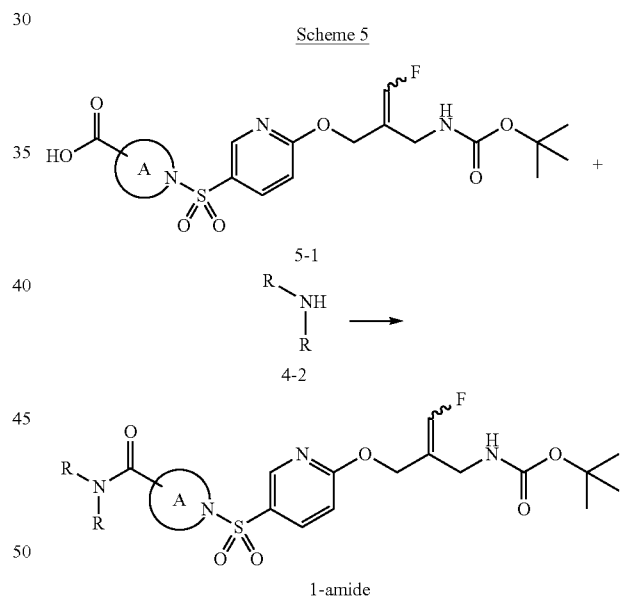

Compounds of the general formula 1-amide which exhibit an amide group according to the definitions for R¹, can also be prepared from carboxylic acids of the general formula 5-1, a primary or secondary amine of the general formula 4-2, wherein the amine substituents R are selected as previously defined for amides among substituent R¹, an amide coupling reagent such as 1-propanephosphonic acid cyclic anhydride, TCFH or HATU, and a base such as triethylamine or DIPEA in an appropriate solvent such as THF or DMF at a temperature between −20° C. and 100° C. Carboxylic acids of the general formula 5-1 are accessible from the corresponding alkyl esters through saponification with sodium or lithium hydroxide in a solvent such as methanol or THF at a temperature between −20° C. and 100° C.

The synthetic routes presented may rely on the use of protecting groups. For example, reactive groups present, such as hydroxy, carbonyl, carboxy, amino, alkylamino or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before.

The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds.

Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

EXPERIMENTAL PART

The Examples that follow are intended to illustrate the present invention without restricting it.

General Definitions

List of Abbreviations

A Acid
ACN Acetonitrile
aq. Aqueous
B Base
BOC tert-Butoxycarbonyl
° C. Degree Celsius
Cbz Benzyloxycarbonyl
d Day
DCM Dichloromethane
DIPEA N,N-Diisopropylethylamine
DMF N,N-Dimethylformamide
DMSO Dimethylsulfoxide
eq Equivalent
ESI-MS Electrospray ionisation mass spectrometry
EtOH Ethanol
EtOAc Ethyl acetate
exc. Excess
g Gramm
h Hour
HATU N,N,N',N'-tetramethyl-O-(7-azabenzotriazol-1-yl) uronium hexafluorophosphate
HPLC High performance liquid chromatography
IBCF Isobutylchloroformate
iPrOH Iso-Propylalcohol
L Liter
M Molar (mol/L)
MeOH Methanol
min Minute
mg milligramm
mL Milliliter
mmol Millimol
MS Mass spectrometry
MTBE 2-Methoxy-2-methylpropane
N Normal=1 molar=1 mol/L
NMP N-methyl-2-pyrrolidinone
NMR Nuclear magnetic resonance
Pd/C Palladium on carbon
psi Pound-force per square inch
RP Reverse phase
RT Room temperature (about 22° C.)
$R_t$ Retention time
S Solvent
Sat. Saturated
T Temperature
t Time
TBTU Benzotriazolyl tetramethyluronium tetrafluoroborate
TCFH Chloro-N,N,N',N'-tetramethylformamidinium hexafluorophosphate
TLC Thin-layer chromatography
TEA Triethylamine
TFA Trifluoroacetic acid
THF Tetrahydrofuran
THP Tetrahydropyran
Tol Toluene General Methods Unless noted otherwise, all reactions are run at room temperature (about 22° C.), under inert atmosphere (e.g., Argon, $N_2$), and under anhydrous conditions. All compounds are characterized by at least one of the following methods: $^1$H NMR, HPLC, HPLC-MS, or melting point.

Typically, reaction progress is monitored by thin layer chromatography (TLC) or HPLC-MS. Intermediates and products are purified using at least one of the following methods:

Recrystallization, column chromatography on silica gel or reversed phase HPLC using a C18 semi-preparative column eluting with a gradient of:
ACN and $H_2O$+0.1% TFA
ACN and $H_2O$+0.1% $NH_4OH$
Analytical Data The reported mass spectrometry (MS) data correspond to the observed mass signals (e.g., [M+H]$^+$). The HPLC methods used to characterize the compounds of the invention is described in the following tables.

HPLC-Methods

| Method | Mobile Phase A | Mobile Phase B | Gradient Time (min) | % A | % B | Flow (mL/min) | Column | Temperature |
|---|---|---|---|---|---|---|---|---|
| HPLC-1 | 0.1% TFA in water | ACN | 0.0 | 99.0 | 1.0 | 1.6 | XBridge BEH C18_2.1 × 30 mm_1.7 µm particle diameter | 60° C. |
| | | | 0.02 | 99.0 | 1.0 | 1.6 | | |
| | | | 1.0 | 0.0 | 100.0 | 1.6 | | |
| | | | 1.1 | 0.0 | 100.0 | 1.6 | | |

| Method | Mobile Phase A | Mobile PhaseB | Gradient Time (min) | % A | % B | Flow (mL/min) | Column | Temperature |
|---|---|---|---|---|---|---|---|---|
| HPLC-2 | 0.1% TFA in water | ACN | 0.0 | 99.0 | 1.0 | 1.5 | Sunfire C18_2.1 × 30 mm_2.5 µm particle diameter | 60° C. |
| | | | 0.02 | 99.0 | 1.0 | 1.5 | | |
| | | | 1.0 | 0.0 | 100.0 | 1.5 | | |
| | | | 1.1 | 0.0 | 100.0 | 1.5 | | |

| Method | Mobile Phase A | Mobile Phase B | Gradient Time (min) | % A | % B | Flow (mL/min) | Column | Temperature |
|---|---|---|---|---|---|---|---|---|
| HPLC-3 | 0.1% TFA in water | ACN | 0.0 | 50.0 | 50.0 | 1.5 | Sunfire C18_2.1 × 30 mm_ 2.5 µm particle diameter | 60° C. |
| | | | 0.02 | 50.0 | 50.0 | 1.5 | | |
| | | | 1.0 | 0.0 | 100.0 | 1.5 | | |
| | | | 1.1 | 0.0 | 100.0 | 1.5 | | |

| Method | Mobile Phase A | Mobile Phase B | Gradient Time (min) | % A | % B | Flow (mL/min) | Column | Temperature |
|---|---|---|---|---|---|---|---|---|
| HPLC-4 | 0.1% NH$_3$ in water | ACN | 0.0 | 97.0 | 3.0 | 2.2 | XBridge C18_3.0 × 30 mm_2.5 µm particle diameter | 60° C. |
| | | | 0.2 | 97.0 | 3.0 | 2.2 | | |
| | | | 1.2 | 0.0 | 100.0 | 2.2 | | |
| | | | 1.25 | 0.0 | 100.0 | 3.0 | | |
| | | | 1.4 | 0.0 | 100.0 | 3.0 | | |

| Method | Mobile Phase A | Mobile Phase B | Gradient Time (min) | % A | % B | Flow (mL/min) | Column | Temperature |
|---|---|---|---|---|---|---|---|---|
| HPLC-5 | 0.1% TFA in water | ACN | 0.0 | 97.0 | 3.0 | 2.2 | XBridge C18_3.0 × 30 mm_2.5 µm particle diameter | 60° C. |
| | | | 0.2 | 97.0 | 3.0 | 2.2 | | |
| | | | 1.2 | 0.0 | 100.0 | 2.2 | | |
| | | | 1.25 | 0.0 | 100.0 | 3.0 | | |
| | | | 1.4 | 0.0 | 100.0 | 3.0 | | |

| Method | Mobile Phase A | Mobile Phase B | Gradient Time (min) | % A | % B | Flow (mL/min) | Column | Temperature |
|---|---|---|---|---|---|---|---|---|
| HPLC-6 | 0.1% TFA in water | ACN | 0.0 | 97.0 | 3.0 | 2.2 | Sunfire C18_3.0 × 30 mm_2.5 µm particle diameter | 60° C. |
| | | | 0.2 | 97.0 | 3.0 | 2.2 | | |
| | | | 1.2 | 0.0 | 100.0 | 2.2 | | |
| | | | 1.25 | 0.0 | 100.0 | 3.0 | | |
| | | | 1.4 | 0.0 | 100.0 | 3.0 | | |

| Method | Mobile Phase A | Mobile Phase B | Gradient Time (min) | % A | % B | Flow (mL/min) | Column | Temperature |
|---|---|---|---|---|---|---|---|---|
| HPLC-7 | 0.1% TFA in water | 0.08% TFA in ACN | 0.0 | 95.0 | 5.0 | 1.5 | Sunfire C18_3.0 × 30 mm_2.5 μm particle diameter | 60° C. |
| | | | 1.3 | 0.0 | 100.0 | 1.5 | | |
| | | | 1.5 | 0.0 | 100.0 | 1.5 | | |
| | | | 1.6 | 95.0 | 5.0 | 1.5 | | |

| Method | Mobile Phase A | Mobile Phase B | Gradient Time (min) | % A | % B | Flow (mL/min) | Column | Temperature |
|---|---|---|---|---|---|---|---|---|
| HPLC-8 | 0.1% NH₃ in water | ACN | 0.0 | 95.0 | 5.0 | 1.5 | XBridge C18_3.0 × 30 mm_2.5 μm particle diameter | 60° C. |
| | | | 1.3 | 0.0 | 100.0 | 1.5 | | |
| | | | 1.5 | 0.0 | 100.0 | 1.5 | | |
| | | | 1.6 | 95.0 | 5.0 | 1.5 | | |

| Method | Mobile Phase A | Mobile Phase B | Gradient Time (min) | % A | % B | Flow (mL/min) | Column | Temperature |
|---|---|---|---|---|---|---|---|---|
| HPLC-9 | 0.1% TFA in water | 0.08% TFA in ACN | 0.0 | 95.0 | 5.0 | 1.5 | Sunfire C18_3.0 × 30 mm_2.5 μm particle diameter | 60° C. |
| | | | 1.3 | 0.0 | 100.0 | 1.5 | | |
| | | | 1.5 | 0.0 | 100.0 | 1.5 | | |
| | | | 1.6 | 95.0 | 5.0 | 1.5 | | |

| Method | Mobile Phase A | Mobile Phase B | Gradient Time (min) | % A | % B | Flow (mL/min) | Column | Temperature |
|---|---|---|---|---|---|---|---|---|
| HPLC-10 | 0.1% TFA in water | ACN | 0.0 | 97.0 | 3.0 | 4.0 | Sunfire C18_3.0 × 30 mm_2.5 μm particle diameter | 60° C. |
| | | | 0.15 | 97.0 | 3.0 | 3.0 | | |
| | | | 2.15 | 0.0 | 100.0 | 3.0 | | |
| | | | 2.2 | 0.0 | 100.0 | 4.5 | | |
| | | | 2.4 | 0.0 | 100.0 | 4.5 | | |

Synthetic Intermediates/Examples

The intermediates and examples which follow are illustrative and, as recognized by one skilled in the art, particular reagents or conditions could be modified as needed for individual compounds without undue experimentation.

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the synthetic section. Undescribed intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

Intermediate I.1: trans-3-Aza-bicyclo[3.1.0]hexane-6-carboxylic acid methylamide hydrogenchlorid

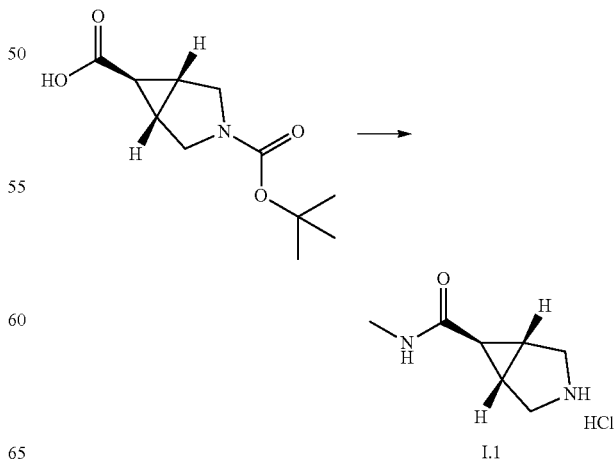

I.1

Step1—Amide-coupling: To the solution of trans-3-aza-bicyclo[3.1.0]hexane-3,6-dicarboxylic acid 3-tert-butyl ester (1.00 g; 4.40 mmol) and TEA (4.94 mL; 35.20 mmol) in THF (5 mL) was added methylamine (2 M in THF; 4.40 mL; 8.80 mmol). The reaction mixture was stirred at RT for 5 min and 1-propanephosphonic acid cyclic anhydride (50% in THF; 5.14 mL; 8.80 mmol) was added. The reaction mixture was stirred at RT for 45 min, diluted with aq. 4 N NaOH (25 mL) and extracted with MTBE (2×25 mL). The pooled organic phases were dried with Na$_2$SO$_4$, filtered and evaporated to dryness.

Step2—BOC deprotection: The crude material of step 1 was taken up in EtOAc (20 mL) and MeOH (20 mL) and hydrogen chloride (4 N in 1,4-dioxane; 5 mL; 20.00 mmol) was added. The reaction mixture was stirred at RT overnight and concentrated under reduced pressure to provide intermediate I.1.

Yield: 882 mg (80%), ESI-MS: m/z=141 [M+H]$^+$, R$_t$ (HPLC): 0.12 min (HPLC-6)

Intermediate I.2: trans-3-Aza-bicyclo[3.1.0]hexane-1-carboxylic acid methylamide hydrochloride

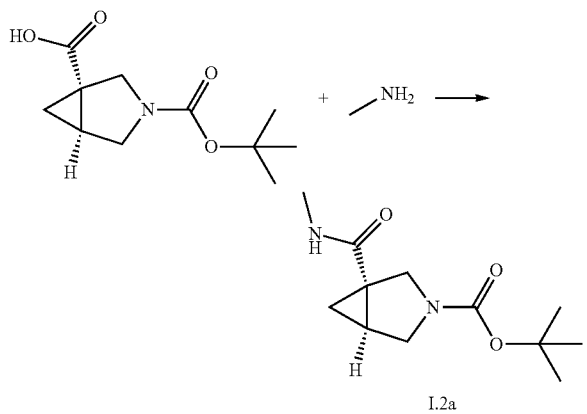

Trans-3-Aza-bicyclo[3.1.0]hexane-1,3-dicarboxylic acid 3-tert-butyl ester (1.00 g; 4.40 mmol) and HATU (1.90 g; 4.84 mmol) were dissolved in DMF (5 mL) and DIPEA (1.89 mL; 11.00 mmol) and stirred at RT for 30 min. To the reaction mixture methylamine (2 M in THF; 4.40 mL; 8.80 mmol) was added and was stirred at RT overnight. The reaction mixture was diluted with water (20 mL) and extracted with DCM (3×20 mL). The pooled organic phases were washed with aq. 1 N NaOH, dried and concentrated under reduced pressure. The residue was purified by RP-HPLC (ACN/water+TFA) to obtain intermediate I.2a.

Yield: 0.95 g (90%), ESI-MS: m/z=185 [M+H]$^+$, R$_t$ (HPLC): 0.87 min (HPLC-6) BOC deprotection:

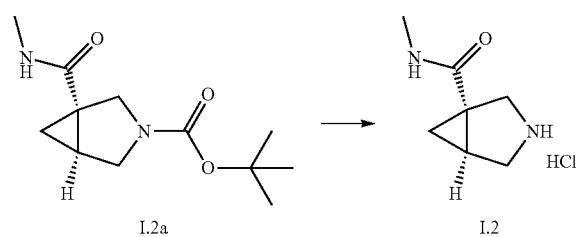

Intermediate I.2a (0.94 mg; 3.89 mmol) was dissolved in MeOH (2 mL) and hydrogen chloride (4 N in 1,4-dioxane; 5.00 mL; 20.00 mmol) was added. The reaction mixture was stirred at RT for 1 h 40 min, then reduced in vacuo and co-evaporated with MeOH to provide intermediate I.2.

Yield: 0.65 g (95%), ESI-MS: m/z=191 [M+H]$^+$, R$_t$ (HPLC): 0.09 min (HPLC-10)

Intermediate I.3: (S)-Pyrrolidine-3-carboxylic acid [2-methyl-2-(tetrahydro-pyran-2-yloxy)-propyl]-amide Amide-Coupling:

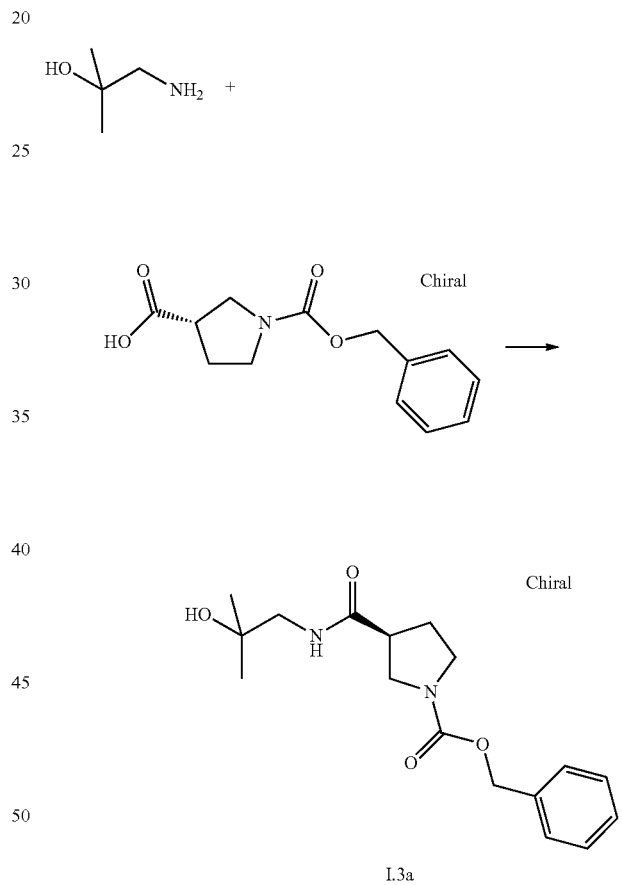

(S)-Pyrrolidine-1,3-dicarboxylic acid-1-benzylester (2.00 g; 8.02 mmol) was dissolved in THF (20.00 mL) and TEA (9.01 mL; 64.19 mmol) and 1-amino-2-methylpropan-2-ol (0.83 g; 8.83 mmol) was added. The reaction mixture was cooled to 0° C. and a solution of 1-propanephosphonic acid cyclic anhydride (50% in THF; 7.03 ml; 12.04 mmol) was added. It was stirred at RT for 3 h. The reaction mixture was diluted with aq. 4 N NaOH (20 mL) and extracted with MTBE (30 mL) twice. The pooled organic phases were dried and evaporated to give the crude intermediate I.3a.

Yield: 2.51 g (98%), ESI-MS: m/z=321 [M+H]$^+$, R$_t$(HPLC): 0.90 min (HPLC-6)

Cbz Deprotection:

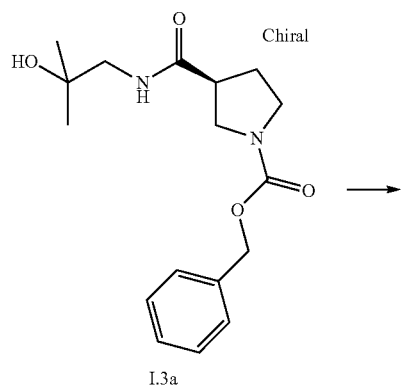

Intermediate I.4: (S)—N-Piperidine-3-yl-acetamide trifluoroacetate

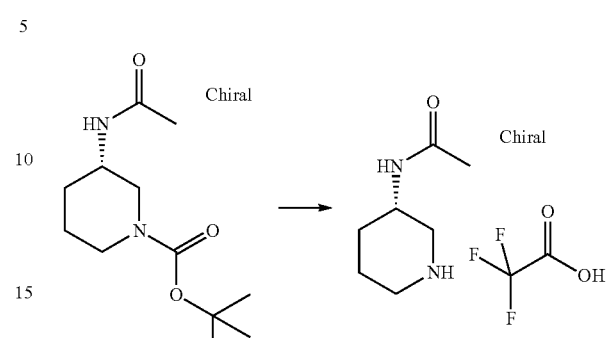

(S)-3-Acetylamino-piperidine-1-carboxylic acid tert-butyl ester (3.00 g; 12.38 mmol), trifluoroacetic acid (9.54 mL; 123.80 mmol) and DCM (80 mL) were stirred at RT overnight. The reaction mixture was evaporated and co-evaporated with EtOH for two times to give intermediate I.4.

Yield: 4.20 g (quant.), ESI-MS: m/z=143 [M+H]$^+$

A mixture of intermediate I.3a (2.51 g; 7.83 mmol) and 10% Pd/C (0.25 g) in MeOH (50 mL) was treated with hydrogen (50 psi) at RT overnight. The reaction mixture was filtered, washed with MeOH and concentrated in vacuo to provide the crude intermediate I.3b.

Yield: 1.47 g (99%), ESI-MS: m/z=187 [M+H]$^+$, R$_t$(HPLC): 0.12 min (HPLC-6)

THP Protection:

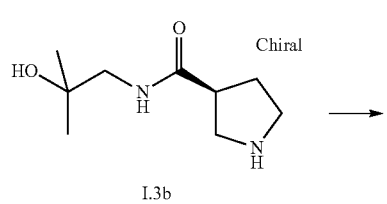

Intermediate I.5:
Morpholin-4-yl-(4-phenyl-piperidin-4-yl)-methanone

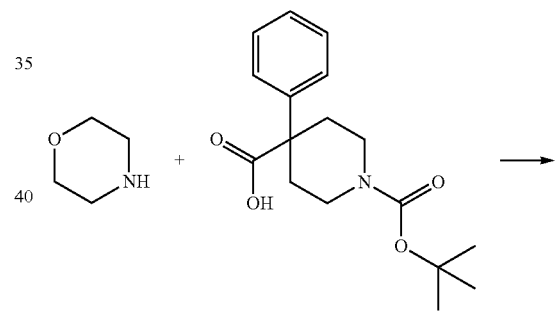

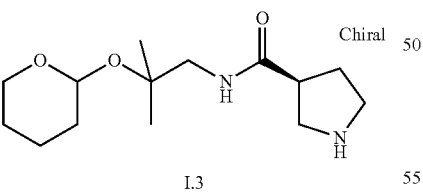

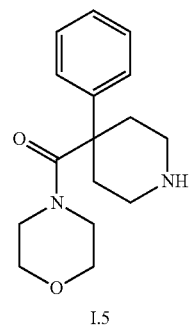

Intermediate I.3b (1.47 g; 7.89 mmol) was diluted with 3,4-dihydro-2H-pyrane (10.00 mL; 108.28 mmol) and p-toluenesulfonic acid monohydrate (0.15 g; 0.79 mmol) was added. The reaction mixture was stirred at RT for three days and concentrated in vacuo to obtain the crude intermediate I.3.

Yield: 2.54 g (99%), ESI-MS: m/z=271 [M+H]$^+$, R$_t$(HPLC): 0.75 min (HPLC-4)

Intermediate I.5 could be prepared according to the procedure described in WO 98/27086, pp. 38-40. Starting materials were morpholine and 4-phenyl-piperidine-1,4-dicarboxylic acid mono-tert-butyl ester.

Intermediate I.6: Azetidin-1-yl-piperidin-4-yl-methanone trifluoroacetate

Amide—Coupling:

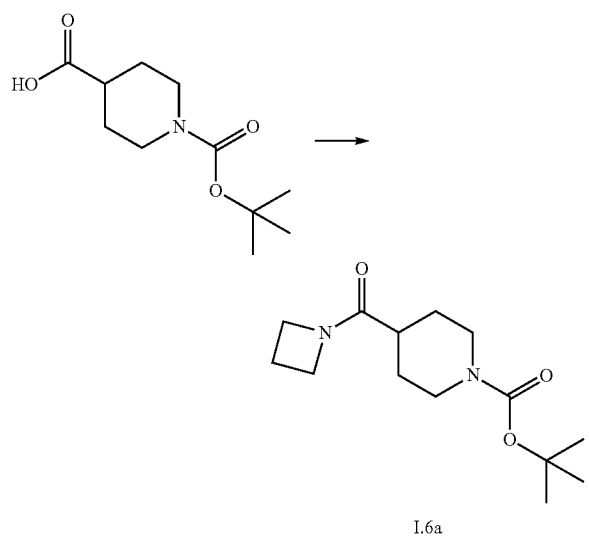

I.6a

Piperidine-1,4-dicarboxylic acid mono-tert-butyl ester (2.00 g; 8.72 mmol), TBTU (2.89 g; 9.00 mmol) and TEA (1.25 mL; 9.00 mmol) were dissolved in THF and stirred at RT for 1 h. Azetidine (0.61 mL; 9.00 mmol) and TEA (1.25 mL; 9.00 mmol) were added to the reaction mixture. The reaction mixture was stirred at RT overnight, diluted with water and extracted with EtOAc. The pooled organic phases were dried with $Na_2SO_4$ and reduced in vacuo to give the crude intermediate I.6a.

Yield: 2.00 g (85%), ESI-MS: m/z=269 $[M+H]^+$

Boc Deprotection:

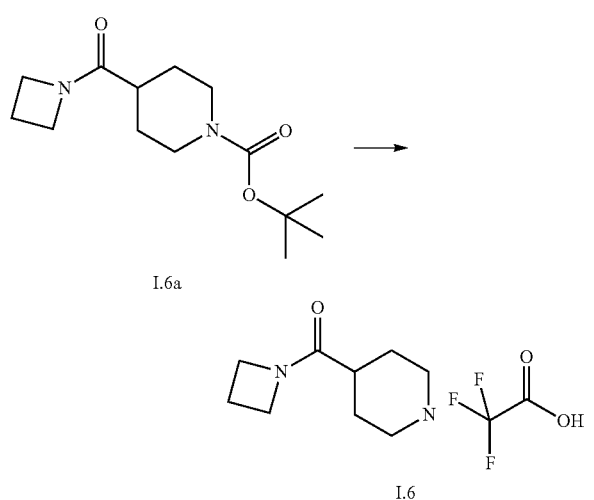

I.6

Intermediate I.6a (2.00 g; 7.45 mmol) was dissolved in DCM (20 mL) and TFA (2.23 mL; 30.00 mmol) was added. The reaction mixture was stirred at RT overnight and reduced in vacuo. The residue was taken up in DCM, filtered through a $HCO_3$-cartridge and the filtrate was evaporated under reduced pressure to provide intermediate I.6. Yield: 2.80 g (quant.), ESI-MS: m/z=169 $[M+H]^+$ I.7: 1-(3-Piperidin-4-yl-azetidin-1-yl)-ethanone Cbz Protection:

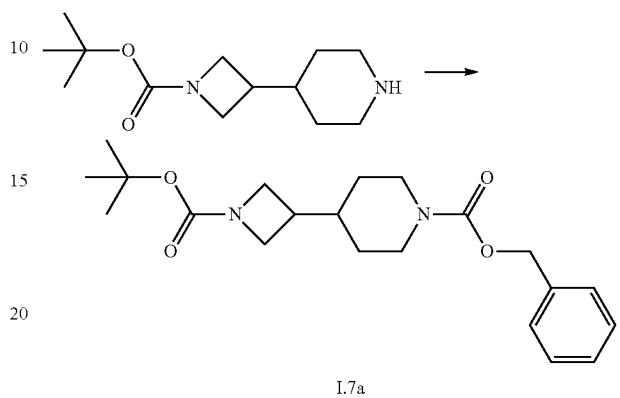

I.7a

3-Piperidine-4-yl-azetidine-1-carboxylic acid tert-butyl ester (500 mg; 2.08 mmol) was dissolved in DCM (10 mg), treated with TEA (348 µL; 2.50 mmol) and cooled to 0° C. To the reaction mixture was added benzyl chloroformate (322 µL; 2.29 mmol) dropwise and afterwards the reaction mixture was warmed to RT. The reaction mixture was stirred at RT overnight, diluted with DCM and extracted with water twice. The organic phase was dried and concentrated in vacuo. The crude material was purified by silica gel chromatography (cyclohexane/EtOAC) to provide intermediate I.7a.

Yield: 220 mg (28%), ESI-MS: m/z=375 $[M+H]^+$, $R_t$ (HPLC): 0.81 min (HPLC-2)

BOC Deprotection:

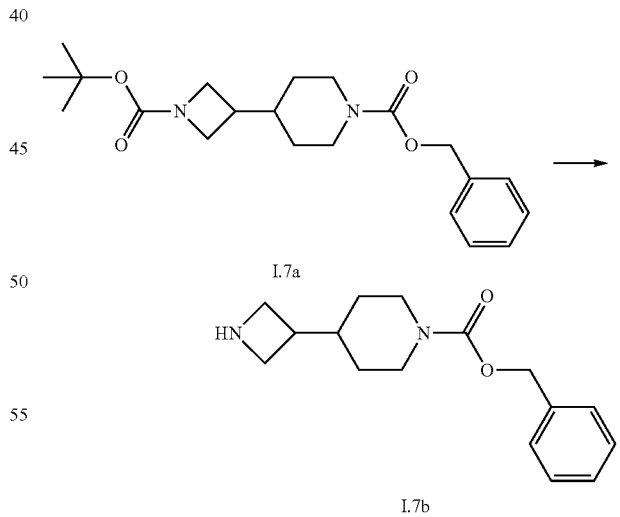

I.7b

To a solution of intermediate I.7a (220 mg; 0.59 mmol) in DCM (3 mL) was added TFA (453 µL; 5.87 mmol). The reaction mixture was stirred at RT overnight, the solvent was evaporated under reduced pressure and the residue was washed once with water and once with aq. solution of $NaHCO_3$. The organic phase was dried and concentrated in vacuo to give the crude intermediate I.7b.

Yield: 170 mg (100%), ESI-MS: m/z=275 [M+H]$^+$, R$_t$ (HPLC): 0.43 min (HPLC-2)

Acetylation:

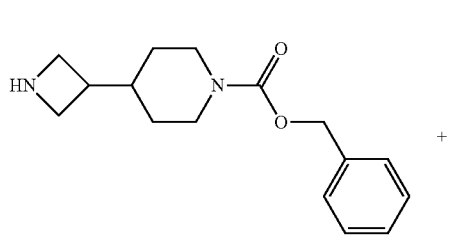

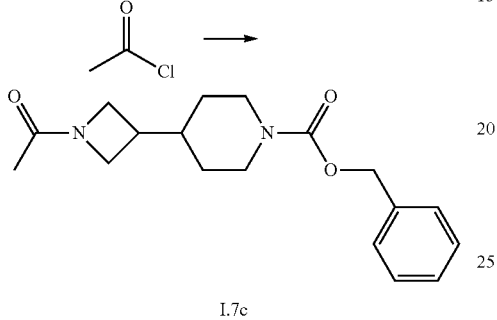

Intermediate I.7b (170 mg; 0.62 mmol) was dissolved in DCM (3.00 mL) and treated with TEA (258 µL; 1.86 mmol). The solution was cooled to 0° C. and acetyl chloride (53 µL; 0.74 mmol) was added dropwise. The reaction mixture was stirred at 0° C. for 10 min, warmed to RT and stirred at RT overnight. The reaction mixture was washed with water twice. The organic phase was dried and concentrated in vacuo to provide the crude intermediate I.7c.

Yield: 190 mg (97%), ESI-MS: m/z=317 [M+H]$^+$, R$_t$ (HPLC): 0.60 min (HPLC-2)

Cbz Deprotection:

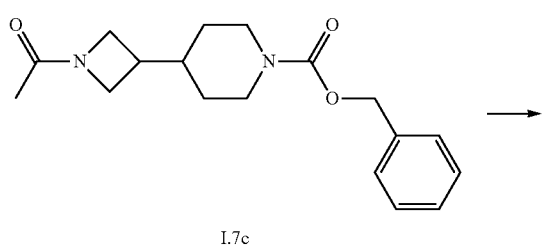

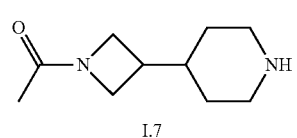

A mixture of intermediate I.7c (190 mg; 0.60 mmol) and 10% Pd/C (50 mg) in MeOH (5 mL) was treated with hydrogen (50 psi) at RT overnight. The reaction mixture was filtered and concentrated in vacuo to provide the crude intermediate I.7.

Yield: 90 mg (82%), ESI-MS: m/z=183 [M+H]$^+$

Intermediate I.8:
N,N-Dimethyl-2-piperidin-4-yl-acetamide trifluoroacetate

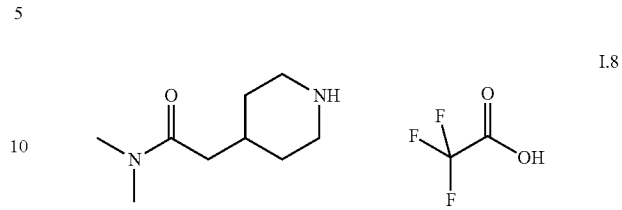

Intermediate I.8 was prepared according to the procedure described in WO 2008/071646, pp. 81-82.

I.9: N-Ethyl-2-piperidin-4-yl-acetamide hydrochloride

Amide Coupling:

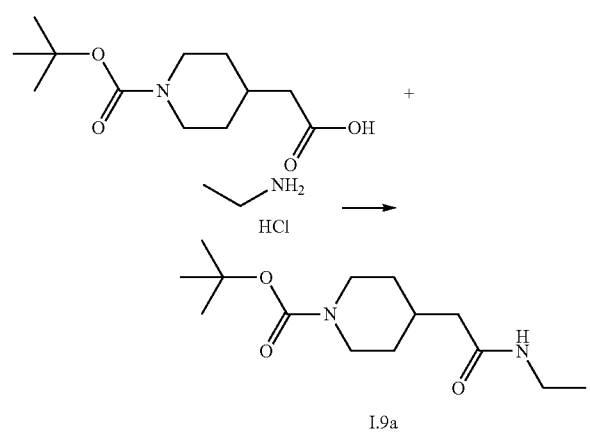

4-Carboxymethyl-piperidine-1-carboxylic acid tert-butyl ester (3.00 g; 12.33 mmol), TBTU (3.96 g; 12.33 mmol) and TEA (5.19 mL; 36.99 mmol) were dissolved in DMF (10 mL). The solution was stirred at RT for 10 min. Ethylamine hydrochloride (1.01 g; 12.33 mmol) was added to the reaction mixture and it was stirred at RT overnight. To the reaction mixture was added TBTU and after 5 min stirring at RT ethylamine hydrochloride (0.5 g; 6.15 mmol) was added. After 4 h stirring at RT the reaction mixture was extracted with EtOAc. The organic phases were concentrated in vacuo. The crude material was dissolved in DCM, filtered over a basic Alox-cartridge and the filtrate was washed with aq. 0.1 N HCl and evaporated under reduced pressure to give intermediate I.9a.

Yield: 3.3 g (99%), ESI-MS: m/z=271 [M+H]$^+$, R$_t$ (HPLC): 0.75 min (HPLC-4)

Boc Deprotection:

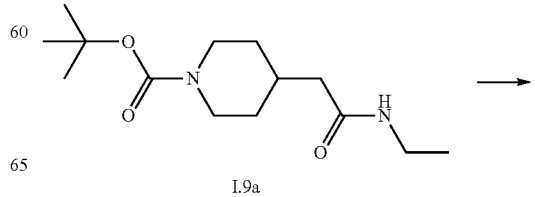

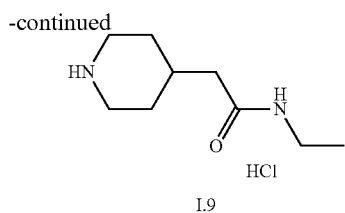

I.9 HCl

Intermediate I.9a (3.30 g; 12.21 mmol) was dissolved in 1,4-dioxane (30 mL) and a solution of 4 N hydrogen chloride in 1,4-dioxane (6.10 mL; 24.41 mmol) was added. The reaction mixture was stirred at RT overnight. To the reaction mixture was added a solution of 4 N hydrogen chloride in 1,4-dioxane (6.10 mL; 24.41 mmol) and it was stirred at RT overnight. The reaction diluted with diethyl ether and the precipitate was filtered to obtain intermediate I.9.

Yield: 2.52 g (100%), ESI-MS: m/z=171 [M+H]$^+$, R$_t$ (HPLC): 0.78 min (HPLC-6)

Intermediate I.10: (R)-Pyrrolidine-3-carboxylic acid methylamide hydrochloride

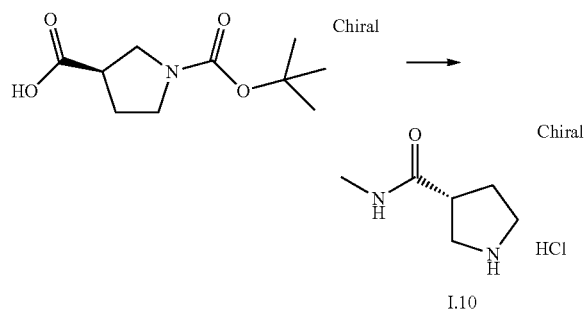

I.10

Step 1—Amide-coupling: (R)-Pyrrolidine-1,3-dicarboxylic acid 1-tert-butyl ester (800 mg, 3.61 mmol) was dissolved in THF (5.00 mL) and TEA (4.05 mL; 28.84 mmol) and a solution of methylamine in THF (2 M; 3.61 mL; 7.21 mmol) was added. To the reaction mixture was added a solution of 1-propanephosphonic acid cyclic anhydride (50% in THF; 4.21 mL; 7.21 mmol) at RT. The reaction mixture was stirred at RT for 1 h and diluted with 4 N aq. sodium hydroxide (20 mL). The aq. phase was extracted with MTBE (2×20 mL) and the pooled organic phases were washed with brine, dried, filtered and concentrated in vacuo.

Step 2—BOC deprotection: The crude material of step 1 was diluted with EtOAc (20 mL) and treated with 4 N HCl in 1,4-dioxane (2 mL; 8.00 mmol) at RT. The reaction mixture was stirred at RT overnight. The reaction mixture was concentrated in vacuo to provide intermediate I.10.

Yield: 755 mg (99%), ESI-MS: m/z=129 [M+H]$^+$, R$_t$ (HPLC): 0.12 min (HPLC-6)

Intermediate I.11:
Morpholin-4-yl-(S)-pyrrolidin-3-yl-methanone hydrochloride

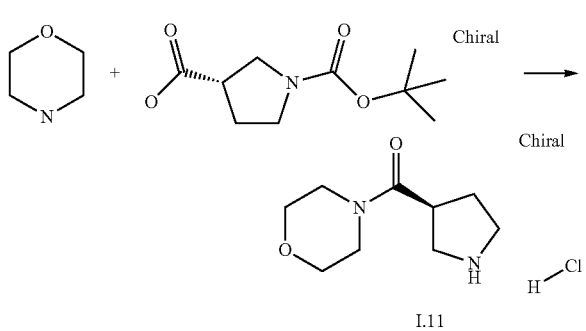

I.11

Step1—Amide-coupling: To the solution of (S)-Pyrrolidine-1,3-dicarboxylic acid 1-tert-butyl ester (500 mg; 2.32 mmol) and TEA (2.61 mL; 18.58 mmol) in THF (4.5 mL) was added a solution of morpholine (220 mg; 2.56 mmol) in THF (0.8 mL) and afterwards 1-propanephosphonic acid cyclic anhydride (50% in THF; 2.71 mL; 4.65 mmol) was added. The reaction mixture was stirred at RT for 3 h, diluted with aq. 4 N NaOH (20 mL) and extracted with MTBE (2×20 mL). The pooled organic phases were washed with brine, dried with Na$_2$SO$_4$, filtered and evaporated to dryness.

Step2—BOC deprotection: The crude material of step 1 was taken up in MeOH (20 mL) and hydrogen chloride (4 N in 1,4-dioxane; 5 mL; 20.00 mmol) was added. The reaction mixture was stirred at RT overnight, concentrated under reduced pressure and co-evaporated with toluene to provide intermediate I.11.

Yield: 527 mg (82%), ESI-MS: m/z=185 [M+H]$^+$, R$_t$ (HPLC): 0.12 min (HPLC-6) The following intermediate was prepared in analogy to the above described procedure using the corresponding starting materials. For changes from this procedure, see "synthesis comment".

| intermediate | structure | starting materials | R$_t$ [min] (HPLC method) | MS | synthesis comment |
|---|---|---|---|---|---|
| I.12 | ![structure] | ![starting material] | 0.12 (HPLC-6) | 143 | step1: 2 eq amine 2M dimethyl-amine THF |

| intermediate | structure | starting materials | $R_t$ [min] (HPLC method) | MS | synthesis comment |
|---|---|---|---|---|---|
| I.13 | 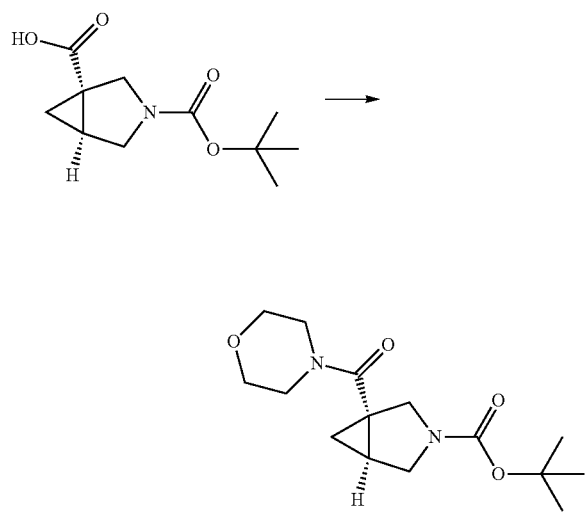 | 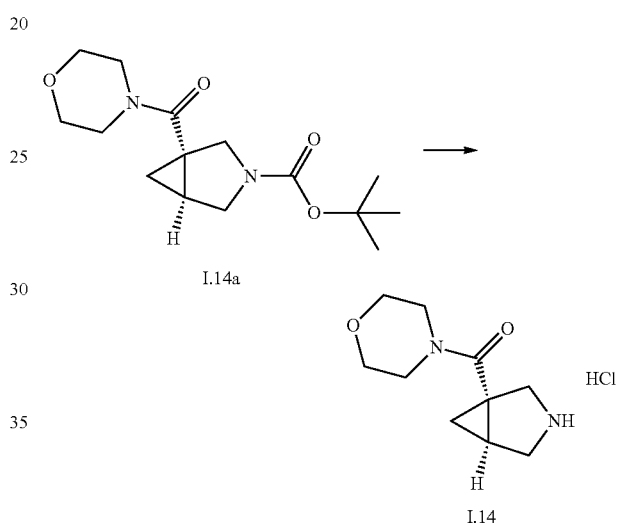 2M methyl-amine THF | 0.12 (HPLC-6) | 129 | step1: 2 eq amine |

Intermediate I.14: racemic cis-3-Aza-bicyclo[3.1.0]hex-1-yl-morpholin-4-yl-methanone hydrochloride Amide—Coupling:

Boc Deprotection:

Intermediate I.14a (0.76 g; 2.56 mmol) was dissolved in MeOH (2.00 mL) and hydrogen chloride (4 N in 1,4-dioxane; 5.00 mL; 20.00 mmol) was added. The reaction mixture was stirred at RT overnight. The reaction mixture was diluted with MTBE, the precipitate was filtered and washed with MTBE. The solvent was allowed to evaporate in order to obtain intermediate I.14 as a dry solid.

Yield: 0.53 g (89%), ESI-MS: m/z=197 [M+H]⁺, $R_t$ (HPLC): 0.20 min (HPLC-1)

Racemic cis-3-aza-bicyclo[3.1.0]hexane-1,3-dicarboxylic acid-3-tert-butyl ester (1.00 g; 4.40 mmol) and HATU (1.90 g; 4.84 mmol) were suspended in DMF und DIPEA (1.89 mL; 11.00 mmol) was added. The reaction mixture was stirred at RT for 30 min. To the reaction mixture was added morpholine (0.77 mL; 8.80 mmol) and the solution was stirred at RT overnight. The reaction mixture was diluted with water (20 mL) and extracted with DCM (3×20 mL). The pooled organic phases were washed with aq. 1 N NaOH (20 mL), dried and concentrated in vacuo. The crude material was purified by RP-HPLC (C18, 50° C., Acetonitrile+ 0.1% TFA in water) to obtain intermediate I.14a.

Yield: 1.17 g (90%), ESI-MS: m/z=241 [M+H]⁺, $R_t$ (HPLC): 0.90 min (HPLC-6)

I.15: (4-Azetidin-3-yl-piperidin-1-yl)-cyclorpopyl-methanone

Acylation:

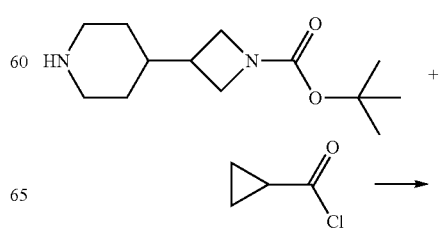

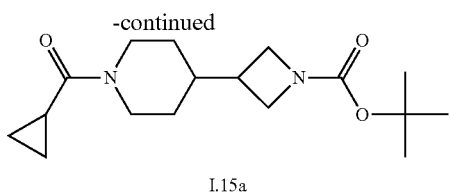

I.15a

3-Piperidin-4-yl-azetidine-1-carboxylic acid tert-butyl ester (530 mg; 2.21 mmol) was dissolved in DCM (20 mL) and TEA (0.71 mL; 5.07 mmol) was added. The solution was cooled with an ice bath and cyclopropanecarbonyl chloride (300 mg; 2.87 mmol) dissolved in DCM (1 mL) was added. The reaction mixture was stirred at 0° C. for 1 h and stirred at 15° C. for 3 d. The reaction mixture was diluted with DCM and washed with sat. aq. NaHCO₃-solution once, two times with aq. 0.5 N HCl-solution and once with brine. The organic phase was dried over Na₂SO₄ and concentrated in vacuo to give intermediate I.15a.

Yield: 690 mg (91%), ESI-MS: m/z=309 [M+H]⁺, R$_t$ (HPLC): 0.64 min (HPLC-2)

Boc Deprotection:

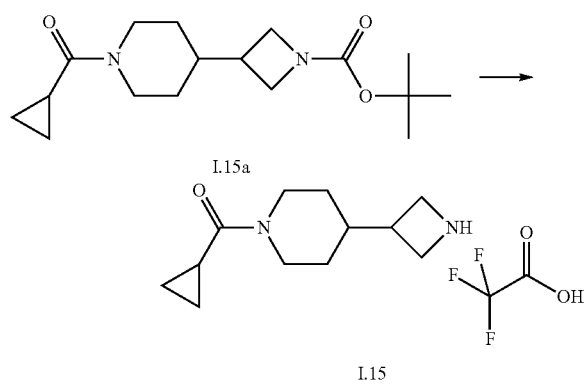

Intermediate I.15a (690 mg; 3.01 mmol), TFA (0.62 mL; 8.05 mmol) and DCM (20 mL) were stirred at RT overnight and evaporated to give intermediate I.15.

Yield: 500 mg (77%), ESI-MS: m/z=209 [M+H]⁺, R$_t$ (HPLC): 0.26 min (HPLC-2)

Intermediate I.16: (R)-Pyrrolidine-3-carboxylic acid amide trifluoroacetate

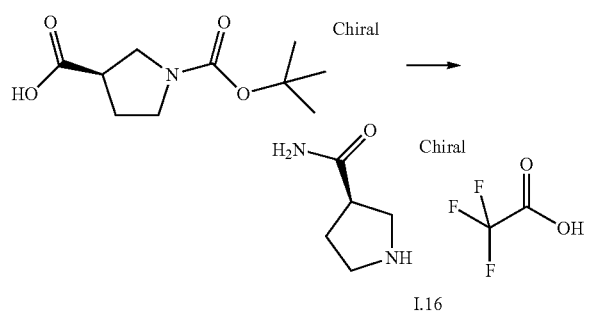

Step 1—Amide-coupling: (R)-Pyrrolidine-1,3-dicarboxylic acid 1-tert-butyl ester (800 mg; 3.61 mmol) was diluted with DCM (8 mL) and N-methylmorpholine (0.45 mL; 3.97 mmol) was added. The reaction mixture was cooled to 0° C. and IBCF (0.5 mL; 3.79 mmoL) was added. The reaction mixture was stirred at 0° C. for 5 min, warmed to RT and stirred for 1 h at RT. After addition of aq. NH₄OH (32%; 0.67 mL; 5.41 mmol) the reaction mixture was stirred at RT for 80 min. The reaction mixture was diluted with water and extracted with DCM (2×20 mL). The pooled organic phases were washed with sat. aq. NaHCO₃-solution, dried and evaporated under reduced pressure.

Step2—BOC deprotection: The crude material of step 1 was dissolved in DCM (5 mL), TFA (0.83 mL; 10.81 mmol) was added and the reaction mixture was stirred at RT for 1 h. To the reaction mixture was added TFA (0.83 mL; 10.81 mmol) and it was stirred at RT overnight. The reaction mixture was concentrated in vacuo to provide intermediate I.16.

Yield: 1.19 g (100%), ESI-MS: m/z=115 [M+H]⁺, R$_t$ (HPLC): 0.11 min (HPLC-6)

I.17: Morpholin-4-yl-(S)-pyrrolidin-3-yl-methanone

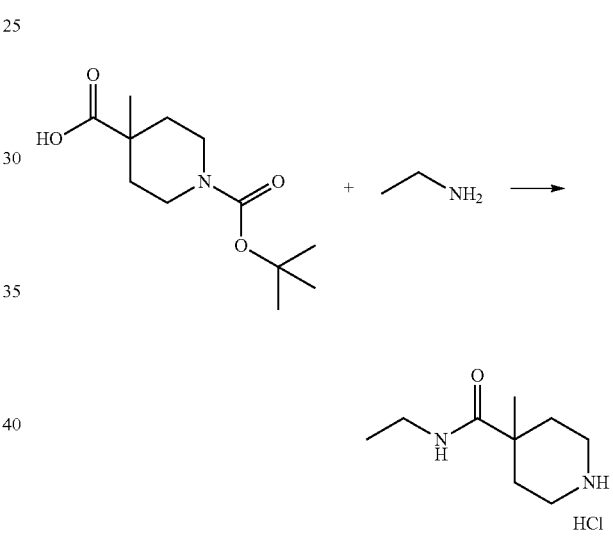

Step 1—Amide-coupling: 4-Methyl-piperidine-1,4-dicarboxylic acid mono-tert-butyl ester (500 mg, 1.99 mmol) was dissolved in THF (5 mL) and TEA (2.24 mL; 15.95 mmol) and a solution of ethylamine in THF (2 M; 1.99 mL; 3.99 mmol) was added. To the reaction mixture was added a solution of 1-propanephosphonic acid cyclic anhydride (50% in THF; 2.33 mL; 3.99 mmol) at RT. The reaction mixture was stirred at RT for 1 h and diluted with 4 N aq. sodium hydroxide (20 mL). The aq. phase was extracted with MTBE (2×20 mL) and the pooled organic phases were washed with brine (20 mL), dried, filtered and concentrated in vacuo.

Step 2—BOC deprotection: The crude material of step 1 was diluted with EtOAc (20 mL) and treated with 4 N HCl in 1,4-dioxane (1 mL; 4.00 mmol) at RT. The reaction mixture was stirred at RT overnight. The reaction mixture was concentrated in vacuo to provide intermediate I.17.

Yield: 236 mg (46%), ESI-MS: m/z=171 [M+H]⁺, R$_t$ (HPLC): 0.13 min (HPLC-6)

Intermediate II.1: trans-3-(6-Chloro-pyridine-3-sulfonyl-3-aza-bicyclo[3.1.0]hexane-6-carboxylic acid methylamide

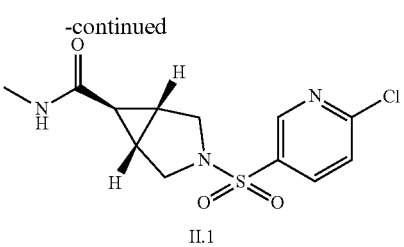

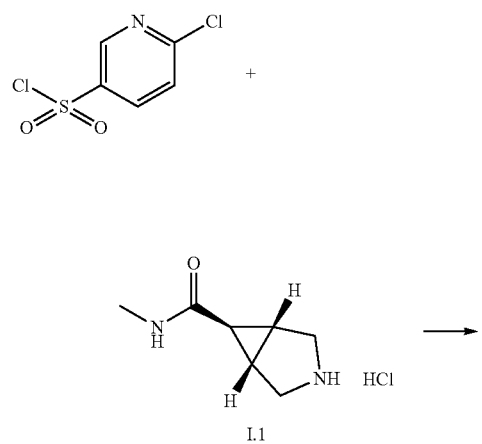

The mixture of intermediate I.1 (550 mg; 2.49 mmol) and TEA (1.91 mL; 13.58 mmol) in DCM (15 mL) was cooled to 0-5° C. 6-Chloropyridine-3-sulfonyl chloride (500 mg; 2.26 mmol) was added to the reaction mixture and it was stirred for 10 min at 0° C., then warmed to RT and stirred at RT overnight. The reaction mixture was diluted with DCM and washed with water and with 1 N aq. HCl. The organic phase was dried with Na$_2$SO$_4$, filtered and reduced in vacuo. The crude material was triturated with diisopropyl ether, the solid was filtered, washed with diisopropyl ether and dried at 60° C. in vacuo to give Intermediate II.1.

Yield: 507 mg (71%), ESI-MS: m/z=316 [M+H]$^+$, R$_t$ (HPLC): 0.83 min (HPLC-6)

The following intermediates were prepared in analogy to the above described procedure using 6-chloropyridine-3-sulfonyl chloride and the corresponding starting material. For changes from this procedure, see "synthesis comment".

| intermediate | structure | starting material | R$_t$ [min] (HPLC method) | MS | synthesis comment |
|---|---|---|---|---|---|
| II.2 | 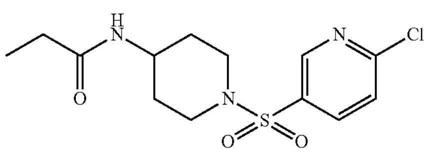 [SMILES: CCC(=O)NC1CCN(S(=O)(=O)c2ccc(Cl)nc2)CC1] | | | | 3 eq TEA; NMP; RT; 2 h; used as such in the next step |
| II.3 | 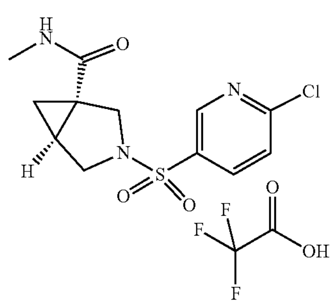 | I.2 | 0.47 (HPLC-1) | 315 | 1 h; workup: extraction with water; crude material triturated with diisopropyl ether |
| II.4 | 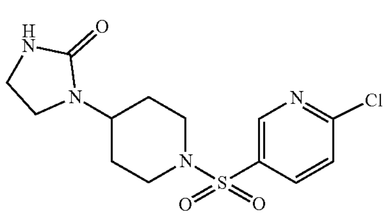 [SMILES: O=C1NCCN1C1CCN(S(=O)(=O)c2ccc(Cl)nc2)CC1] | | | | 3 eq TEA; NMP; 1 h; used as such in the next step |

-continued

| intermediate | structure | starting material | R$_t$ [min] (HPLC method) | MS | synthesis comment |
|---|---|---|---|---|---|
| II.5 | 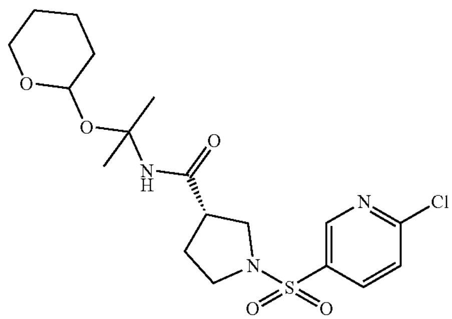 [SMILES: CC(C)(NC(=O)[C@H]1CCN(S(=O)(=O)c2ccc(Cl)nc2)C1)OC1CCCCO1] | I.3 | 0.84 (HPLC-6) | 362 | 3 eq TEA; RT; 30 min; used as such in the next step |
| II.6 | 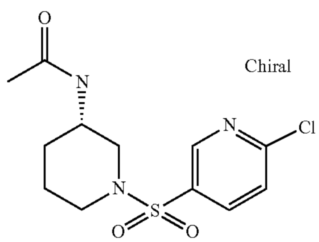 [SMILES: CC(=O)N[C@H]1CCCN(S(=O)(=O)c2ccc(Cl)nc2)C1] | I.4 | | | 3 eq TEA; NMP; RT; 2 h; used as such in the next step |
| II.7 | 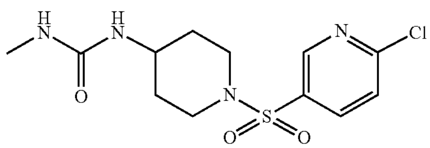 [SMILES: CNC(=O)NC1CCN(S(=O)(=O)c2ccc(Cl)nc2)CC1] | | | | 3 eq TEA; NMP; RT; 2 h; used as such in the next step |
| II.8 | 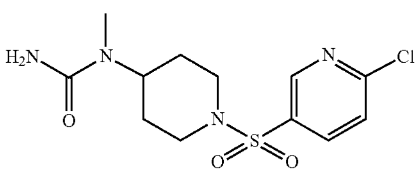 [SMILES: CN(C(N)=O)C1CCN(S(=O)(=O)c2ccc(Cl)nc2)CC1] | | 0.83 (HPLC-6) | 333 | 2 eq TEA; 1 h; workup: neutral extraction; drying at 50° C. |
| II.9 | 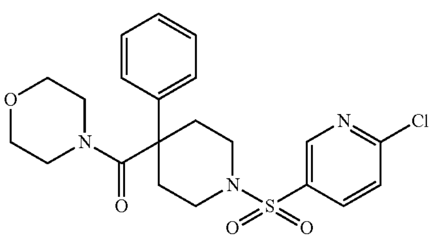 [SMILES: O=C(N1CCOCC1)C1(c2ccccc2)CCN(S(=O)(=O)c2ccc(Cl)nc2)CC1] | I.5 | 1.06 (HPLC-6) | 450 | 3 eq TEA; |
| II.10 | 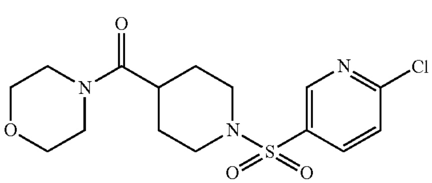 [SMILES: O=C(C1CCN(S(=O)(=O)c2ccc(Cl)nc2)CC1)N1CCOCC1] | | 0.87 (HPLC-6) | 374 | |
| II.11 | 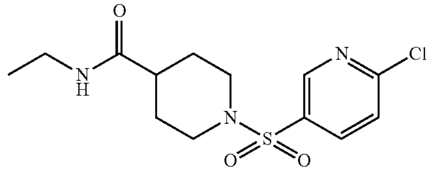 [SMILES: CCNC(=O)C1CCN(S(=O)(=O)c2ccc(Cl)nc2)CC1] | | 0.88 (HPLC-6) | 332 | |

-continued

| intermediate | structure | starting material | R$_t$ [min] (HPLC method) MS | synthesis comment |
|---|---|---|---|---|
| II.12 | 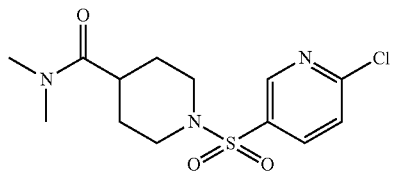 [SMILES: CN(C)C(=O)C1CCN(S(=O)(=O)c2ccc(Cl)nc2)CC1] | | 0.88 (HPLC-6) 332 | |
| II.13 | 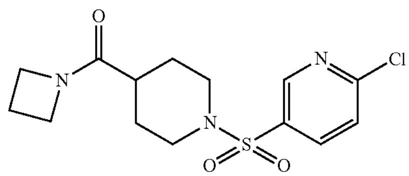 [SMILES: O=C(C1CCN(S(=O)(=O)c2ccc(Cl)nc2)CC1)N1CCC1] | I.6 | | 3 eq TEA; NMP; RT; 2 h; used as such in the next step |
| II.14 | 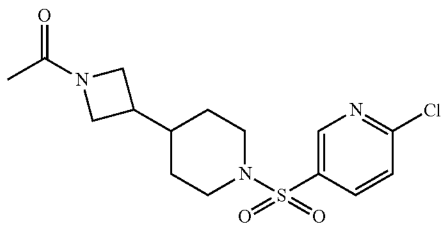 [SMILES: CC(=O)N1CC(C2CCN(S(=O)(=O)c3ccc(Cl)nc3)CC2)C1] | I.7 | | 1.5 eq TEA; workup: aq. extraction |
| II.15 | 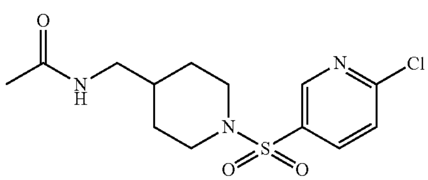 [SMILES: CC(=O)NCC1CCN(S(=O)(=O)c2ccc(Cl)nc2)CC1] | | | 3 eq TEA; NMP; RT; 2 h; used as such in the next step |
| II.16 | 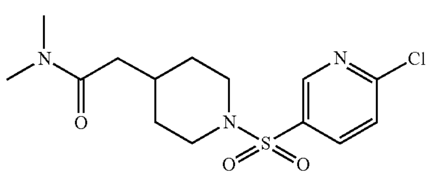 [SMILES: CN(C)C(=O)CC1CCN(S(=O)(=O)c2ccc(Cl)nc2)CC1] | I.8 | | 3 eq TEA; NMR; RT; 1 h; used as such in the next step |
| II.17 | 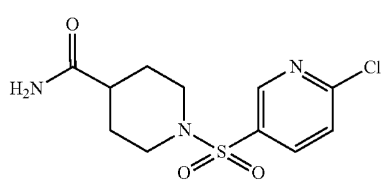 [SMILES: NC(=O)C1CCN(S(=O)(=O)c2ccc(Cl)nc2)CC1] | | 0.79 (HPLC-6) 304 | 3 eq TEA; 1 h 20 min |
| II.18 | 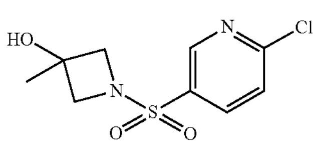 [SMILES: CC1(O)CN(S(=O)(=O)c2ccc(Cl)nc2)C1] | | | 3 eq TEA; NMP; RT; 2 h; used as such in the next step |
| II.19 | 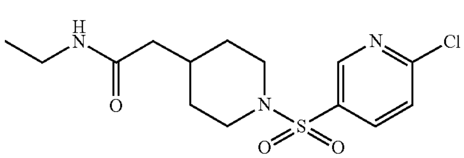 [SMILES: CCNC(=O)CC1CCN(S(=O)(=O)c2ccc(Cl)nc2)CC1] | I.9 | | 3 eq TEA; NMP; RT; 2 h; used as such in the next step |

-continued

| intermediate | structure | starting material | R$_t$ [min] (HPLC method) | MS | synthesis comment |
|---|---|---|---|---|---|
| II.20 | 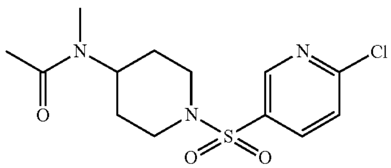 [SMILES: CC(=O)N(C)C1CCN(S(=O)(=O)c2ccc(Cl)nc2)CC1] | | | | 3 eq TEA; NMP; RT; 2 h; used as such in the next step |
| II.21 | 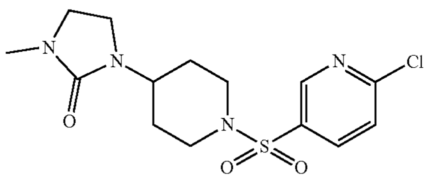 [SMILES: CN1CCN(C2CCN(S(=O)(=O)c3ccc(Cl)nc3)CC2)C1=O] | HCl | | | 3 eq TEA; NMP; 1 h; used as such in the next step |
| II.22 | 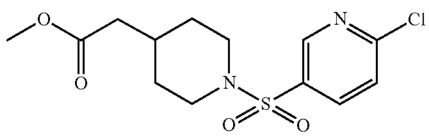 [SMILES: COC(=O)CC1CCN(S(=O)(=O)c2ccc(Cl)nc2)CC1] | | 0.60 (HPLC-1) | 332 | 2 eq TEA; RT; 1.5 h workup: aq. acidic extraction |
| II.23 | 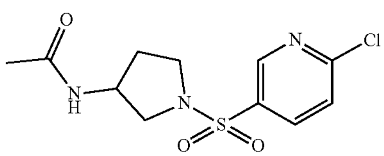 [SMILES: CC(=O)NC1CCN(S(=O)(=O)c2ccc(Cl)nc2)C1] | | | | 1.5 eq TEA; NMP; 1 h; used as such in the next step |
| II.24 | Chiral | I.10 | 0.81 (HPLC-6) | 304 | 4.00 eq TEA; RT 40 min; used as such in the next step |
| II.25 | Chiral | I.11 | 0.87 (HPLC-6) | 360 | 3.00 eq TEA; THF/DMSO; 440 min; used as such in the next step |
| II.26 | 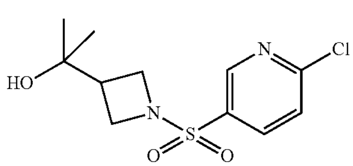 [SMILES: CC(C)(O)C1CN(S(=O)(=O)c2ccc(Cl)nc2)C1] | HCl | | | 3 eq TEA; NMP; RT; 2 h; used as such in the next step |
| II.27 | Chiral | I.12 | 0.87 (HPLC-6) | 318 | DMSO; 40 min; used as such in the next step |

-continued

| intermediate | structure | starting material | R$_t$ [min] (HPLC method) | MS | synthesis comment |
|---|---|---|---|---|---|
| II.28 | [N,N-dimethyl azetidine-3-carboxamide N-sulfonyl-(6-chloropyridin-3-yl)] | [N,N-dimethyl azetidine-3-carboxamide·HCl] | 0.84 (HPLC-6) | 304 | THF; 37 min; used as such in the next step |
| II.29 | [N-methyl pyrrolidine-3-carboxamide N-sulfonyl-(6-chloropyridin-3-yl)] | I.13 | 0.81 (HPLC-6) | 304 | THF/DMSO; 40 min; used as such in the next step |
| II.30 | [morpholine carbonyl bicyclic pyrrolidine N-sulfonyl-(6-chloropyridin-3-yl)] | I.14 | 0.48 (HPLC-1) | 371 | RT; workup: neutral aq. extraction; purification by RP-HPLC (ACN/water + TFA) |
| II.31 | [azetidine-3-carboxamide N-sulfonyl-(6-chloropyridin-3-yl)] | [azetidine-3-carboxamide·HCl] | 0.73 (HPLC-6) | 276 | 2.10 eq TEA; THF; RT; 36 min; used as such in the next step |
| II.32 | [cyclopropanecarbonyl piperidine-azetidine N-sulfonyl-(6-chloropyridin-3-yl)] | I.15 | | | 3 eq TEA; NMP; RT; 2 h; used as such in the next step |
| II.33 | [Chiral pyrrolidine-3-carboxamide N-sulfonyl-(6-chloropyridin-3-yl)] | I.16 | 0.77 (HPLC-6) | 290 | 5 eq TEA; workup: neutral aq. extraction; precipitate filtered, co-evaporated with iPrOH, Tol |
| II.34 | [N-ethyl 4-methyl piperidine-4-carboxamide N-sulfonyl-(6-chloropyridin-3-yl)] | I.17 | 0.93 (HPLC-6) | 346 | 4 eq TEA; DMSO/THF; RT; 25 min; used as such in the next step |

-continued

| intermediate | structure | starting material | R$_t$ [min] (HPLC method) | MS | synthesis comment |
|---|---|---|---|---|---|
| II.35 | (Chiral) 3-hydroxypyrrolidine sulfonyl 2-chloropyridine | (Chiral) 3-hydroxypyrrolidine | 0.78 (HPLC-6) | 263 | 2 eq TEA; 1.5 h |
| II.36 | (Chiral) 3-hydroxypyrrolidine sulfonyl 2-chloropyridine (enantiomer) | (Chiral) 3-hydroxypyrrolidine | 0.78 (HPLC-6) | 263 | |
| II.37 | 3,3-difluoroazetidine sulfonyl 2-chloropyridine | 3,3-difluoroazetidine HCl | 0.51 (HPLC-1) | 269 | RT; 1 h; workup: neutral aq. extraction; crude material triturated with diisopropyl ether |
| II.38 | azetidine sulfonyl 2-chloropyridine | azetidine | 0.43 (HPLC-1) | 233 | 2 eq TEA; RT; 1 h; workup: neutral aq. extraction; crude material triturated with diisopropyl ether |
| II.39 | 3-methoxypyrrolidine sulfonyl 2-chloropyridine | 3-methoxypyrrolidine HCl | 0.47 (HPLC-1) | 277 | 2 eq TEA; RT; 1 h; workup: neutral aq. extraction |
| II.40 | 3-azabicyclo[3.1.0]hexane sulfonyl 2-chloropyridine | 3-azabicyclo[3.1.0]hexane HCl | | | RT; 1 h; workup: neutral aq. extraction; crude material triturated with diisopropyl ether |
| II.41 | 3-methoxyazetidine sulfonyl 2-chloropyridine | 3-methoxyazetidine HCl | 0.44 (HPLC-1) | 263 | 2 eq TEA; RT 1 h; workup: aq. neutral extraction; crude material triturated with diisopropyl ether |
| II.42 | 3,3-difluoropyrrolidine sulfonyl 2-chloropyridine | 3,3-difluoropyrrolidine HCl | 0.53 (HPLC-1) | 283 | 3 eq TEA; RT; 1 h; workup: aq. neutral extraction; crude material triturated with diisopropyl ether |

| intermediate | structure | starting material | R$_t$ [min] (HPLC method) | MS | synthesis comment |
|---|---|---|---|---|---|
| II.43 | 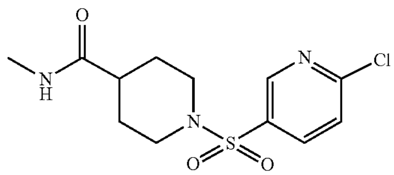 [SMILES: CNC(=O)C1CCN(S(=O)(=O)c2ccc(Cl)nc2)CC1] | | 0.82 (HPLC-6) | 318 | 3 eq TEA |
| II.44 | 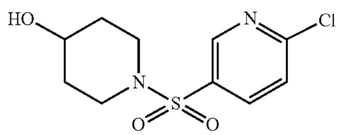 [SMILES: O=S(=O)(c1ccc(Cl)nc1)N1CCC(O)CC1] | | 0.81 (HPLC-6) | 277 | 3 eq TEA |
| II.45 | 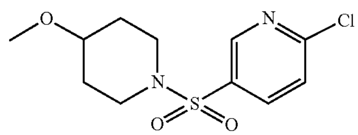 [SMILES: COC1CCN(S(=O)(=O)c2ccc(Cl)nc2)CC1] | | 0.53 (HPLC-1) | 291 | 2 eq TEA; RT; 1 h; workup: neutral aq. extraction with DCM; |
| II.46 | 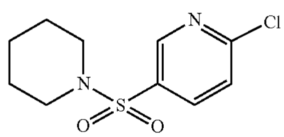 [SMILES: O=S(=O)(c1ccc(Cl)nc1)N1CCCCC1] | | 0.58 (HPLC-1) | 261 | 2 eq TEA; RT; 1 h; workup: washing with water; crude material triturated with diisopropyl ether |
| II.47 | 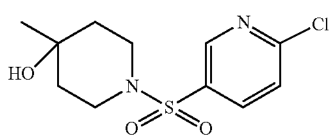 [SMILES: CC1(O)CCN(S(=O)(=O)c2ccc(Cl)nc2)CC1] | | | | 3 eq TEA |
| II.48 | Chiral | | 0.43 (HPLC-2) | 290 | 3 eq TEA |
| II.49 | 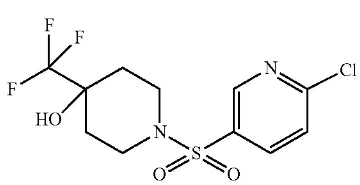 [SMILES: O=S(=O)(c1ccc(Cl)nc1)N1CCC(O)(C(F)(F)F)CC1] | | 0.63 (HPLC-2) | 345 | 3 eq TEA |

Intermediate III.1: 1-(6-Fluoro-pyridine-3-sulfonyl)-piperidine-4-carboxylic acid methyl ester

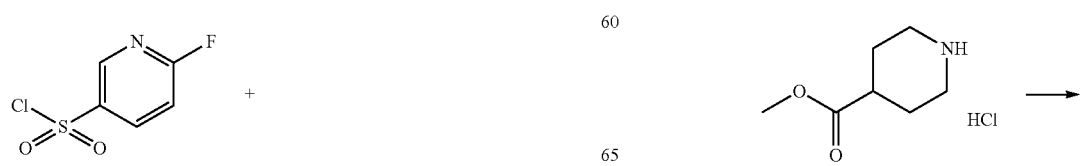

-continued

65

-continued

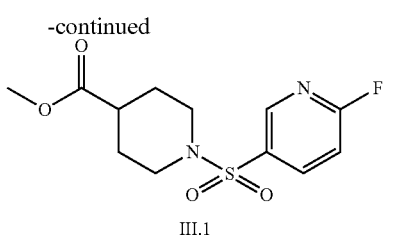

III.1

Piperidine-4-carboxylic acid methyl ester hydrochloride (1.15 g; 6.39 mmol) was suspended in DCM (40 mL) and TEA (3.56 mL; 25.56 mmol) was added. To the reaction mixture was added a solution of 6-fluoropyridine-3-sulfonyl chloride (1.25 g; 6.39 mmol) in DCM (10 mL). It was stirred at RT for 45 min, then diluted with DCM (50 mL) and washed with water (2×40 mL). The pooled organic phases were dried with $Na_2SO_4$ and concentrated in vacuo. The crude material was suspended in MTBE and the remaining solid was filtered to provide intermediate III.1.

Yield: 1.4 g (73%), ESI-MS: m/z=302 $[M+H]^+$, $R_t$ (HPLC): 0.52 min (HPLC-1)

The following intermediates were prepared in analogy to the above described procedure using 6-fluoropyridine-3-sulfonyl chloride and the corresponding starting material. For changes from this procedure, see "synthesis comment".

66

Intermediate IV.1: tert-Butyl-N-[2-(fluoromethyl-idene)-3-hydroxypropyl]-carbamate (E/Z-mixture)

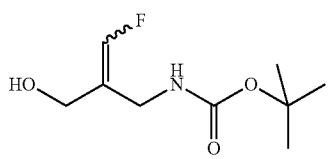

IV.1

The E/Z-mixture of the alcohol (intermediate IV.1) was prepared according to the procedure described in WO 2013/163675, pp. 50-53.

| intermediate | structure | starting materials | $R_t$ [min] (HPLC method) | MS | synthesis comment |
|---|---|---|---|---|---|
| III.2 | 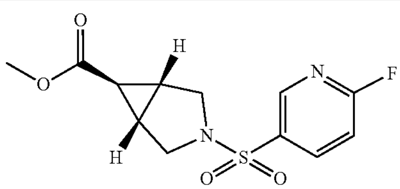 [SMILES: COC(=O)[C@H]1[C@@H]2CN(S(=O)(=O)c3ccc(F)nc3)C[C@@H]21] | | 0.53 (HPLC-1) | 301 | 2 eq TEA; RT; 1.5 h |
| III.3 | 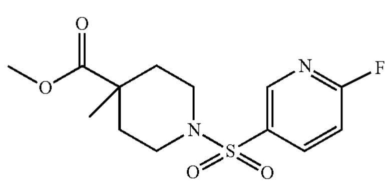 [SMILES: COC(=O)C1(C)CCN(S(=O)(=O)c2ccc(F)nc2)CC1] | | 0.53 (HPLC-1) | 301 | 2 eq TEA; RT; 2.5 h; |
| III.4 | 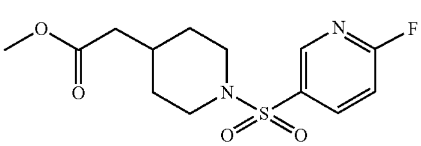 [SMILES: COC(=O)CC1CCN(S(=O)(=O)c2ccc(F)nc2)CC1] | | 0.67 (HPLC-1) | 317 | 2 eq TEA; 3.5 h |

Intermediate IV.2: ((E)-3-Fluoro-2-hydroxymethyl-allyl)-carbamic acid tert-butyl ester

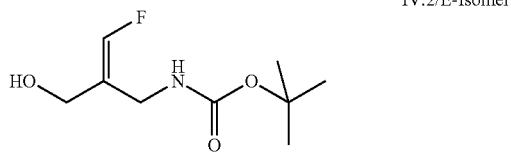

IV.2/E-Isomer

Intermediate IV.1 (4.00 g; 19.49 mmol) was purified three times by column chromatography on silica gel to give the single E-isomer IV.2 (1.95 g; 9.50 mmol; 49%).

Example 1: trans-3-[6-((E)-2-Aminomethyl-3-fluoro-allyloxy)-pyridine-3-sulfonyl]-3-aza-bicyclo[3.1.0]hexane-6-carboxylic acid methylamide trifluoroacetate Substitution:

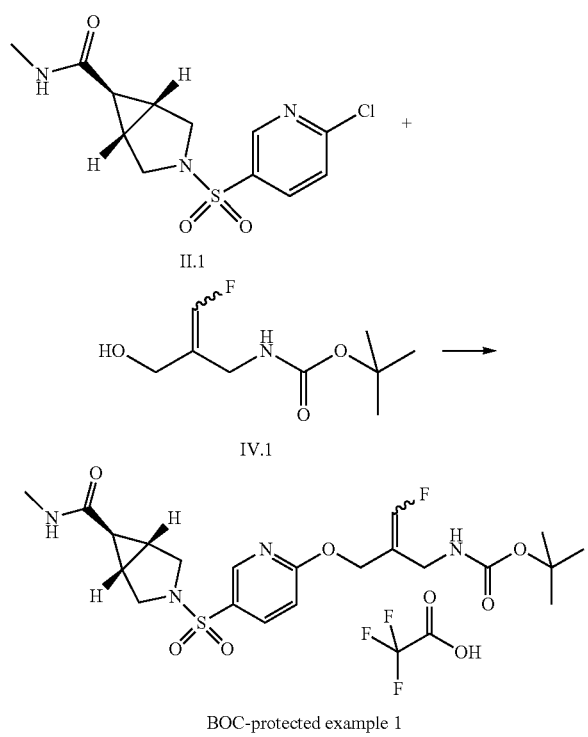

Intermediate II.1 (326 mg; 85% purity; 0.88 mmol) and intermediate IV.1 (216 mg; 1.05 mmol) were dissolved in THF (1 mL; S) and DMSO (1 mL; S) and cooled to 0° C. To the reaction mixture was added sodium tert-butoxide (2 M in THF; 0.53 mL; 1.05 mmol; B) and after 5 min at 0° C. the mixture was stirred at RT (T) for 35 min (t). The reaction mixture was purified by RP-HPLC (ACN/water+TFA) to obtain the BOC-protected example 1.

Yield: 410 mg (96%), ESI-MS: m/z=385 [M+H—BOC]$^+$, R$_t$ (HPLC): 1.05 min (HPLC-6)

Boc Deprotection:

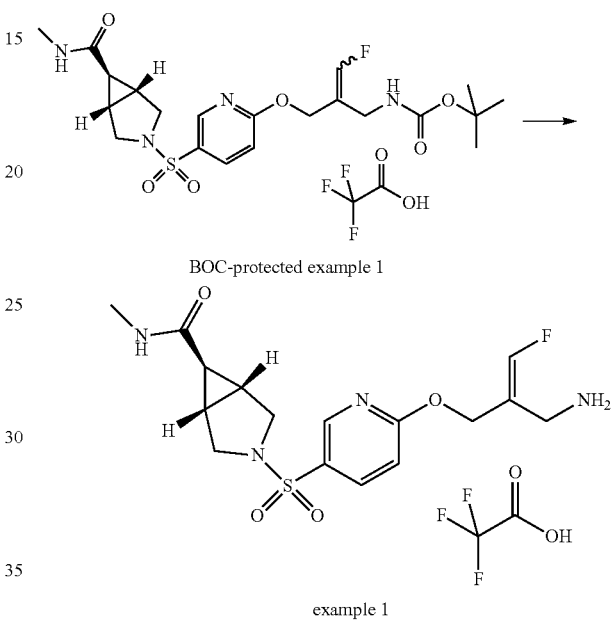

The BOC-protected example 1 as the E/Z-mixture (410 mg; 0.85 mmol) was dissolved in DCM (15 mL; S) and TFA (266 μL; 3.45 mmol; A) was added. The reaction mixture was stirred at RT (T) for 2.5 h (t), then evaporated under reduced pressure, dissolved in MeOH (5 mL) and purified by RP-HPLC (ACN/water+TFA) to give example 1.

Yield: 160 mg (38%), ESI-MS: m/z=385 [M+H]$^+$, R$_t$ (HPLC): 0.64 min (HPLC-5)

The following examples (example number given in column #) were prepared in analogy to the above described procedure using the corresponding starting materials. Details for the two steps are given in the column synthesis comment, the retention-time and mass (ESI-MS, m/z=[M+H]$^+$) determined by HPLC-MS are given in the columns RT and MS.

| # | structure |
|---|-----------|
| 2 | 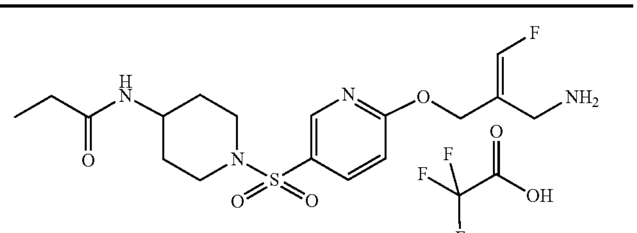 |

| # | structure |
|---|-----------|
| 3 | 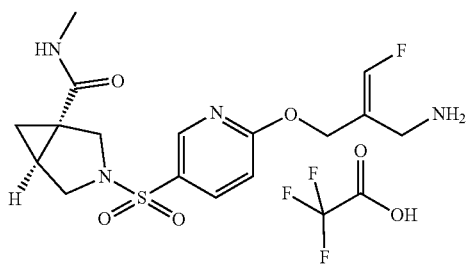 |
| 4 | 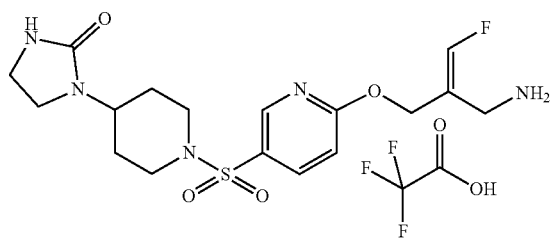 |
| 5 | 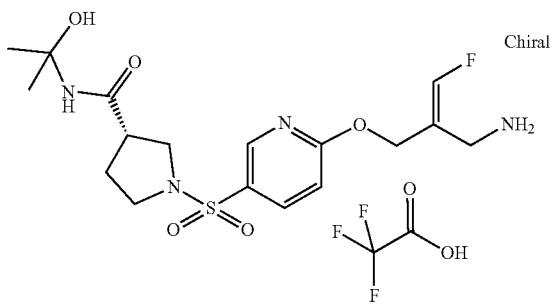 |
| 6 | 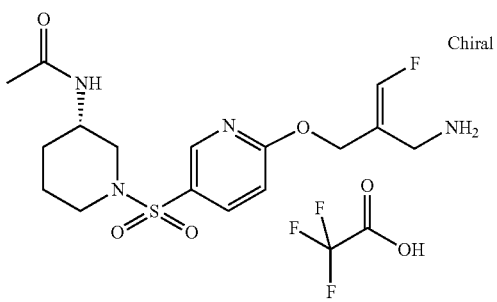 |
| 7 | 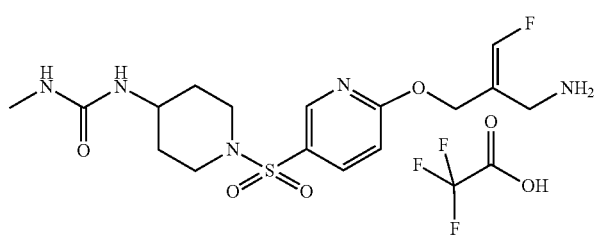 |

-continued
| # | structure |
|---|---|
| 8 | 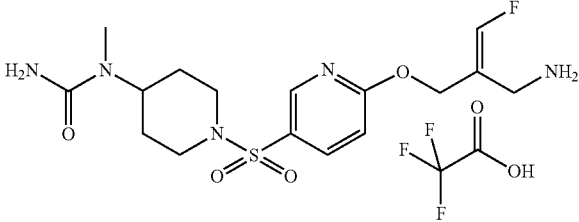 |
| 9 | 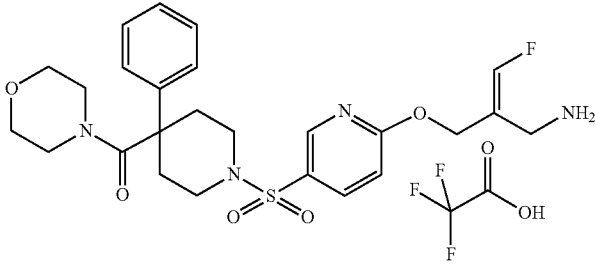 |
| 10 | 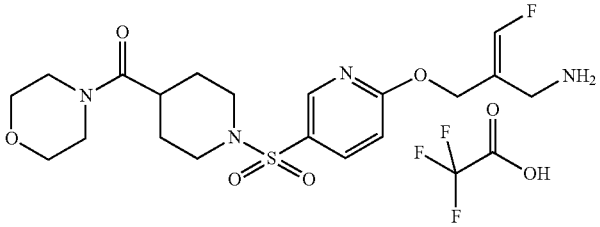 |
| 11 | 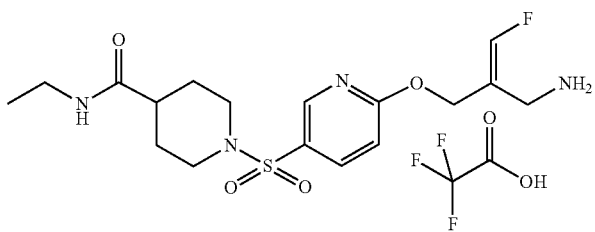 |
| 12 | 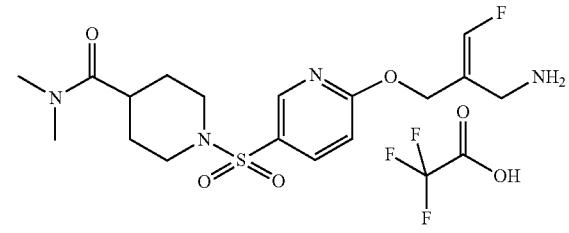 |
| 13 | 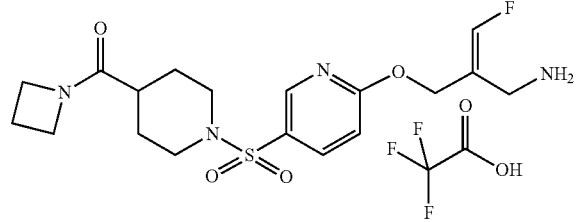 |

| # | structure |
|---|-----------|
| 14 | 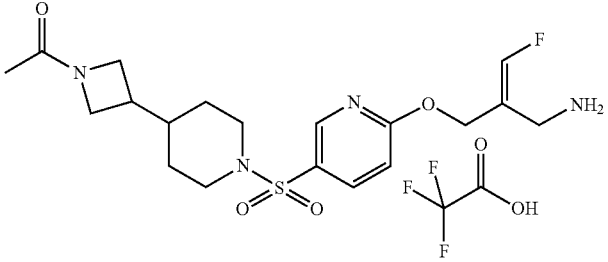 |
| 15 | 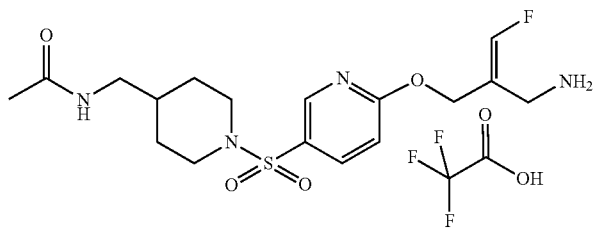 |
| 16 | 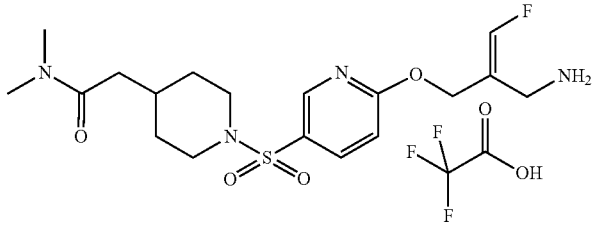 |
| 17 | 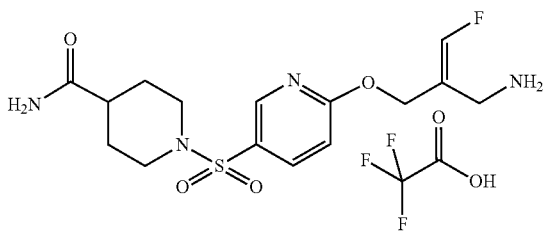 |
| 18 | 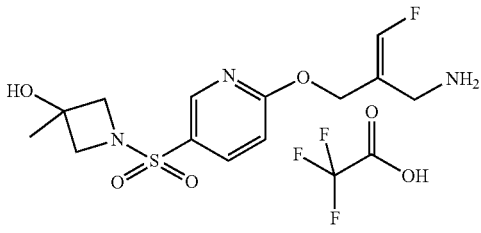 |
| 19 | 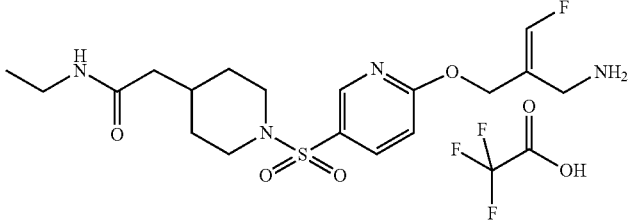 |

-continued
| # | structure |
|---|---|
| 20 | 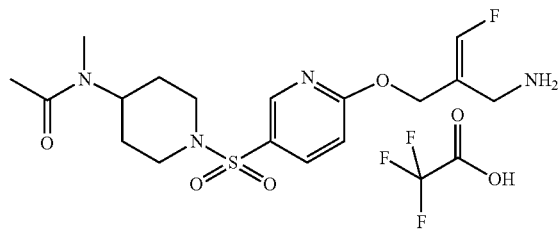 |
| 21 | 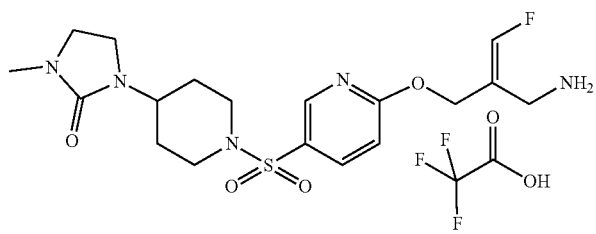 |
| 22 | 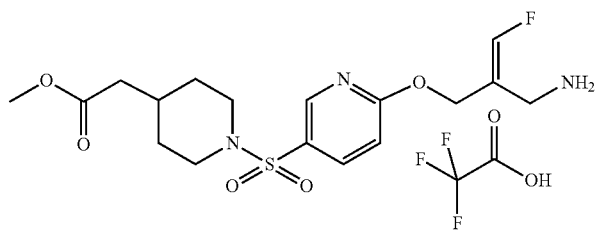 |
| 23 | 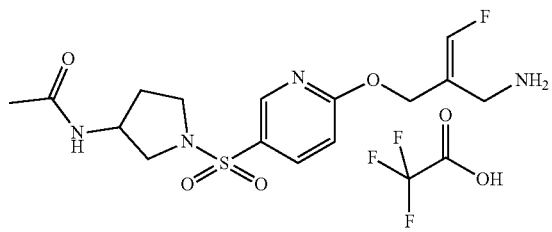 |
| 24 | 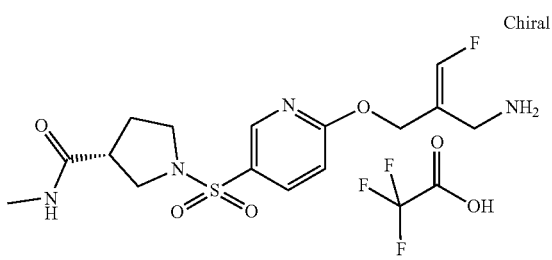 |
| 25 | 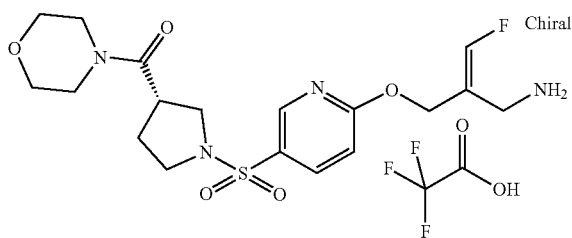 |

-continued

| # | structure |
|---|---|
| 26 | 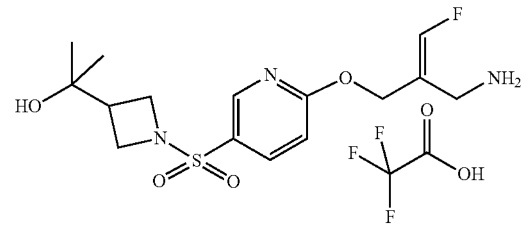 |
| 27 | Chiral |
| 28 | 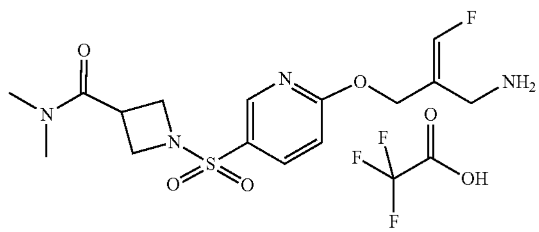 |
| 29 | Chiral |
| 30 | 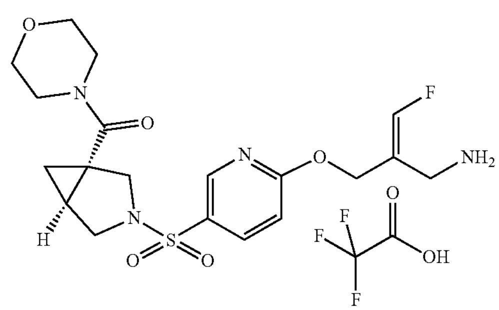 |
| 31 | 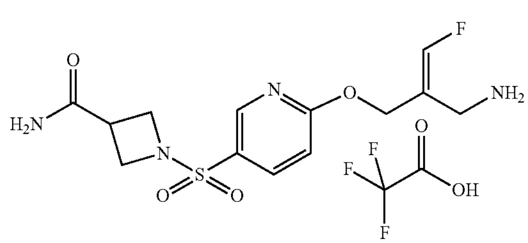 |

-continued

| # | structure |
|---|---|
| 32 | 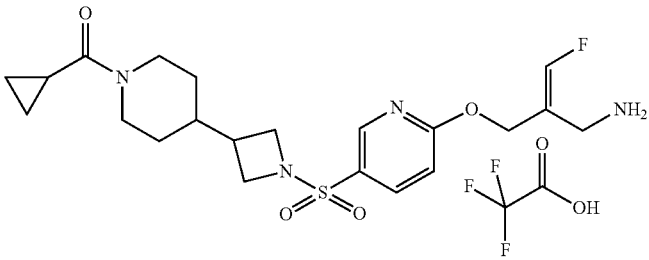 |
| 33 | 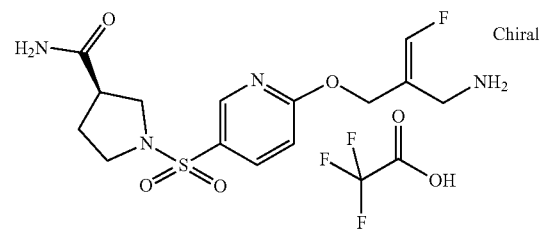 Chiral |
| 34 | 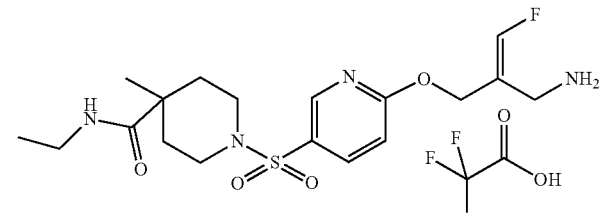 |

| | Substitution | | | | BOC deprotection | | |
|---|---|---|---|---|---|---|---|
| # | starting materials | R_t [min] (HPLC method) | MS | synthesis comment | R_t [min] (HPLC method) | MS | synthesis comment |
| 2 | II.2; IV.1 | 0.77 (HPLC-8) | 501 | S: THF/NMP B: 4.10 eq T: 0° C. to RT t: overnight purification: RP-HPLC (ACN/water + NH₄OH) | 0.40 (HPLC-7) | 401 | S: DCM A: 51 eq TFA T: RT t: 1 h |
| 3 | II.3; IV.1 | 0.61 (HPLC-1) | 485 | S: THF/NMP B: 4.00 eq T: RT t: 30 min workup: evaporation; no purification | 0.37 (HPLC-1) | 385 | S: DCM A: 13 eq TFA T: RT t: 1 h |
| 4 | II.4; IV.1 | 0.96 (HPLC-4) | 414 | S: THF/NMP B: 4.00 eq T: 0° C. to RT t: 2 h | 0.70 (HPLC-6) | 414 | S: DCM A: 23 eq TFA T: RT t: 2 h |
| 5 | II.5; IV.1 | 1.01 (HPLC-6) | 531 | S: DCM B: 4.00 eq T: RT t: 45 min | 0.69 (HPLC-6) | 431 | S: DCM A: 6 eq TFA T: RT t: 2 h |
| 6 | II.6; IV.1 | 0.74 (HPLC-8) | 487 | S: THF/NMP B: 4.10 eq T: 0° C. to RT t: overnight purification: RP-HPLC | 0.36 (HPLC-7) | 387 | S: DCM A: 51 eq TFA T: RT t: 1 h |

-continued

| # | starting materials | Substitution R_t [min] (HPLC method) | MS | synthesis comment | BOC deprotection R_t [min] (HPLC method) | MS | synthesis comment |
|---|---|---|---|---|---|---|---|
| 7 | II.7; IV.1 | 0.71 (HPLC-8) | 502 | S: THF/NMP B: 4.10 eq T: 0° C. to RT t: overnight purification: RP-HPLC (ACN/water + NH$_4$OH) | 0.36 (HPLC-7) | 402 | S: DCM A: 51 eq TFA T: RT t: 1 h |
| 8 | II.8; IV.1 | 0.94 (HPLC-4) | 402 | S: THF/NMP B: 4.00 eq T: 0° C. to RT t: 2 h | 0.68 (HPLC-6) | 402 | S: DCM A: 14 eq TFA T: RT t: 2 h |
| 9 | II.9; IV.1 | 1.15 (HPLC-6) | 519 | S: THF/DMSO B: 1.05 eq T: 0° C. to RT t: 80 min h | 0.84 (HPLC-6) | 519 | S: DCM A: 7 eq TFA T: RT t: 2 h |
| 10 | II.10;IV.1 | 1.07 (HPLC-6) | 443 | S: THF/DMSO B: 1.05 eq T: 0° C. to RT t: 35 min h | 0.72 (HPLC-6) | 443 | S: DCM A: 26 eq TFA T: RT |
| 11 | II.11.IV.1 | 1.07 (HPLC-6) | 401 | S: THF/DMSO B: 1.05 eq T: 0° C. to RT t: 40 min | 0.71 (HPLC-6) | 401 | S:DCM A: 8 eq TFA T: RT |
| 12 | II.12; IV.1 | 1.08 (HPLC-6) | 401 | S: THF/DMSO B: 1.05 eq T: 0° C. to RT t: 40 min | 0.71 (HPLC-6) | 401 | S: DCM A: 25 eq TFA T: RT |
| 13 | II.13; IV.1 | 0.77 (HPLC-8) | 513 | S: THF/NMP B: 4.10 eq T: 0° C. to RT t: overnight purification: RP-HPLC (ACN/water + NH$_4$OH) | 0.40 (HPLC-7) | 413 | S: DCM A: 51 eq TFA T: RT t: 1 h |
| 14 | II.14; IV.1 | | | S: DCM B: 6.00 eq T: 0° C. to RT t: 2 d workup: aq. extraction; no purification | 0.38 (HPLC-2) | 427 | S: DCM A: 5 eq TFA T: RT t: overnight |
| 15 | II.15; IV.1 | 0.77 (HPLC-8) | 513 | S: THF/NMP B: 4.10 eq T: 0° C. to RT t: overnight purification: RP-HPLC (ACN/water + NH$_4$OH) | 0.37 (HPLC-7) | 401 | S: DCM A: 51 eq TFA T: RT t: 1 h |
| 16 | II.16; IV.1 | 1.05 (HPLC-6) | 515 | S: THF/NMP T: 0° C. to RT t: 2 h | 0.74 (HPLC-6) | 415 | S: DCM A: 44 eq TFA T: RT t: 2 h |
| 17 | II.17; IV.1 | 0.97 (HPLC-6) | 373 | S: THF/DMSO B: 1.05 eq T: 0° C. to RT t: 35 min | 0.66 (HPLC-6) | 373 | S. DCM A: 19 eq TFA T: RT t: 1 h |
| 18 | II.18; IV.1 | 0.74 (HPLC-8) | 432 | S: THF/NMP B: 4.10 eq T: 0° C. to RT t: overnight purification: | 0.34 (HPLC-7) | 332 | S: DCM A: 51 eq TFA T: RT t: 1 h |

-continued

| | | Substitution | | | BOC deprotection | | |
|---|---|---|---|---|---|---|---|
| # | starting materials | $R_t$ [min] (HPLC method) | MS | synthesis comment | $R_t$ [min] (HPLC method) | MS | synthesis comment |
| 19 | II.19; IV.1 | 0.78 (HPLC-8) | 515 | RP-HPLC (ACM/water + NH₄OH) S: THF/NMP B: 4.10 eq T: 0° C. to RT t: overnight purification: RP-HPLC (ACN/water + NH₄OH) | 0.41 (HPLC-7) | 415 | S: DCM A: 51 eq TFA T: RT t: 1 h |
| 20 | II.20; IV.1 | 0.76 (HPLC-8) | 501 | S: THF/NMP B: 4.10 eq T: 0° C. to RT t: overnight purification: RP-HPLC (ACN/water + NH₄OH) | 0.40 (HPLC-7) | 401 | S: DCM A: 51 eq TFA T: RT t: 1 h |
| 21 | II.21: IV.1 | 1.05 (HPLC-6) | 528 | S: THF/NMP B: 4.00 eq T: 0° C. to RT t: 2 h | 0.73 (HPLC-6) | 428 | S: DCM A: 44 eq TFA T: RT t: 1 h |
| 22 | II.22; IV.1 | 0.71 (HPLC-1) | 502 | S: Tol B: 2.50 eq as a solid T: 0° C. to RT t: 3 h workup: aq. acidic extraction; purification by RP-HPLC (ACN/water + TFA) | 0.44 (HPLC-1) | 402 | S: 1.4-dioxane A: 60 eq HCl T: RT t: 1 h |
| 23 | II.23;IV.1 | 0.98 (HPLC-6) | 473 | S: THF/NMP B: 3.00 eq T: 0° C. to RT t: overnight | 0.64 (HPLC-6) | 373 | S: DCM A: 44 eq TFA T: RT t: 1 h |
| 24 | II.24; IV.1 | 1.00 (HPLC-6) | 473 | S: DCM B: 4.00 eq T: RT t: overnight | 0.65 (HPLC-6) | 373 | S: DCM A: 30 eq TFA T: RT t: 1 h |
| 25 | II.25; IV.1 | 1.04 (HPLC-6) | 529 | S: THF/DMSO B: 4.10 eq T: 0° C. to RT t: 1.5 h | 0.70 (HPLC-6) | 429 | S: DCM A: 7 eq TFA T: RT |
| 26 | II.26; IV.1 | 0.87 (HPLC-8) | 460 | S: THF/NMP B: 4.10 eq T: 0° C. to RT t: overnight purification RP-HPLC (ACN/water + NH₄OH) | 0.38 (HPLC-7) | 360 | S: DCM A: 51 eq TFA T: RT t: 1 h |
| 27 | II.27; IV.1 | 1.04 (HPLC-6) | 487 | S: THF/DMSO B: 4.10 eq T: 0° C. to RT t: 1.5 h | 0.70 (HPLC-6) | 387 | S: DCM A: 9 eq TFA T: RT t: 75 min |
| 28 | II.28: IV.1 | 1.03 (HPLC-6) | 473 | S: THF/DMSO B: 4.10 eq T: 0° C. to RT t: 1.5 h | 0.67 (HPLC-6) | 373 | S: DCM A: 9 eq TFA T: RT |
| 29 | II.29; IV.1 | 1.01 (HPLC-6) | 473 | S.THF/DMSO B: 4.10 eq T: 0° C. to RT t: 1.5 h | 0.66 (HPLC-6) | 373 | S: DCM A: 11 eq TFA T: RT |
| 30 | II.30; IV.1 | 0.63 (HPLC-1) | 541 | S: THF B: 4.00 eq T: RT | 0.43 (HPLC-1) | 441 | S: DCM A: 13 eq TFA |

| # | starting materials | Substitution R_t [min] (HPLC method) | MS | synthesis comment | BOC deprotection R_t [min] (HPLC method) | MS | synthesis comment |
|---|---|---|---|---|---|---|---|
| | | | | t: 40 min | | | T: RT t: 2 h |
| 31 | II:31; IV.1 | 0.97 (HPLC-6) | 445 | S:THF/DMSO B: 4.10 eq T: 0° C. to RT t: 2.5 h | 0.62 (HPLC-6) | 345 | S: DCM A: 60 eq TFA T: RT |
| 32 | II:32; IV.1 | 0.84 (HPLC-8) | 553 | S: THF/NMP B: 4.10 eq t: overnight purification RP-HPLC (ANC/water + NH_4OH) | 0.49 (HPLC-7) | 453 | S: DCM A: 51 eq TFA T: RT t: 1 h |
| 33 | II.33; IV.1 | 0.96 (HPLC-6) | 459 | S: DMSO B: 1.05 eq T: RT t: overnight | 0.63 (HPLC-6) | 359 | S: DCM A: 18 eq TFA T: RT t: 2 h |
| 34 | 11.34: IV.1 | 1.07 (HPLC-6) | 515 | S: THF/DMSO/ DCM B: 4.00 eq T: RT t: overnight | 0.74 (HPLC-6) | 415 | S: DCM A: 5 eq TFA T: RT t: 2 h |

Example 35: (S)-1-[6-((E)-2-Aminomethyl-3-fluoro-allyloxy)-pyridine-3-sulfonyl]-pyrrolidin-3-ol Substitution:

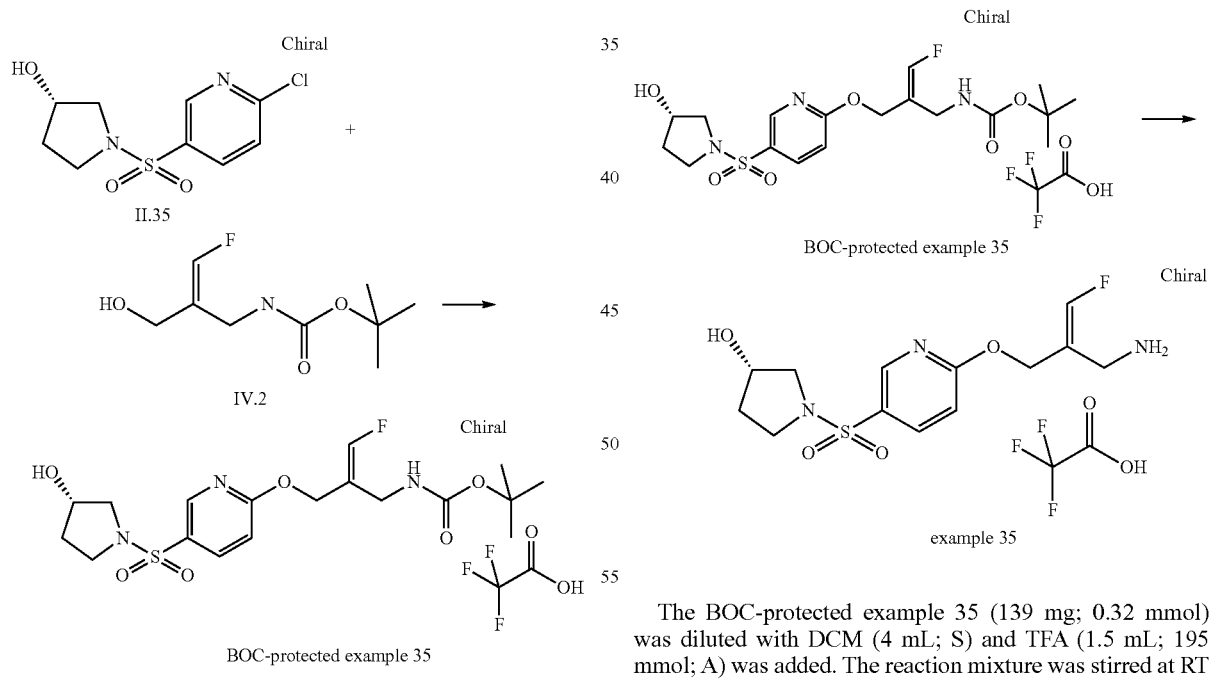

BOC-protected example 35 example 35

Intermediate IV.2 (176 mg; 0.86 mmol) was diluted with THF (6 mL; S) and sodium hydride (55%; 75 mg; 1.72 mmol; B) was added at RT. After stirring at RT (T) for 10 min (t) intermediate II.35 (226 mg; 0.86 mmol) was added. The reaction mixture was stirred at RT (T) overnight (t) and purified by RP-HPLC (ACN/water+TFA) to give the BOC-protected example 35.

Yield: 139 mg (38%), ESI-MS: m/z=432 [M+H]$^+$, R_t (HPLC): 0.63 min (HPLC-2)

Boc Deprotection:

The BOC-protected example 35 (139 mg; 0.32 mmol) was diluted with DCM (4 mL; S) and TFA (1.5 mL; 195 mmol; A) was added. The reaction mixture was stirred at RT (T) for 3 h (t) and purified by RP-HPLC (ACN/water+TFA) to give example 35.

Yield: 103 mg (27%), ESI-MS: m/z=332 [M+H]$^+$, R_t (HPLC): 0.62 min (HPLC-6)

The following examples (example number given in column #) were prepared in analogy to the above described procedure using the corresponding starting materials. Details for the two steps are given in the column synthesis comment, the retention-time and mass (ESI-MS, m/z=[M+H]$^+$) determined by HPLC-MS are given in the columns R$_t$ and MS.

| # | structure |
|---|---|
| 36 | (Chiral) structure with (3R)-3-hydroxypyrrolidine sulfonyl pyridine, fluoroallyl ether, CH$_2$NH$_2$, TFA salt |
| 37 | 3,3-difluoroazetidine sulfonyl pyridine, fluoroallyl ether, CH$_2$NH$_2$, TFA salt |
| 38 | pyrrolidine sulfonyl pyridine, fluoroallyl ether, CH$_2$NH$_2$, TFA salt |
| 39 | azetidine sulfonyl pyridine, fluoroallyl ether, CH$_2$NH$_2$, TFA salt |
| 40 | 3-methoxypyrrolidine sulfonyl pyridine, fluoroallyl ether, CH$_2$NH$_2$, TFA salt |
| 41 | 3-azabicyclo[3.1.0]hexane sulfonyl pyridine, fluoroallyl ether, CH$_2$NH$_2$, TFA salt |
| 42 | 3-methoxyazetidine sulfonyl pyridine, fluoroallyl ether, CH$_2$NH$_2$, TFA salt |
| 43 | 3,3-difluoropyrrolidine sulfonyl pyridine, fluoroallyl ether, CH$_2$NH$_2$, TFA salt |

| | | Substitution | | | BOC deprotection | | |
|---|---|---|---|---|---|---|---|
| # | starting materials | R$_t$ [min] (HPLC method) | MS | synthesis comment | R$_t$ [min] (HPLC method) | MS | synthesis comment |
| 36 | II.36; IV.2 | 0.63 (HPLC-2) | 432 | S: THF B: 2.00 eq T: RT t: overnight | 0.62 (HPLC-6) | 332 | S: DCM A: 9 eq TFA T: RT t: 3 h |
| 37 | II.37; IV.2 | | | S: DMF B: 1.00 eq T: RT t: 2 h; intermediate not isolated | 0.34 (HPLC-1) | 338 | S: DCM A: 42 eq TFA T: RT t: 2 h |

-continued

| # | Substitution starting materials | R$_t$ [min] (HPLC method) | synthesis MS comment | BOC deprotection R$_t$ [min] (HPLC method) | MS | synthesis comment |
|---|---|---|---|---|---|---|
| 38 | IV.2 | | S: DMF<br>B: 1.00 eq<br>T: RT<br>t: 2 h;<br>intermediate not isolated | 0.34<br>(HPLC-3) | 316 | S: DCM<br>A: 42 eq TFA<br>T: RT<br>t: 2 h |
| 39 | II.38;<br>IV.2 | | S: DMF<br>B: 2.00 eq<br>T: RT<br>t: 2 h;<br>intermediate not isolated | 0.39<br>(HPLC-1) | 302 | S: DCM<br>A: 37 eq TFA<br>T: RT<br>t: 1 h |
| 40 | II.39;<br>IV.2 | | S: DMF<br>B: 2.00 eq<br>T: RT<br>t: 2 h;<br>intermediate not isolated | 0.33<br>(HPLC-1) | 346 | S: DCM<br>A: 43 eq TFA<br>T: RT<br>t: 2 h |
| 41 | II.40;<br>IV.2 | | S: DMF<br>B: 2.00 eq<br>T: RT<br>t: 2 h;<br>intermediate not isolated | 0.38<br>(HPLC-1) | 328 | S: DCM<br>A: 2 eq TFA<br>T: RT<br>t: 2 h |
| 42 | II.41;<br>IV.2 | | S: DMF<br>B: 2.00 eq<br>T: RT<br>t: 2 h;<br>intermediate not isolated | 0.36<br>(HPLC-1) | 332 | S: DCM<br>A: 41 eq TFA<br>T: RT<br>t: 2 h |
| 43 | II.42;<br>IV.2 | | S: DMF<br>B: 2.00 eq<br>T: RT<br>t: 2 h;<br>intermediate not isolated | 0.40<br>(HPLC-1) | 352 | S: DCM<br>A: 44 eq TFA<br>T: RT<br>t: 1 h |

Example 44: 1-[6-((E)-2-Aminomethyl-3-fluoro-allyloxy)-pyridine-3-sulfonyl]-piperidine-4-carboxylic acid methylamide trifluoroacetate Substitution:

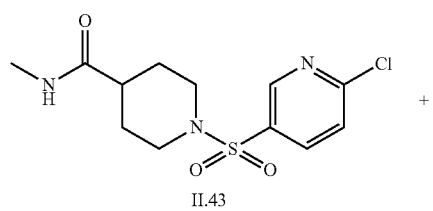

II.43

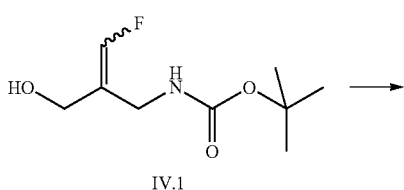

IV.1

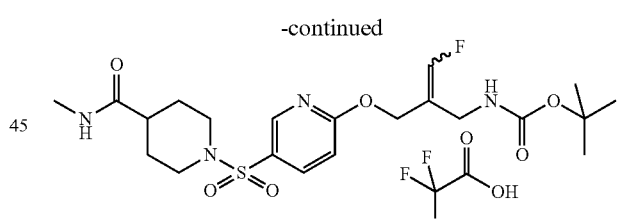

BOC-protected example 44

Intermediate IV.1 (70 mg; 0.34 mmol) was dissolved in THF (1 ml; S) and sodium hydride (55%; 30 mg; 0.68 mmol; B) was added. After stirring at RT (T) for 10 min (t) intermediate II.43 (108 mg; 0.34 mmol) was added and the reaction mixture was stirred at RT (T) overnight (t). The reaction mixture was purified by RP-HPLC (ACN/water+ TFA) to give the BOC-protected example 44.

Yield: 95 mg (57%), ESI-MS: m/z=487 [M+H]$^+$, R$_t$ (HPLC): 0.64 min (HPLC-2)

Boc Deprotection:

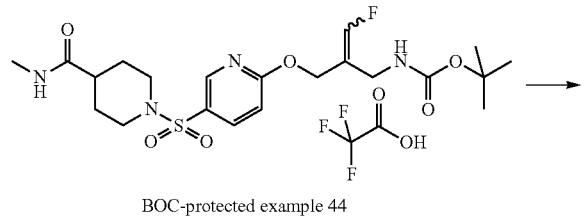

BOC-protected example 44

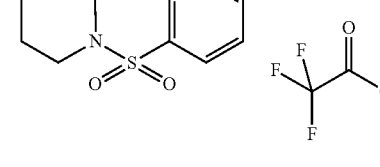

example 44

The BOC-protected example 44 as E/Z-mixture (95 mg; 0.20 mmol) was diluted with DCM (4 mL; S) and TFA (1.5 mL; 19.47 mmol; A) was added. The reaction mixture was stirred at RT (T) for 3.3 h (t) and purified by RP-HPLC (ACN/water+TFA) to give example 44.

Yield: 44 mg (26%), ESI-MS: m/z=387 [M+H]$^+$, $R_t$ (HPLC): 0.66 min (HPLC-6)

The following examples (example number given in column #) were prepared in analogy to the above described procedure using the corresponding starting materials. Details for the two steps are given in the column synthesis comment, the retention-time and mass (ESI-MS, m/z=[M+H]$^+$) determined by HPLC-MS are given in the columns $R_t$ and MS.

| # | structure |
|---|---|
| 45 | 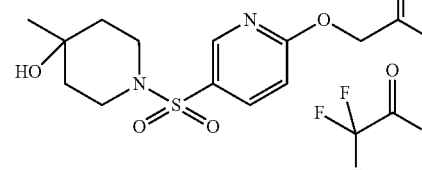 |
| 46 | 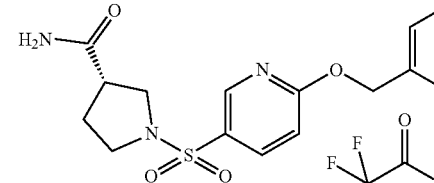 |
| 47 | 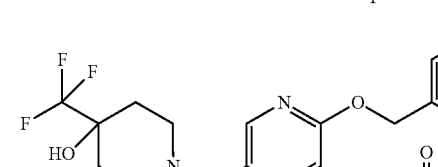 |
| 48 | 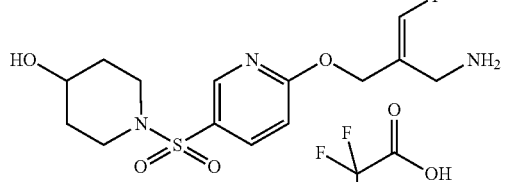 |
| 49 | 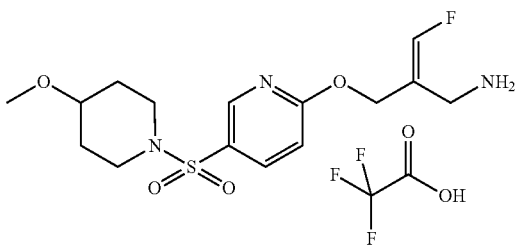 |
| 50 | (structure) |

| | | Substitution | | | BOC deprotection | | |
|---|---|---|---|---|---|---|---|
| # | starting materials | $R_t$ [min] (HPLC method) | MS | synthesis comment | $R_t$ [min] (HPLC method) | MS | synthesis comment |
| 45 | II.44; IV.1 | 0.65 (HPLC-2) | 446 | S: THF<br>B: 2.00 eq<br>T: RT<br>t: overnight | 0.65 (HPLC-6) | 346 | S: DCM<br>A: 26 eq<br>TFA<br>T: RT<br>t: overnight |
| 46 | II.45; IV.1 | | | S: THF<br>B: 2.00 eq<br>T: RT<br>t: 2 h;<br>intermediate not isolated | 0.37 (HPLC-1) | 360 | S: DCM<br>A: 46 eq<br>TFA<br>T: RT<br>t: 2 h |
| 47 | II.46; IV.1 | | | S: THF<br>B: 2.00 eq<br>T: RT<br>t: 2 h;<br>intermediate not isolated | 0.40 (HPLC-1) | 330 | S: DCM<br>A: 41 eq<br>TFA<br>T: RT<br>t: 2 h |
| 48 | II.47; IV.1 | 0.68 (HPLC- | 460 | S: THF<br>B: 2.00 eq | 0.70 (HPLC- | 360 | S: DCM<br>A: 19 eq |

-continued

| | | Substitution | | BOC deprotection | |
|---|---|---|---|---|---|
| # | starting materials | $R_t$ [min] (HPLC method) | synthesis MS comment | $R_t$ [min] (HPLC method) | synthesis MS comment |
| | | 2) | T: RT<br>t: overnight | 6) | TFA<br>T: RT<br>t: 1 h |
| 49 | II.48; IV.1 | 0.61<br>(HPLC-2) | 459 S: THF<br>B: 2.00 eq<br>T: RT<br>t: overnight | 0.62<br>(HPLC-6) | 359 S: DCM<br>A: 35 eq<br>TFA<br>T: RT<br>t: 1 h |
| 50 | II.49; IV.1 | 0.75<br>(HPLC-2) | 514 S: THF<br>B: 2.00 eq<br>T: RT<br>t: overnight | 0.62<br>(HPLC-6) | 414 S: DCM<br>A: 24 eq<br>TFA<br>T: RT<br>t: 2 h |

Example 51: 1-[6-((E)-2-Aminomethyl-3-fluoro-allyloxy)-pyridine-3-sulfonyl]-piperidine-4-carboxylic acid methyl ester trifluoroacetate Substitution:

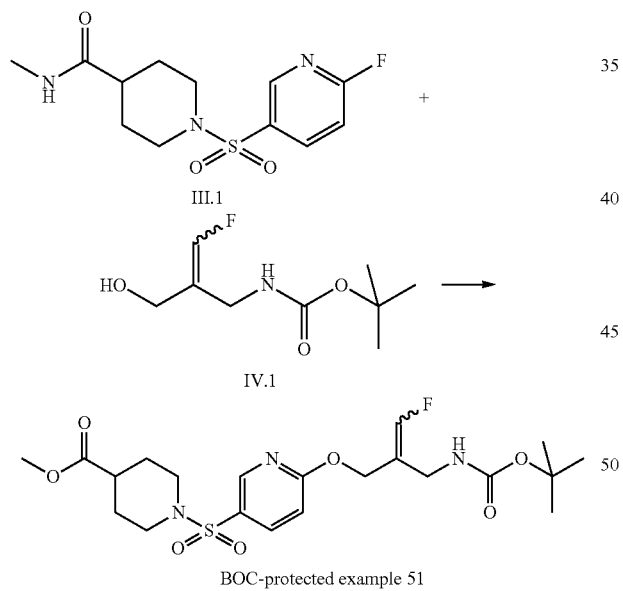

Intermediate IV.1 (70 mg; 0.33 mmol) was dissolved in Tol (3 mL; S) and sodium tert-butoxide (30 mg; 0.33 mmol; B) was added. To the reaction mixture intermediate III.1 (100 mg; 0.33 mmol) was added and the reaction mixture was stirred at RT (T) for 35 min (t). Toluene was evaporated under reduced pressure, the residue taken up in MeOH (3 mL) and purified by RP-HPLC (ACN/water+TFA) to give the BOC-protected example 51.

Yield: 97 mg (60%), ESI-MS: m/z=488 [M+H]$^+$, $R_t$ (HPLC): 0.69 min (HPLC-1)

Boc Deprotection:

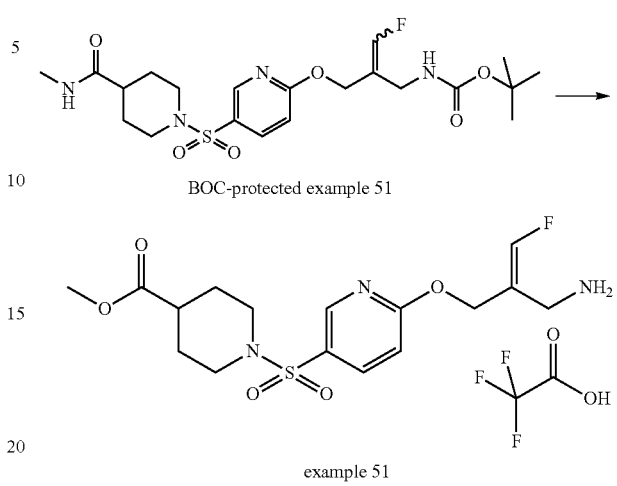

The BOC-protected example 51 (50 mg; 0.10 mmol) was diluted with DCM (4 mL; S) and TFA (30 µL; 0.41 mmol; A) was added. The reaction mixture was stirred at RT (T) over the weekend (t). Then it was evaporated in vacuo, the residue taken up with MeOH (3 mL) and purified by RP-HPLC (ACN/water+TFA) to give example 51.

Yield: 16 mg (31%), ESI-MS: m/z=388 [M+H]$^+$, $R_t$ (HPLC): 0.4 min (HPLC-1)

The following examples (example number given in column #) were prepared in analogy to the above described procedure using the corresponding starting materials. Details for the two steps are given in the column synthesis comment, the retention-time and mass (ESI-MS, m/z=[M+H]$^+$) determined by HPLC-MS are given in the columns $R_t$ and MS.

| # | structure |
|---|---|
| 52 | (structure shown) |
| 53 | (structure shown) |

| # | starting materials | R$_t$ [min] (HPLC method) | Substitution MS | synthesis comment | R$_t$ [min] (HPLC method) | BOC deprotection MS | synthesis comment |
|---|---|---|---|---|---|---|---|
| 52 | III.2; IV.1 | 0.69 (HPLC-1) | 486 | S: Tol B: 1.00 eq T: RT t: 70 min; workup: extraction; purification: column chromatography on silica | 0.43 (HPLC-1) | 386 | S: DCM A: 2 eq TFA T: RT t: overnight |
| 53 | III.3; IV.1 | 072 (HPLC-1) | 502 | S: Tol B: 1.00 eq T: RT t: 70 min; workup: extraction; purification column chromatography on silica | 0.48 (HPLC-1) | 402 | S: DCM A: 4 eq TFA T: RT t: 2 h |

Intermediate V.1: {1-[6-(2-Aminomethyl-3-fluoro-allyloxy)-pyridine-3-sulfonyl]-piperidin-4-yl}-acetic acid methyl ester (E/Z-mixture)

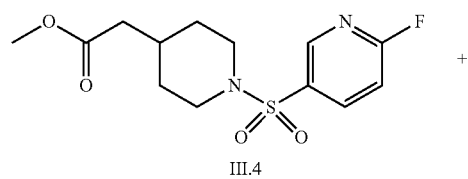

III.4

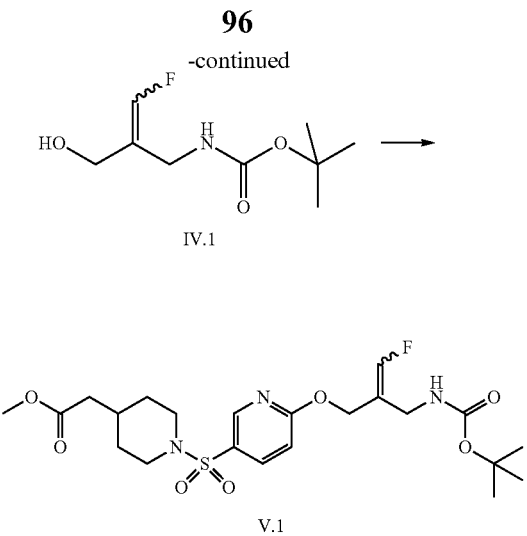

IV.1

V.1

The alcohol IV.1 (0.95 g; 4.62 mmol) was dissolved in toluene (30 mL) and sodium tert-butoxide (0.44 g; 4.62 mmol) and intermediate III.4 (1.46 g; 4.62 mmol) were added. The reaction mixture was stirred at RT for 2 h, diluted with toluene (30 mL) and extracted with water two times. The organic phase was dried with Na$_2$SO$_4$ and evaporated under reduced pressure. The residue was purified by silica gel chromatography to provide intermediate V.1.

Yield: 1.85 g (80%), ESI-MS: m/z=502 [M+H]$^+$, Rc (HPLC): 0.72 min (HPLC-1)

The following intermediates were prepared in analogy to the above described procedure using the alcohol IV.1 and the corresponding starting material. For changes from this procedure, see "synthesis comment".

| intermediate | structure | starting material | R$_t$ [min] (HPLC method) | MS | synthesis comment |
|---|---|---|---|---|---|
| V.2 | 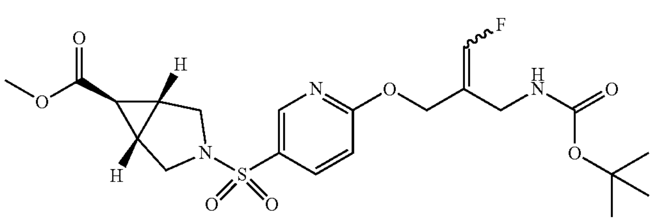 [SMILES: COC(=O)[C@H]1[C@@H]2CN(S(=O)(=O)c3ccc(OCC(=CF)CNC(=O)OC(C)(C)C)nc3)C[C@@H]21] | III.2 | 0.69 (HPLC-1) | 486 | 1 h |
| V.3 | 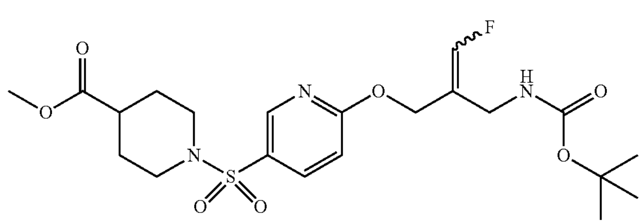 [SMILES: COC(=O)C1CCN(S(=O)(=O)c2ccc(OCC(=CF)CNC(=O)OC(C)(C)C)nc2)CC1] | III.1 | 0.71 (HPLC-1) | 488 | workup: recrystallization with PE/EtOAC (3:1) |

| intermediate | structure | starting material | R$_t$ [min] (HPLC method) | MS | synthesis comment |
|---|---|---|---|---|---|
| V.4 | 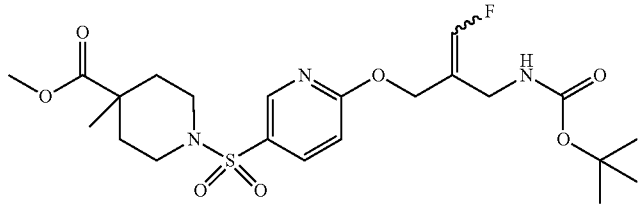 [SMILES: COC(=O)C1(C)CCN(S(=O)(=O)c2ccc(OCC(=CF)CNC(=O)OC(C)(C)C)nc2)CC1] | III.3 | 0.72 (HPLC-1) | 502 | 70 min |

Intermediate VI.1: {1-[6-(2-Aminomethyl-3-fluoro-allyloxy)-pyridine-3-sulfonyl]-piperidin-4-yl}-acetic acid (E/Z-mixture)

Intermediate V.1 (1.85 g; 3.69 mmol) was dissolved in MeOH (70 mL) and aq. NaOH (1 N; 22.13 mL; 22.13 mmol) was added. The reaction mixture was stirred at RT for 10 min, then acidified with citric acid (10%) and MeOH was evaporated under reduced pressure. The residue was cooled to 5° C., the precipitate was filtered, washed with water (10 mL) and dried at 4000 to give intermediate VIA.

Yield: 1.31 g (73%), ESI-MS: m/z=488 [M+H]$^+$, Rc (HPLC): 0.62 min (HPLC-1)

The following intermediates were prepared in analogy to the above described procedure using the corresponding starting material. For changes from this procedure, see "synthesis comment".

| intermediate | structure | starting material | R$_t$ [min] (HPLC method) | MS | synthesis comment |
|---|---|---|---|---|---|
| VI.2 | 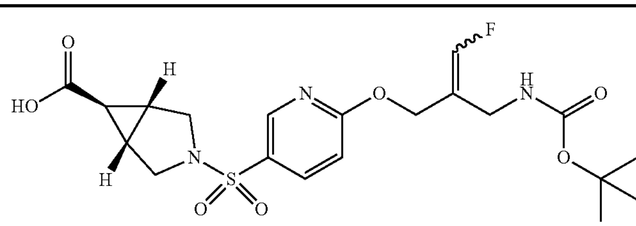 | V.2 | 0.62 (HPLC-1) | 472 | 4 eq NaOH; 18 h |
| VI.3 | 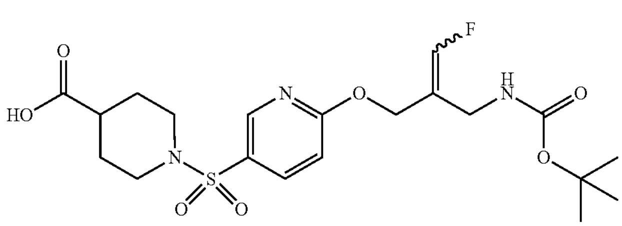 [SMILES: CC(C)(C)OC(=O)NCC(=CF)COc1ccc(S(=O)(=O)N2CCC(C(=O)O)CC2)cn1] | V.3 | 0.62 (HPLC-1) | 474 | 4 eq NaOH; 3 h |

| intermediate | structure | starting material | $R_t$ [min] (HPLC method) | MS | synthesis comment |
|---|---|---|---|---|---|
| VI.4 | 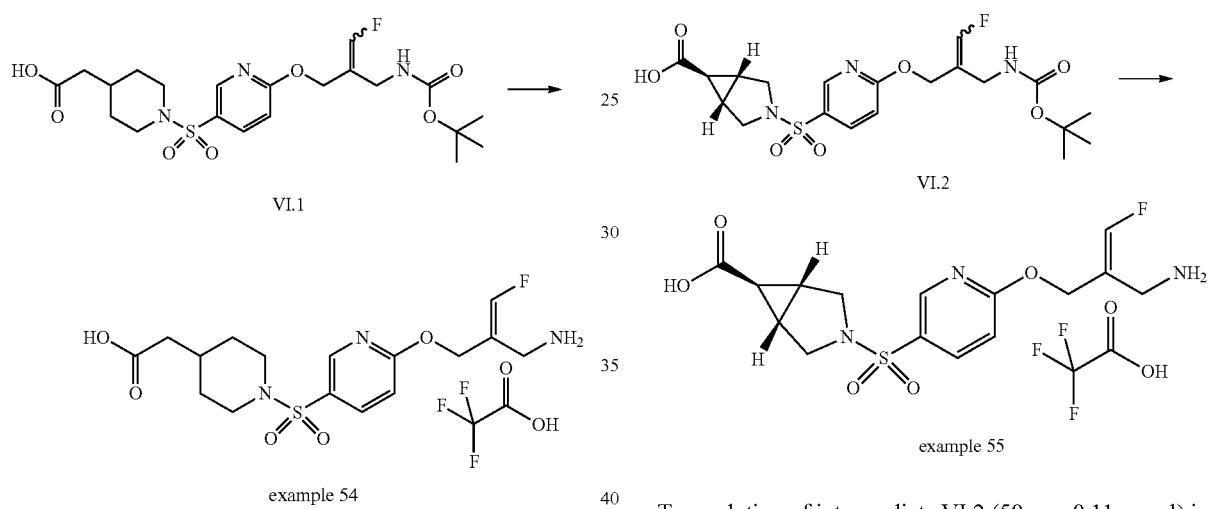 | V.4 | 0.63 (HPLC-1) | 487 | 7.2 eq NaOH; 2 d |

Example 54 {1-[6-((E)-2-Aminomethyl-3-fluoro-allyloxy)-piperidine-3-sulfonyl]piperidin-4-yl}-acetic acid trifluoroacetate Example 55 trans-3-[6-((E)-2-Aminomethyl-3-fluoro-allyloxy)-pyridine-3-sulfonyl]-3-aza-bicyclo[3.1.0]hexane-6-carboxylic acid trifluoroacetate Intermediate VI.1 (50 mg; 0.10 mmol) was dissolved in a solution of 4 N hydrogen chloride in 1,4-dioxane (1.5 mL; 6.00 mmol) and stirred at RT for 70 min. The reaction mixture was evaporated in vacuo. The residue was dissolved in MeOH (3 mL) and purified by RP-HPLC (ACN/water+TFA) to provide example 54.

Yield: 18 mg (35%), ESI-MS: m/z=388 [M+H]$^+$, $R_t$ (HPLC): 0.40 min (HPLC-1)

To a solution of intermediate VI.2 (50 mg; 0.11 mmol) in DCM (10 mL) was added TFA (50 mg; 0.42 mmol). The reaction mixture was stirred at RT for 50 min, evaporated in vacuo and the residue was purified by RP-HPLC (ACN/water+TFA) to provide example 55.

Yield: 14 mg (27%), ESI-MS: m/z=372 [M+H]$^+$, $R_t$ (HPLC): 0.40 min (HPLC-1)

The following examples were prepared in analogy to the above described procedure using the corresponding starting material. For changes from this procedure, see "synthesis comment".

| example | structure | starting material | $R_t$ [min] (HPLC method) | MS | synthesis comment |
|---|---|---|---|---|---|
| 56 | 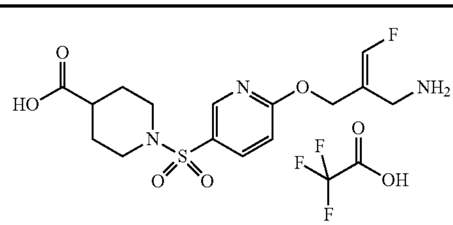 | VI.3 | 0.41 (HPLC-1) | 374 | 2 h |

| example | structure | starting material | $R_t$ [min] (HPLC method) | MS | synthesis comment |
|---|---|---|---|---|---|
| 57 | 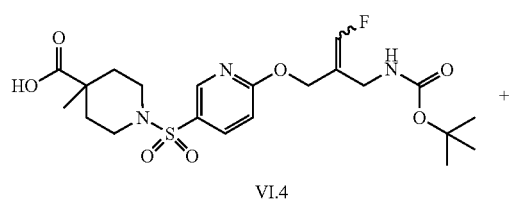 | VI.4 | 0.73 (HPLC-5) | 388 | 15.5 h |

Intermediate VII.1: (3-Fluoro-2-{5-[4-methyl-4-(tetrahydro-pyran-4-ylcarbamoyl)-piperidine-1-sulfonyl]-pyridine-2-yloxymethyl}-allyl)-carbamic acid tert-butyl ester (E/Z-mixture)

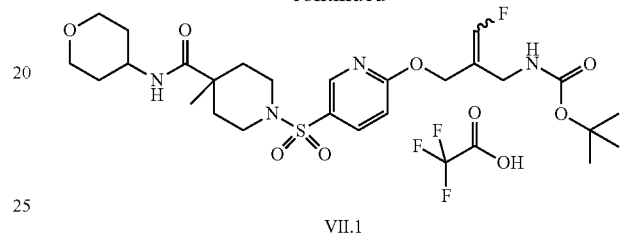

VII.1

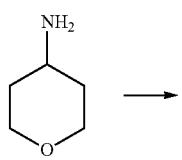

Intermediate VI.4 (40 mg; 0.08 mmol) was dissolved in DMF (2.00 mL) and TEA (46 µL; 0.33 mmol) and TCFH (23 mg; 0.08 mmol) were added. The reaction mixture was stirred at RT for 10 min and 4-aminotetrahydropyran (20 mg; 0.20 mmol) was added. The reaction mixture was stirred at RT overnight, then acidified with TFA (aq.; 50%) and purified by RP-HPLC (ACN/water+TFA) to provide intermediate VII.1.

Yield: 22 mg (47%), ESI-MS: m/z=471 [M+H]⁺, $R_t$ (HPLC): 1.05 min (HPLC-6)

The following intermediates were prepared in analogy to the above described procedure using corresponding starting materials.

| intermediate | structure | starting material | $R_t$ [min] (HPLC method) | MS |
|---|---|---|---|---|
| VII.2 | 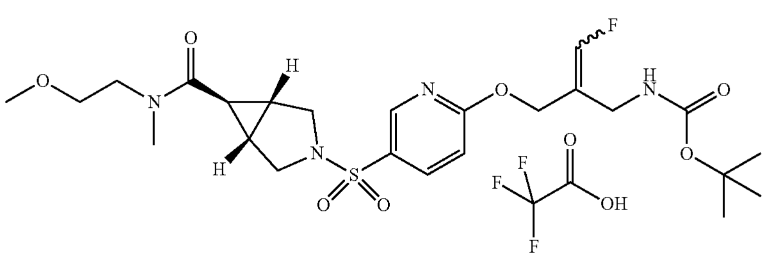 | VI.2 | 1.05 (HPLC-6) | 433 |

Intermediate VII.3: {2-[5-(4-Carbamoylmethyl-piperidine-1-sulfonyl)-pyridin-2-yloxymethyl]-3-fluoro-allyl}-carbamic acid tert-butyl ester (E/Z-mixture) trifluoroacetate

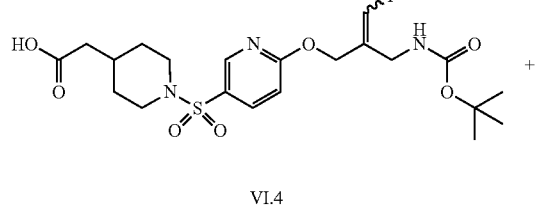

VI.4

+

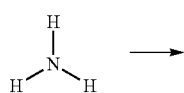

→

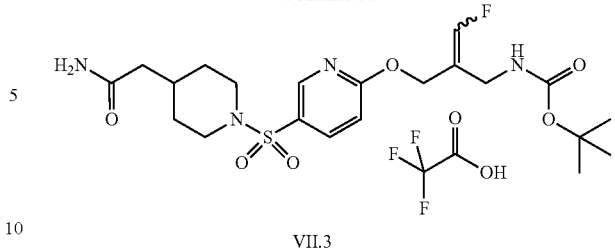

VII.3

To a solution of intermediate VI.1 (100 mg; 0.21 mmol) in DMF (1 mL) was added TEA (40 μL; 0.41 mmol) and HATU (90 mg; 0.23 mmol) at RT. Ammonia (0.5 M in 1,4-dioxane; 2 mL; 1.00 mmol) was added to the reaction mixture and it was stirred at RT for 1 h 40 min. The reaction mixture was diluted with water and extracted with EtOAc. The pooled organic phases were dried with $Na_2SO_4$ and evaporated. The crude material was taken up in MeOH (3 mL) and purified by RP-HPLC (ACN/water+TFA) to provide intermediate VII.3.

Yield: 70 mg (70%), ESI-MS: m/z=486 $[M+H]^+$, $R_t$ (HPLC): 0.58 min (HPLC-1)

The following intermediates were prepared in analogy to the above described procedure using the corresponding starting materials. For changes from this procedure, see "synthesis comment".

| intermediate | structure | starting materials | $R_t$ [min] (HPLC method) | MS | synthesis comment |
|---|---|---|---|---|---|
| VII.4 | 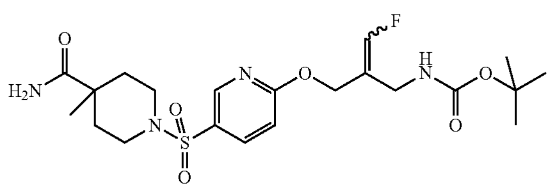 [SMILES: CC(C)(C)OC(=O)NCC(=CF)COc1ccc(S(=O)(=O)N2CCC(C)(C(N)=O)CC2)cn1] | $NH_3$, $HO-C(=O)-OH$ with $NH_3$; VI.4 | 0.96 (HPLC-4) | 387 | 5 eq amine; 8 eq TEA; overnight; workup: no extraction purification: RP-HPLC (ACN/water + $NH_4OH$) |
| VII.5 | 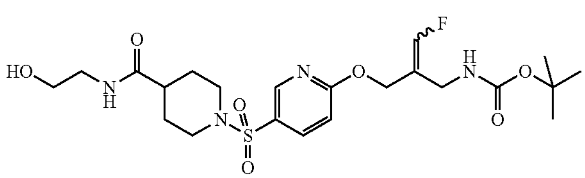 [SMILES: CC(C)(C)OC(=O)NCC(=CF)COc1ccc(S(=O)(=O)N2CCC(C(=O)NCCO)CC2)cn1] | cyclic ether-O-CH2CH2-$NH_2$; VI.3 | | 601 | 1.5 eq amine; 4.25 ea TEA; overnight; purification: RP-HPLC (ACN/water + $NH_4OH$) |
| VII.6 | 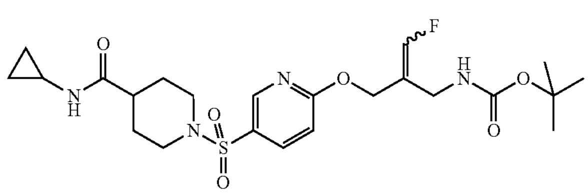 [SMILES: CC(C)(C)OC(=O)NCC(=CF)COc1ccc(S(=O)(=O)N2CCC(C(=O)NC3CC3)CC2)cn1] | cyclopropyl-$NH_2$; VI.3 | 0.77 (HPLC-8) | 513 | 1.5 eq amine; 4.25 ea TEA; overnight; purification: RP-HPLC (ACN/water + $NH_4OH$) |
| VII.7 | 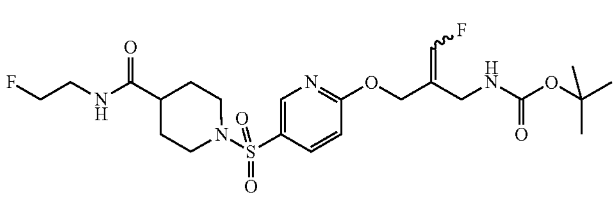 [SMILES: CC(C)(C)OC(=O)NCC(=CF)COc1ccc(S(=O)(=O)N2CCC(C(=O)NCCF)CC2)cn1] | F-CH2CH2-$NH_2$; HCl; VI.3 | 0.77 (HPLC-8) | 533 | 1.5 eq amine; 4.25 ea TEA; overnight; purification: RP-HPLC (ACN/water + $NH_4OH$) |

| intermediate | structure | starting materials | R_t [min] (HPLC method) | MS | synthesis comment |
|---|---|---|---|---|---|
| VII.8 | 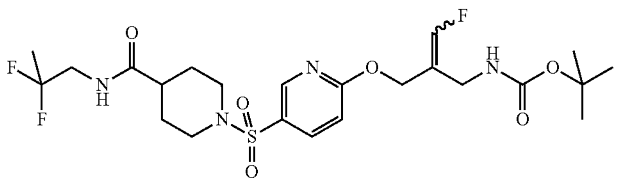 [SMILES: CC(F)(F)CNC(=O)C1CCN(S(=O)(=O)c2ccc(OCC(=CF)CNC(=O)OC(C)(C)C)nc2)CC1] | VI.3 | 0.83 (HPLC-8) | 565 | 1.5 eq amine; 4.25 ea TEA; overnight; purification: RP-HPLC (ACN/water + NH_4OH) |

Intermediate VII.9: (3-Fluoro-2-{5-[6-(2-methoxy-ethylcarbamoyl)-3-aza-bicyclo[3.1.0]hexane-3-sulfo-nyl]-pyridin-2-yloxymethyl}-allyl)-carbamic acid tert-butyl ester (E/Z-mixture)

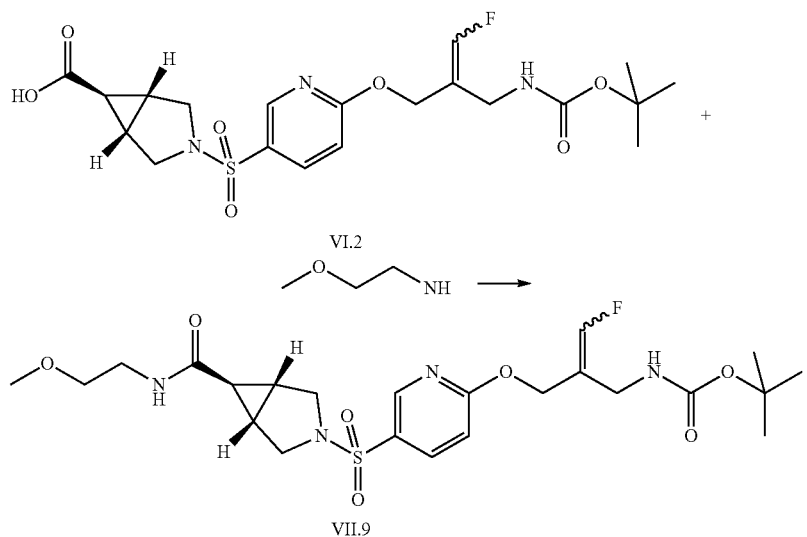

To the solution of intermediate VI.2 (40 mg; 0.08 mmol), 2-methoxyethylamine (15 mg: 0.20 mmol) and N-methyl-morpholine (47 µL; 0.42 mmol) in DCM (2 mL) was added 1-propanephosphonic acid cyclic anhydride (50% in EtOAc; 100 µL; 0.17 mmol). The reaction mixture was stirred at RT overnight, treated with 1-propanephosphonic acid cyclic anhydride (50% in EtOAc; 50 µL; 0.09 mmol) again and stirred at RT overnight. The reaction mixture was dissolved in ACN/water and purified by RP-HPLC (ACN/water+ NH_4OH) to provide intermediate VII.9.

ESI-MS: m/z=552 [M+H]$^+$, R_t (HPLC): 0.75 min (HPLC-8)

Example 58: 1-[6-((E)-2-Aminomethyl-3-fluoro-allyloxy)-pyridine-3-sulfonyl]-4-methyl-piperidine-4-carboxylic acid (tetrahydropyran-4-yl)-amide trif-luoroacetate

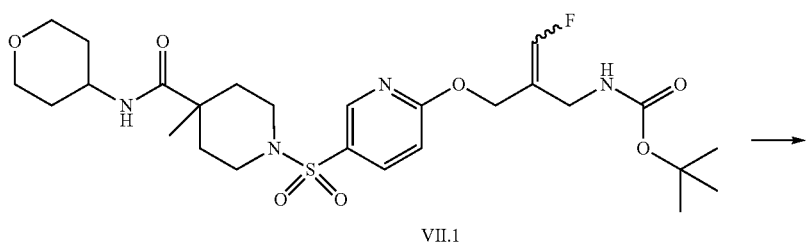

-continued

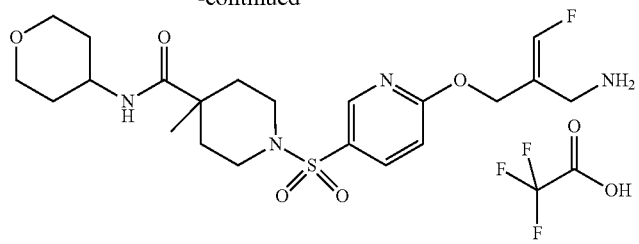

example 58

A solution of intermediate VII.1 (22 mg; 0.04 mmol) and TFA (1.00 mL; 12.96 mmol) in DCM (1 mL) was stirred at RT for 2 h, then evaporated to dryness under reduced pressure, acidified with TFA (50%) and purified by RP-HPLC (ACN/water+TFA) to provide example 58.

Yield: 13 mg (56%), ESI-MS: m/z=471 [M+H]$^+$, Rc (HPLC): 0.74 min (HPLC-6)

The following examples were prepared in analogy to the above described procedure using the corresponding starting material. For changes from this procedure, see "synthesis comment".

| example | structure | starting material | R$_t$ [min] (HPLC method) | MS | synthesis comment |
|---|---|---|---|---|---|
| 59 | 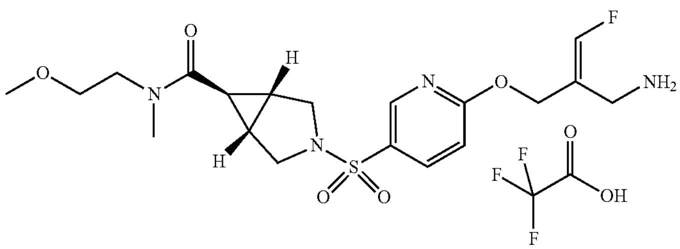 | VII.2 | 0.73 (HPLC-6) | 443 | exc. TFA |
| 60 | 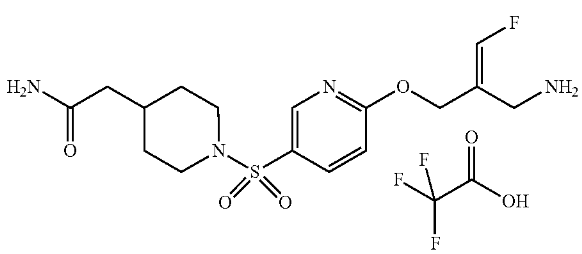 | VII.3 | 0.40 (HPLC-1) | 386 | 45 eq TFA; 100 min |
| 61 | 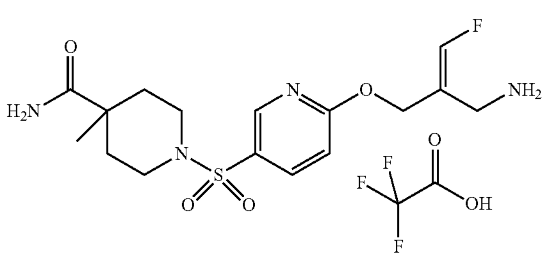 | VII.4 | 0.68 (HPLC-6) | 387 | exc. TFA |
| 62 | 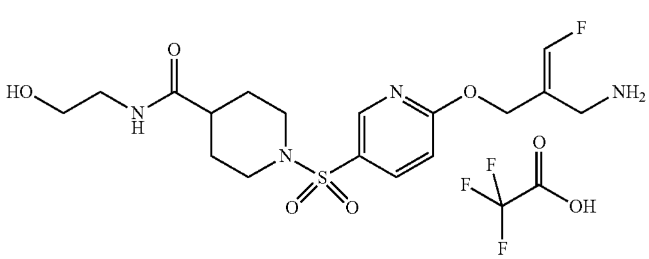 | VII.5 | 0.33 (HPLC-9) | 417 | 77 eq TFA; 1 h |

-continued

| example | structure | starting material | $R_t$ [min] (HPLC method) | MS | synthesis comment |
|---|---|---|---|---|---|
| 63 | 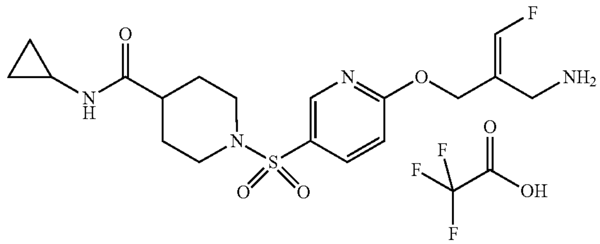 | VII.6 | 0.40 (HPLC-9) | 413 | 77 eq TFA; 1 h |
| 64 | 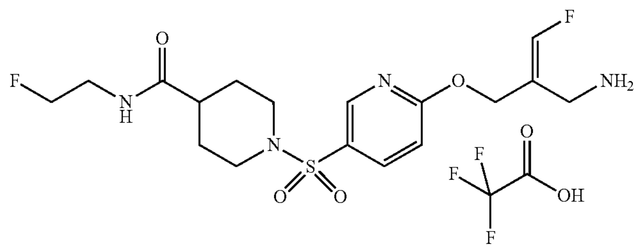 | VII.7 | 0.42 (HPLC-9) | 419 | 77 eq TFA; 1 h |
| 65 | 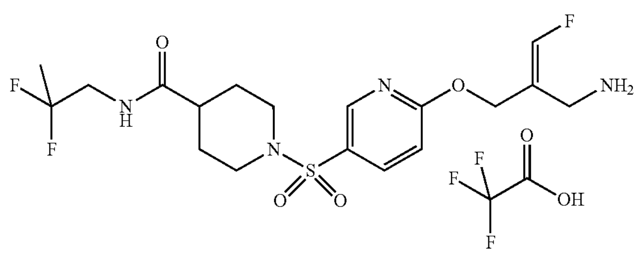 | VII.8 | 0.45 (HPLC-9) | 451 | 77 eq TFA; 1 h |
| 66 | 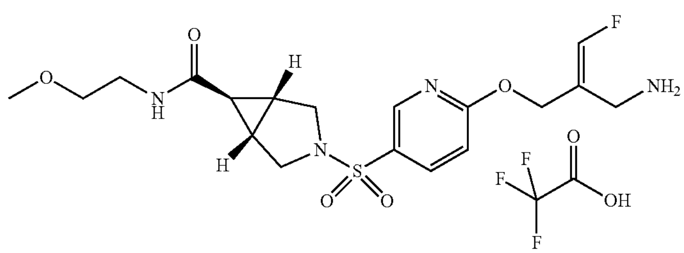 | VII.9 | 0.39 (HPLC-9) | 429 | exc. TFA; 1 h |

The invention claimed is:
1. A compound of formula (I)

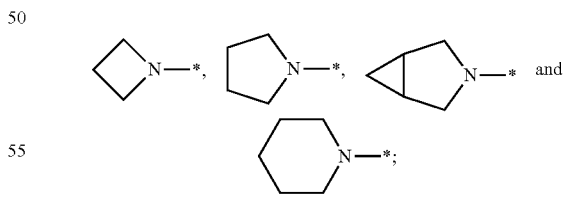

wherein
ring A is selected from the group consisting of:

R[1] is selected from the group consisting of H, F, Cl, Br, CN, —OH, $C_{1-4}$-alkyl, alkyl), —$(CH_2)_m$—COOH, —$(CH_2)_m$—C(=O)—O—($C_{1-4}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-4}$-alkyl)$_2$, —C(=O)—NH—$C_{3-6}$-cycloalkyl, —C(=O)—NH-heterocyclyl, —$(CH_2)_m$—NH—C(=O)—($C_{1-3}$-alkyl), —N($C_{1-3}$-alkyl)-C(=O)—($C_{1-4}$-alkyl), —N($C_{1-3}$-alkyl)-C(=O)—$NH_2$, —NH—C(=O)—NH—($C_{1-4}$-alkyl), heterocyclyl and phenyl, wherein each alkyl group or sub-group is optionally substituted with 1 or more F atoms or with one OH or —O—($C_{1-3}$-alkyl) group; and wherein each heterocyclyl is selected from the group consisting of azetidinyl, imidazolidinyl, piperidinylpiperidinyl, tetrahydropyranyl and morpholinyl, and each heterocycl is optionally substituted with one or two groups independently selected from the group consisting of oxo, $C_{1-3}$-alkyl, —C(=O)—$CH_3$ and —C(=O)-cyclopropyl; and wherein multiple $R^1$ may be identical or different, if n is 2; and n is an integer selected from 1 and 2; and m is an integer selected from 0, 1 and 2; and wherein in any definition mentioned hereinbefore, if not specified otherwise, any alkyl group or sub-group may be straight-chained or branched and is optionally substituted with 1 or more F atoms, or a salt thereof.

2. The compound of formula (I) according to claim 1, wherein $R^1$ is selected from the group consisting of:

H, F, Cl, —OH, —O—($C_{1-2}$-alkyl), —$(CH_2)_m$—COOH, —$(CH_2)_m$—C(=O)—O—($C_{1-2}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($CH_3$)($C_{1-3}$-alkyl), —C(=O)—NH-cyclopropyl, —C(=O)—NH-heterocyclyl, —$(CH_2)_m$—NH—C(=O)—($C_{1-3}$-alkyl), —N($C_{1-2}$-alkyl)-C(=O)—($C_{1-2}$-alkyl), —N($C_{1-2}$-alkyl)-C(=O)—$NH_2$, —NH—C(=O)—NH—($C_{1-2}$-alkyl), heterocyclyl and phenyl, wherein each alkyl group or sub-group is optionally substituted with 1 to 3 F atoms or with one OH or —O—($C_{1-2}$-alkyl) group; and wherein each heterocyclyl is selected from the group consisting of azetidinyl, imidazolidinyl, piperidinylpiperidinyl, tetrahydropyranyl and morpholinyl, and each heterocyclyl is optionally substituted with one or two groups independently selected from the group consisting of oxo, —C(=O)—$CH_3$ and —C(=O)-cyclopropyl; and wherein m is 0 or 1; and wherein multiple $R^1$ may be identical or different, if n is 2;

or a salt thereof.

3. The compound of formula (I) according to claim 2, wherein $R^1$ is selected from the group consisting of:

H, F, —OH, —$CH_3$, —$CF_3$, —O—$CH_3$, —COOH, —$(CH_2)_m$—C(=O)—O—$CH_3$, —$(CH_2)_m$—C(=O)—$NH_2$, —C(=O)—NH—($C_{1-3}$-alkyl), —$(CH_2)$—C(=O)—N($CH_3$)$_2$, —$(CH_2)$—C(=O)—N($CH_3$)($CH_2CH_3$), —C(=O)—NH-cyclopropyl, 1-(cyclopropylcarbonyl)-piperidin-4-yl and 3-methyl-2-oxo-imidazolidin-1-yl, wherein each ethyl group or sub-group in said $R^1$ group is optionally substituted in position 2 with one F atom, one OH or one —O—$CH_3$ group; and wherein each propyl group or sub-group in said $R^1$ group is optionally substituted in position 2 or 3 with 1 to 3 F atoms; and wherein m is 0 or 1; and wherein, if n is 2, multiple $R^1$ may be identical or different and the second $R^1$ group is selected from the group consisting of F, $CH_3$, $CF_3$ and phenyl;

or a salt thereof.

4. The compound of formula (I) according to claim 1, wherein ring A is

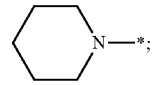

$R^1$ is selected from the group consisting of H, F, —OH, $C_{1-4}$-alkyl, —O—($C_{1-4}$-alkyl), —$(CH_2)_m$—COOH, —$(CH_2)_m$—C(=O)—O—($C_{1-4}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-4}$-alkyl)$_2$, —C(=O)—NH—$C_{3-6}$-cycloalkyl, —C(=O)—NH-heterocyclyl, —$(CH_2)_m$—NH—C(=O)—($C_{1-3}$-alkyl), —N($C_{1-3}$-alkyl)-C(=O)—($C_{1-4}$-alkyl), —N($C_{1-3}$-alkyl)-C(=O)—$NH_2$, —NH—C(=O)—NH—($C_{1-4}$-alkyl), heterocyclyl and phenyl, wherein each alkyl group or sub-group is optionally substituted with 1 or more F atoms or with one OH or —O—($C_{1-3}$-alkyl) group; and wherein each heterocyclyl is selected from the group consisting of azetidinyl, imidazolidinyl, piperidinyl, tetrahydropyranyl and morpholinyl, and each heterocyclyl is optionally substituted with one or two groups independently selected from the group consisting of oxo, $C_{1-3}$-alkyl, —C(=O)—$CH_3$ and —C(=O)-cyclopropyl; and wherein multiple $R^1$ may be identical or different, if n is 2; and n is an integer selected from 1 and 2; and m is an integer selected from 0 and 1; and or a salt thereof.

5. The compound of formula (I) according to claim 4, wherein $R^1$ is selected from the group consisting of:

H, —OH, $C_{1-2}$-alkyl, —O—($C_{1-2}$-alkyl), —$(CH_2)_m$—COOH, —$(CH_2)_m$—C(=O)—O—($C_{1-2}$-alkyl), —C(=O)-heterocyclyl, —$(CH_2)_m$—C(=O)—$NH_2$, —$(CH_2)_m$—C(=O)—NH—($C_{1-4}$-alkyl), —$(CH_2)_m$—C(=O)—N($C_{1-2}$-alkyl)$_2$, —C(=O)—NH—$C_{3-6}$-cyclopropyl, —C(=O)—NH-heterocyclyl, —$(CH_2)_m$—NH—C(=O)—($C_{1-3}$-alkyl), —N($CH_3$)—C(=O)—($C_{1-2}$-alkyl), —N($CH_3$)—C(=O)—$NH_2$, —NH—C(=O)—NH—($C_{1-3}$-alkyl), heterocyclyl and phenyl, wherein each alkyl group or sub-group is optionally substituted with 1 to 3 F atoms or with one OH or —O—$CH_3$ group; and wherein each heterocyclyl is selected from the group consisting of azetidinyl, imidazolidinyl, tetrahydropyranyl and morpholinyl, and each heterocyclyl is optionally substituted with one or two groups independently selected from the group consisting of oxo, $C_{1-3}$-alkyl and —C(=O)—$CH_3$; and wherein, if n is 2, multiple $R^1$ may be identical or different, the second $R^1$ group is selected from the group consisting of $CH_3$, $CF_3$ and phenyl;

or a salt thereof.

6. The compound of formula (I) according to claim 1, wherein ring A is

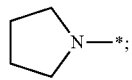

R¹ is selected from the group consisting of H, F, Cl, —OH, —O—(C₁₋₄-alkyl), —C(=O)-heterocyclyl, —(CH₂)ₘ—C(=O)—NH₂, —(CH₂)ₘ—C(=O)—NH—(C₁₋₄-alkyl), —(CH₂)ₘ—C(=O)—N(C₁₋₄-alkyl)₂, —(CH₂)ₘ—NH—C(=O)—(C₁₋₃-alkyl) and —N(C₁₋₃-alkyl)-C(=O)—(C₁₋₄-alkyl),
  wherein each alkyl group or sub-group is optionally substituted with 1 or more F atoms or with one OH or —O—(C₁₋₃-alkyl) group; and
  wherein each heterocyclyl is selected from the group consisting of azetidinyl, imidazolidinyl, piperidinyl, tetrahydropyranyl and morpholinyl, and each heterocyclyl is optionally substituted with one oxo or C₁₋₃-alkyl group; and
  wherein, if n is 2, multiple R¹ may be identical or different and the second R¹ group is F; and
n is an integer selected from 1 and 2; and
m is an integer selected from 0 and 1; and
or a salt thereof.

7. The compound of formula (I) according to claim 1, wherein
ring A is

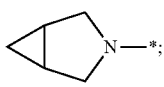

R¹ is selected from the group consisting of H, —(CH₂)ₘ—COOH, —(CH₂)ₘ—C(=O)—O—(C₁₋₄-alkyl), —C(=O)-heterocyclyl, —(CH₂)ₘ—C(=O)—NH₂, —(CH₂)ₘ—C(=O)—NH—(C₁₋₄-alkyl) and —(CH₂)ₘ—C(=O)—N(C₁₋₄-alkyl)₂,
  wherein each alkyl group or sub-group is optionally substituted with 1 or more F atoms or with one OH or —O—(C₁₋₃-alkyl) group; and
  wherein each heterocyclyl is selected from the group consisting of azetidinyl, imidazolidinyl, piperidinyl, tetrahydropyranyl and morpholinyl, and each heterocyclyl is optionally substituted with one oxo or C₁₋₃-alkyl group; and
  wherein multiple R¹ may be identical or different, if n is 2; and
n is 1; and
m is an integer selected from 0 and 1; and
or a salt thereof.

8. The compound of formula (I) according to claim 1, wherein
ring A is

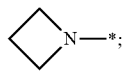

R¹ is selected from the group consisting of H, F, Cl, Br, CN, —OH, C₁₋₄-alkyl, —O—(C₁₋₄-alkyl), —C(=O)—NH₂, —C(=O)—NH—(C₁₋₄-alkyl), —C(=O)—N(C₁₋₄-alkyl)₂ and heterocyclyl,
  wherein each alkyl group or sub-group is optionally substituted with 1 or more F atoms or with one OH or —O—(C₁₋₃-alkyl) group; and
  wherein each heterocyclyl is selected from the group consisting of azetidinyl, and piperidinyl, and each heterocyclyl is optionally substituted with one C₁₋₃-alkyl, —C(=O)—CH₃ or —C(=O)-cyclopropyl group; and
  wherein, if n is 2, multiple R¹ may be identical or different and the second R¹ group is selected from the group consisting of F and CH₃; and
n is an integer selected from 1 and 2; and
or a salt thereof.

9. The compound of formula (I) according to claim 1 selected from the group consisting of:

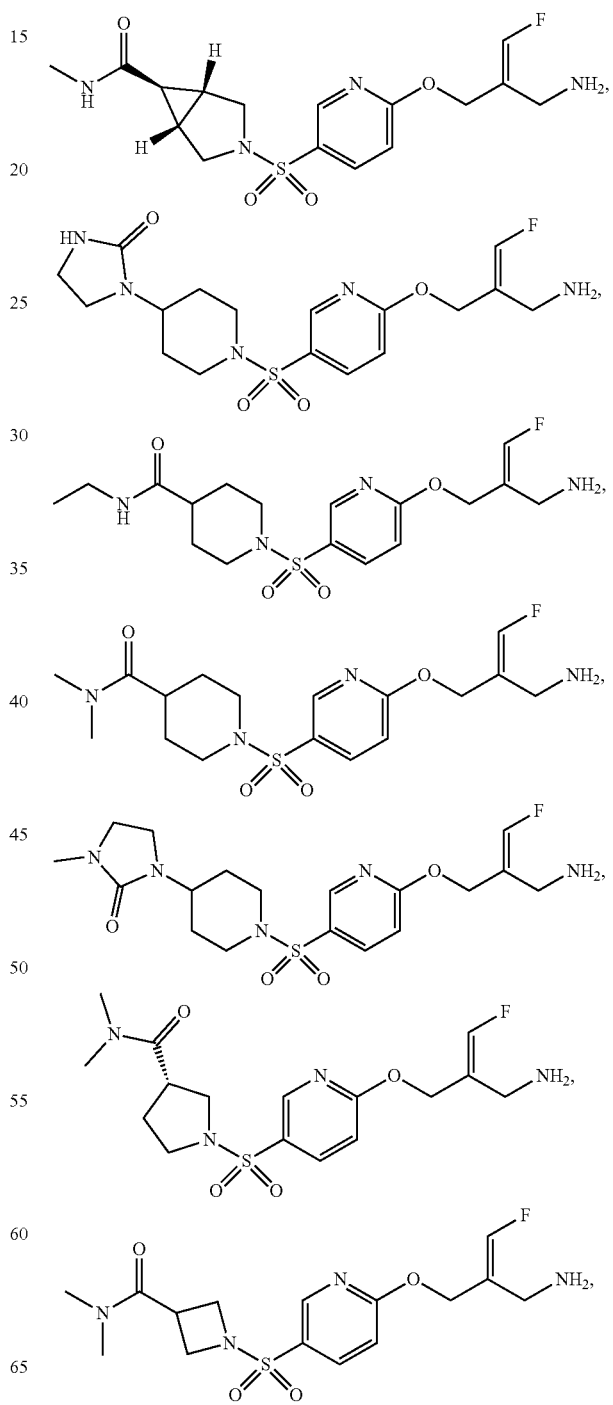

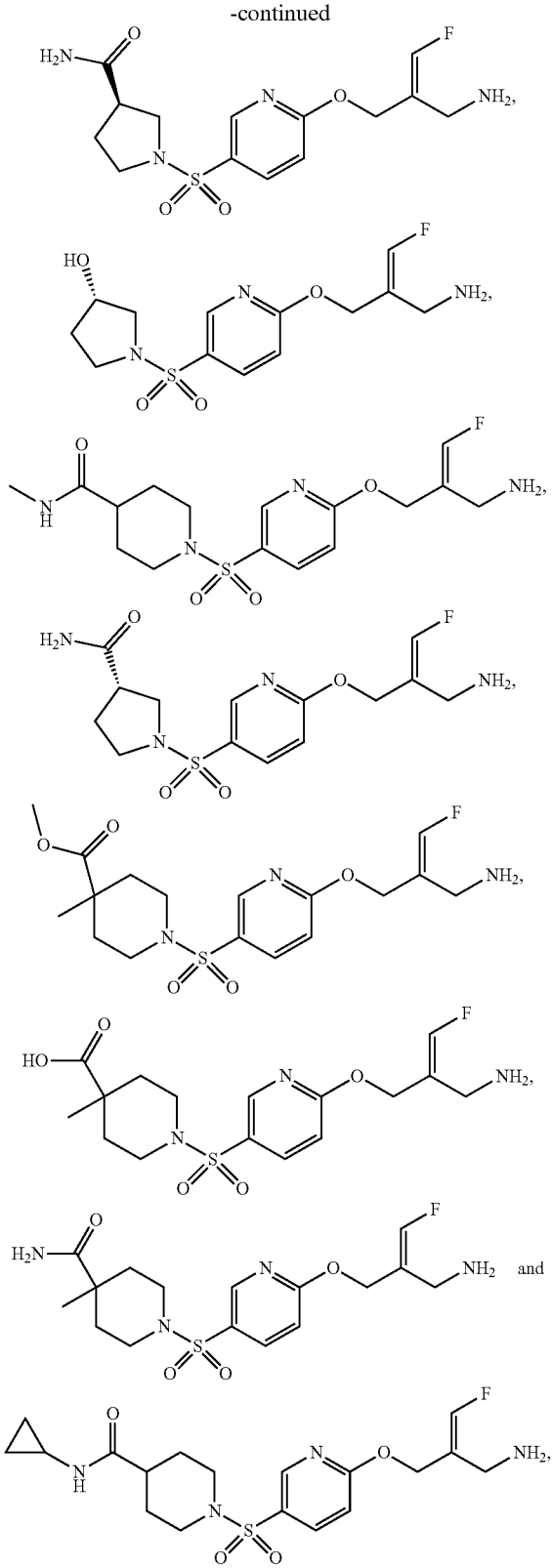

or a salt thereof.

10. A pharmaceutically acceptable salt of a compound according to claim 1.

11. A method for treating cancer, NASH (non-alcoholic steatohepatitis), pulmonary fibrosis, retinopathy, nephropathy or stroke, comprising administering a therapeutically effective amount of a compound according claim 1, or a pharmaceutically acceptable salt thereof, to a patient in need thereof.

12. A pharmaceutical composition comprising a compound according to claim 1, or a pharmaceutically acceptable salt thereof, optionally together with one or more inert carriers and/or diluents.

13. A method for treating a disease or condition which is mediated by inhibiting the activity of AOC3, comprising administering a therapeutically effective amount of a compound according to claim 1, or a pharmaceutically acceptable salt thereof.

14. A pharmaceutical composition comprising one or more compounds according to claim 1, or a pharmaceutically acceptable salt thereof, and one or more additional therapeutic agents, optionally together with one or more inert carriers and/or diluents.

15. The compound of formula (I) according to claim 9 having the structure:

16. The compound of formula (I) according to claim 9 having the structure:

or a pharmaceutically acceptable salt thereof.

17. The compound of formula (I) according to claim 9 having the structure:

or a pharmaceutically acceptable salt thereof.

18. The compound of formula (I) according to claim 9 having the structure:

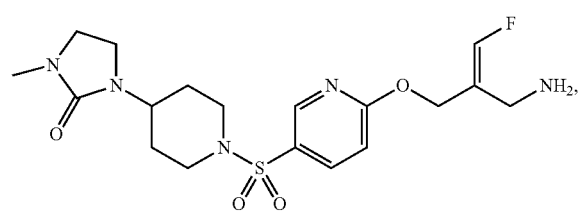 [SMILES: CN1CCN(C2CCN(S(=O)(=O)c3ccc(OC/C(=C/F)CN)nc3)CC2)C1=O]

or a pharmaceutically acceptable salt thereof.

19. The compound of formula (I) according to claim 9 having the structure:

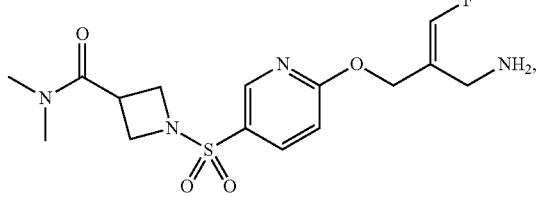

or a pharmaceutically acceptable salt thereof.

20. The compound of formula (I) according to claim 9 having the structure:

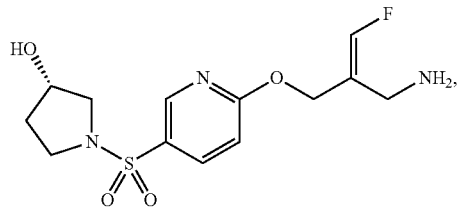 [SMILES: NC/C(=C\F)COc1ccc(S(=O)(=O)N2CC[C@H](O)C2)cn1]

or a pharmaceutically acceptable salt thereof.

21. The compound of formula (I) according to claim 9 having the structure:

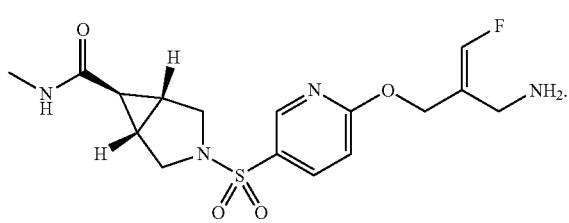 [SMILES: CNC(=O)[C@H]1[C@@H]2CN(S(=O)(=O)c3ccc(OC/C(=C/F)CN)nc3)C[C@@H]21]

22. The compound of formula (I) according to claim 9 having the structure:

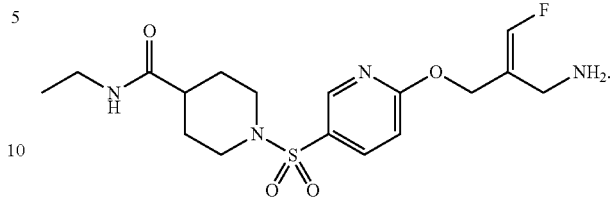

23. The compound of formula (I) according to claim 9 having the structure:

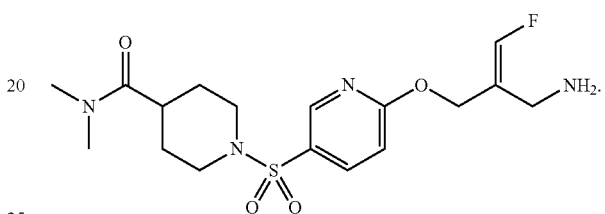

24. The compound of formula (I) according to claim 9 having the structure:

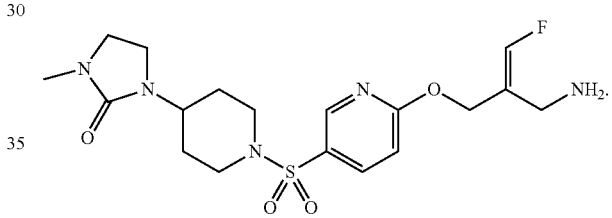

25. The compound of formula (I) according to claim 9 having the structure:

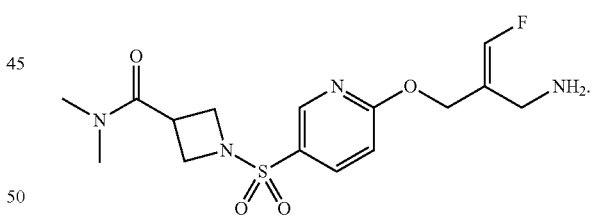

26. The compound of formula (I) according to claim 9 having the structure:

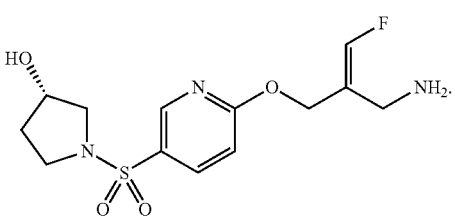 [SMILES: NC/C(=C\F)COc1ccc(S(=O)(=O)N2CC[C@H](O)C2)cn1]

\* \* \* \* \*